United States Patent
Doh et al.

(10) Patent No.: US 9,822,174 B2
(45) Date of Patent: Nov. 21, 2017

(54) ANTI-VEGF ANTIBODY, AND PHARMACEUTICAL COMPOSITION FOR PREVENTING, DIAGNOSING OR TREATING CANCER OR ANGIOGENESIS-RELATED DISEASES, CONTAINING SAME

(71) Applicants: DONG-A SOCIO HOLDINGS CO., LTD., Seoul (KR); DONG-A ST CO., LTD, Seoul (KR)

(72) Inventors: Hyounmie Doh, Seoul (KR); Byong Moon Kim, Seoul (KR); Chae Young Kim, Suwon-si (KR); Sung-Hee Lee, Seoul (KR); Dong-Hyeon Kim, Daejeon (KR); Yoo-jin Kim, Yongin-si (KR); Dongsop Lee, Yongin-si (KR); Kyung Mi Han, Yongin-si (KR); Dongsup Song, Suwon-si (KR); Eun-ee Jung, Seoul (KR); Jinseok Lee, Suwon-si (KR); Woo Jin Seung, Seoul (KR); Kyusang Hwang, Seoul (KR)

(73) Assignees: DONG-A SOCIO HOLDINGS CO., LTD., Seoul (KR); DONG-A ST CO., LTD, Seoul (KR)

( * ) Notice: Subject to any disclaimer, the term of this patent is extended or adjusted under 35 U.S.C. 154(b) by 76 days.

(21) Appl. No.: 14/893,813

(22) PCT Filed: May 30, 2014

(86) PCT No.: PCT/KR2014/004858
§ 371 (c)(1),
(2) Date: Nov. 24, 2015

(87) PCT Pub. No.: WO2014/193191
PCT Pub. Date: Dec. 4, 2014

(65) Prior Publication Data
US 2016/0122426 A1 May 5, 2016

(30) Foreign Application Priority Data

May 31, 2013 (KR) .......................... 10-2013-0062413

(51) Int. Cl.
*C07K 16/22* (2006.01)
*A61K 39/395* (2006.01)
*C07K 16/30* (2006.01)
*A61K 39/00* (2006.01)

(52) U.S. Cl.
CPC .......... *C07K 16/22* (2013.01); *A61K 39/3955* (2013.01); *C07K 16/30* (2013.01); *A61K 2039/505* (2013.01); *C07K 2317/24* (2013.01); *C07K 2317/33* (2013.01); *C07K 2317/54* (2013.01); *C07K 2317/55* (2013.01); *C07K 2317/565* (2013.01); *C07K 2317/622* (2013.01); *C07K 2317/73* (2013.01); *C07K 2317/76* (2013.01)

(58) Field of Classification Search
None
See application file for complete search history.

(56) References Cited

U.S. PATENT DOCUMENTS

| 7,060,269 B1 | 6/2006 | Baca et al. |
| 8,394,943 B2 | 3/2013 | Kavlie et al. |
| 2009/0142343 A1 | 6/2009 | Fuh et al. |
| 2015/0232549 A1 | 8/2015 | Fuh et al. |

FOREIGN PATENT DOCUMENTS

| CN | 102286101 B | 5/2013 |
| JP | 2011046732 A | 3/2011 |
| JP | 10-2013-0031136 A | 3/2013 |
| KR | 10-2008-0003453 A | 1/2008 |
| RU | 2011102583 A | 7/2012 |
| WO | 98/45331 A2 | 10/1998 |
| WO | 00/64946 A2 | 11/2000 |
| WO | 2011/159704 A1 | 12/2011 |
| WO | 2012/028716 A1 | 3/2012 |

OTHER PUBLICATIONS

Communication dated Jul. 14, 2016, from the Canadian Intellectual Property Office in counterpart Canadian application No. 2,913,126.
Sullivan, et al., "r84, a Novel Therapeutic Antibody against Mouse and Human VEGF with Potent Anti-Tumor Activity and Limited Toxicity Induction", PLoS One, Aug. 2010, vol. 5, Issue 8, pp. 1-13.
Shuangge Liu et al., "Efficacy of Anti-VEGF/VEGFR Agents on Animal Models of Endometriosis: A Systematic Review and Meta-Analysis", PLOS ONE, Nov. 17, 2016, DOI: 10.1371/journal.pone.0166658, p. 1-15.
European Patent Office, Communication dated Nov. 30, 2016 issued in counterpart European Application No. 14803672.6.
Russian Patent Office; Communication dated Feb. 22, 2017 in counterpart application No. 2015156461/10.
Ferrara, N., et al., "Discovery and Development of Bevacizumab, an Anti-VEGF Antibody for Treating Cancer", Nature Reviews | Drug Discovery, vol. 3, May 2004, p. 391 (1 page).
Rolf A. Brekken et al., "Selective Inhibition of Vascular Endothelial Growth Factor (VEGF) Receptor 2 (KDR/Flk-1) Activity by a Monoclonal Anti-VEGF Antibody Blocks Tumor Growth in Mice", Cancer Research, Sep. 2000, pp. 5117-5124, vol. 60, No. 18.
International Searching Authority, International Search Report of PCT/KR2014/004858 dated Sep. 2, 2014.
Japanese Patent Office; Communication dated Aug. 23, 2016 in counterpart application No. 2016-516455.

*Primary Examiner* — Phuong Huynh
(74) *Attorney, Agent, or Firm* — Sughrue Mion, PLLC

(57) ABSTRACT

A novel anti-vascular endothelial growth factor (VEGF) antibody having a strong binding affinity for VEGF and capable of inhibiting in vivo tumor growth and a composition for the treatment of cancer, containing the same. The antibody shows a remarkable binding property to human and mouse VEGF, suppresses the proliferation and permeability of a human umbilical vein endothelial cell (HUVEC) and inhibits tumor growth, and thus can be useful as an antibody for the treatment of cancer.

16 Claims, 17 Drawing Sheets

ANTI-VEGF ANTIBODY, AND PHARMACEUTICAL COMPOSITION FOR PREVENTING, DIAGNOSING OR TREATING CANCER OR ANGIOGENESIS-RELATED DISEASES, CONTAINING SAME

CROSS REFERENCE TO RELATED APPLICATIONS

This application is a National Stage of International Application No. PCT/KR2014/004858 filed May 30, 2014, claiming priority based on Korean Patent Application No. 10-2013-0062413 filed May 31, 2013, the contents of all of which are incorporated herein by reference in their entirety.

FIELD OF THE PRESENT INVENTION

The present invention relates to: a novel antibody that binds to vascular endothelial growth factor (VEGF) having a strong binding affinity for VEGF and thus can be useful for the treatment of cancer or angiogenesis-related disease; and a pharmaceutical composition containing the same.

BACKGROUND OF THE PRESENT INVENTION

It is well known that angiogenesis is involved in the pathogenesis of various diseases which include solid tumors, proliferative retinopathy or age-related macular degeneration (AMD) etc associated with ocular neovascularization.

A number of inducing factors such as aFGF, bFGF, TGF-α, TGF-β, HGF, TNF-β, and angiogenin, etc. have been identified in the studies on angiogenesis. Angiogenesis inhibitors may include thrombospondin, a 16 kDa N-terminal fragment of prolactin (Clapp et al., *Endocrinology*, 133: 1292-1299 (1993)), angiostatin, and endostatin, etc.

Whether angiogenesis is induced or inhibited depends on the balance between angiogenesis inducers and inhibitors (Folkman, J, et al., *J. Biol Chem.*, 267, 10931-10934 (1992)).

Among the angiogenesis inducers, vascular endothelial growth factor (VEGF) is involved in the development and homeostasis of blood vessels and lymphatic vessels, and exhibits significant effects on nerve cells as well. VEGF is produced mainly in vascular endothelial cells, hematopoietic cells and stromal cells under hypoxia or in response to stimulation by cell growth factors such as TGF, Interleukin and PDGF. VEGF binds to a VEGF receptor, and each isoform of VEGF binds to a specific receptor, which induces the formation of homo- or hetero-conjugate of the receptor, to activate each signal transduction pathway (Karsan A., *Int J. Mol Med.*, 5 (5):447-56 (2000)). Signaling specificity of a VEGF receptor is more finely modulated by co-receptors, such as neuropilin, heparan sulfate, integrin, and cadherin, etc. (Zachary I C, et al., *Mol. Biol. Cell.*, 22 (15):2766-76 (2011)). The VEGF is known to be an important mediator of disease-related angiogenesis in tumors and eyes. Also, VEGF mRNA is over-expressed by tumors in the majority of subjects investigated (Berkman et al., *J. Clin Invest.*, 91:153-159 (1993)). Since cancer requires new capillaries as a passage for nutrient supply and waste discharge for its growth, cancer cells and stromal cells thereof secrete VEGF continuously, which is spread throughout tissues and stimulates the migration of vascular endothelial cells (Ferrara. N et al., *Nat Rev. Cancer*, 2:795-803, (2002)). The neovasculatures induced by cancer cells are characterized by being incomplete as compared to the normally formed capillaries because they are unaided by surrounding cells. Although VEGF binds to receptors VEGFR1, 2 and 3, it is through VEGFR2 that VEGF delivers a signal leading to proliferation, migration and permeability of endothelial cells (H. Zeng et al., *J. Biol Chem*, 276:26969-26976 (2001)). Therefore, by controlling angiogenesis using drugs targeting VEGF, the proliferation of cancer cells and the diseases associated with angiogenesis can be treated. Among them, antibodies that bind to VEGF can be used as drugs, which undergo a humanization process in order to increase the binding affinity for VEGF and reduce the immunogenicity of the antibodies. Humanized antibodies are described in the literature [Bending, Methods: *Comp. Meth. Enzy.*, 8:83-93 (1995). Anti-VEGF neutralizing antibodies suppress the growth of various human tumor cell lines in nude mouse (Kim et al., *Nature*, 362:841-844 (1993); Warren et al., etc., *J. Clin Invest.*, 95: 1789-1797 (1995); Borgstroem et al., *Cancer Res.*, 56: 4032-4039 (1996); and Melnyk et al., *Cancer Res*, 56: 921-924 (1996)), and suppresses intraocular angiogenesis in a model of ischemic vascular disorders of retina (Adamis et al., *Arch Ophtalmol.*, 114:66-71 (1996)). Anti-VEGF antibody may be locally administered into the eye at an effective concentration to decrease the activity of VEGF. Such ischemic retinal disorders may include diabetic retinopathy or age-related macular degeneration.

Anti-VEGF neutralizing antibodies developed so far include bevacizumab (Avastin™, Genentech/Roche) which was approved for colorectal cancer by the FDA in February 2004. Bevacizumab's indication has been extended to the treatment of a total of six types of progressive tumors including metastatic colorectal cancer and progressive ovarian cancer. Additionally, a marketing authorization application for Aflibercept (Bayer Health Care), designed to bind to VEGF, was approved in 2011 by the FDA for the treatment of macular degeneration. However, in 2011 the FDA withdrew breast cancer-related indications of Avastin™ due to its failure to show significant increase in overall survival rates in breast cancer patients compared to placebo. Subsequent reports indicating that Avastin™ increases the risk of heart failure in breast cancer patients suggest that there is a need to improve upon previously developed anti-VEGF neutralizing antibodies, and to determine their exact efficacies at pre-clinical stage. Since Avastin™ does not bind to mouse VEGF, it is difficult to accurately determine its efficacy in pre-clinical models using mice. Thus, an object of the present invention is to develop an antibody that binds to both mouse and human VEGF, thereby acquiring reliability of the results in pre-clinical models; and to increase the binding affinity of the antibody to VEGF, thereby improving anti-tumor effect.

Through biopanning and affinity improvement, the present inventors have developed an antibody comprising a new complementarity determining region (CDR) which has not been previously known, and which through its specific binding to VEGF enables the treatment of tumors and various intraocular neovascular disorders.

SUMMARY OF THE PRESENT INVENTION

Therefore, it is an object of the present invention to provide an antibody that binds specifically to VEGF.

It is another object of the present invention to provide a pharmaceutical composition containing the above antibody.

To achieve the object of the present invention as stated above, an antibody is provided that binds to vascular endothelial growth factor (VEGF), the antibody comprising:

1) a light chain variable region comprising complementarity determining region (CDR)1, CDR2 and CDR3, wherein the CDR2 is represented by the amino acid sequence of SEQ ID NO 1; and the CDR3 is represented by the amino acid sequence of SEQ ID NO 2; and 2) a heavy chain variable region comprising CDR1, CDR2 and CDR3, wherein the CDR3 is represented by the amino acid sequence of SEQ ID NO 3.

To achieve another object of the present invention as above, there is provided a pharmaceutical composition comprising the above antibody for the prevention, diagnosis or treatment of cancer or an angiogenesis-related disorder caused by over-expression of VEGF.

The antibody of the present invention shows a remarkable binding property to human and mouse VEGF, suppresses the proliferation and permeability of a human umbilical vein endothelial cell (HUVEC) and inhibits tumor growth, and thus can be useful as an antibody for the prevention, diagnosis or treatment of cancer or an angiogenesis-related disease.

BRIEF DESCRIPTION OF THE DRAWINGS

The above and other objects and features of the present invention will become apparent from the following descriptions of the present invention, when taken in conjunction with the accompanying drawings.

DETAILED DESCRIPTION OF THE PRESENT INVENTION

Figure 1:
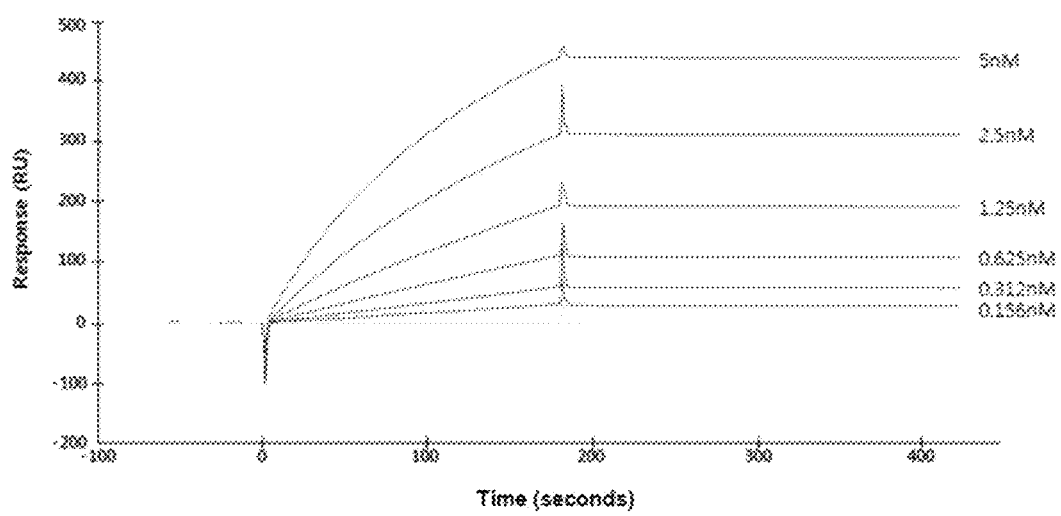
FIG. 1 shows the sensorgrams of association and dissociation of clone HF2-11 with VEGF.

In the present invention, there is provided an antibody that binds to VEGF (hereinafter, referred to as "anti-VEGF antibody"), the antibody comprising 1) a light chain variable region comprising CDR1, CDR2 and CDR3, wherein the CDR2 is represented by the amino acid sequence of SEQ ID NO 1; and the CDR3 is represented by the amino acid sequence of SEQ ID NO 2; and 2) a heavy chain variable region comprising CDR1, CDR2 and CDR3, wherein the CDR3 is represented by the amino acid sequence of SEQ ID NO 3.

The list of amino acid sequences of CDR1, CDR2, and CDR3 (hereinafter, referred to as LCDR1, LCDR2, and LCDR3, respectively) of the light chain variable regions; and CDR1, CDR2 and CDR3 (hereinafter, referred to as HCDR1, HCDR2, and HCDR3, respectively) of the heavy chain variable regions of the antibodies according to the present invention are shown in Table 1 below.

TABLE 1

Amino acid sequences of CDR1, CDR2 and CDR3 of the light and heavy chain variable regions

| Clones | LCDR1 | LCDR2 (SEQ: 1) | LCDR3 (SEQ: 2) | HCDR1 | HCDR2 | HCDR3 (SEQ: 3) |
|---|---|---|---|---|---|---|
| F | SGGSNSAYGYG (SEQ: 4) | WDDKRPS | GAWEYSSDVGI | GFTFSSHGMQ (SEQ: 15) | GISSDGSWTGYGAAVKG (SEQ: 35) | DFSTSYGADSIDA |
| HF2-1 | SGGSDSAYGYG (SEQ: 5) | WDDKRPS | GAWEYSGGVGI | NFVFRSHGMQ (SEQ: 16) | GISSDGSWTGYGAAVEG (SEQ: 36) | DFSTGYGADSIDA |
| HF2-2 | SGGSDSAYGYG (SEQ: 5) | WDDKRPS | GAWEYSGGVGI | RFNMRSHGMQ (SEQ: 17) | GISSDGSWERVGAAVEG (SEQ: 37) | DFSTGYGADSIDA |
| HF2-3 | SGGSDSAYGYG (SEQ: 5) | WDDKRPS | GAWEYSGGVGI | HFNMRSHGMQ (SEQ: 18) | GISSDGSWFRVAAAVEG (SEQ: 38) | DFSTGYGADSIDA |
| HF2-4 | SGGSDSAYGYG (SEQ: 5) | WDDKRPS | GAWEYSGGVGI | GWSMRSHGMQ (SEQ: 19) | GISSDGSWRRHSAAVEG (SEQ: 39) | DFSTGYGADSIDA |
| HF2-5 | SGGSDSAYGYG (SEQ: 5) | WDDKRPS | GAWEYSGGVGI | GFMIRSHGMQ (SEQ: 20) | GISSDGSWARHSAAVEG (SEQ: 40) | DFSTGYGADSIDA |
| HF2-6 | SGGSMEPLGYG (SEQ: 6) | WDDKRPS | GAWEYSGGVGI | RFLLRSHGMQ (SEQ: 21) | GISSDGSWFRVAAAVEG (SEQ: 38) | DFSTGYGADSIDA |
| HF2-7 | SGGSMEPLGYG (SEQ: 6) | WDDKRPS | GAWEYSGGVGI | QFWIRSHGMQ (SEQ: 22) | GISSDGSWFRVAAAVEG (SEQ: 38) | DFSTGYGADSIDA |

TABLE 1-continued

Amino acid sequences of CDR1, CDR2 and CDR3 of the light and heavy chain variable regions

| Clones | LCDR1 | LCDR2 (SEQ: 1) | LCDR3 (SEQ: 2) | HCDR1 | HCDR2 | HCDR3 (SEQ: 3) |
|---|---|---|---|---|---|---|
| HF2-8 | SGGSTYSLGYG (SEQ: 7) | WDDKRPS | GAWEYSGGVGI | GFHIRSHGMQ (SEQ: 23) | GISSDGSWLKLSAAVEG (SEQ: 41) | DFSTGYGADSIDA |
| HF2-9 | SGGSMEPLGYG (SEQ: 6) | WDDKRPS | GAWEYSGGVGI | MFRIRSHGMQ (SEQ: 24) | GISSDGSWFRVAAAVEG (SEQ: 38) | DFSTGYGADSIDA |
| HF2-10 | SGGSMEPLGYG (SEQ: 6) | WDDKRPS | GAWEYSGGVGI | FQYFRSHGMQ (SEQ: 25) | GISSDGSWFRVAAAVEG (SEQ: 38) | DFSTGYGADSIDA |
| HF2-11 | SGGSSEPLGYG (SEQ: 8) | WDDKRPS | GAWEYSGGVGI | GFLIRSHGMQ (SEQ: 26) | GISSDGSWVKVAAAVEG (SEQ: 42) | DFSTGYGADSIDA |
| HF2-12 | SGGSMEPLGYG (SEQ: 6) | WDDKRPS | GAWEYSGGVGI | YSEVRSHGMQ (SEQ: 27) | GISSDGSWFRVAAAVEG (SEQ: 38) | DFSTGYGADSIDA |
| HF2-13 | SGGSDLLLGYG (SEQ: 9) | WDDKRPS | GAWEYSGGVGI | GFLVRSHGMQ (SEQ: 28) | GISSDGSWQRVNAAVEG (SEQ: 43) | DFSTGYGADSIDA |
| HF2-14 | SGGSDSAYGYG (SEQ: 5) | WDDKRPS | GAWEYSGGVGI | HSSIRSHGMQ (SEQ: 29) | GISSDGSWLRQDAAVEG (SEQ: 44) | DFSTGYGADSIDA |
| HF2-15 | SGGSQESLGYG (SEQ: 10) | WDDKRPS | GAWEYSGGVGI | GFVVRSHGMQ (SEQ: 30) | GISSDGSWKATAAAVEG (SEQ: 45) | DFSTGYGADSIDA |
| HF2-16 | SGGSIEPLGYG (SEQ: 11) | WDDKRPS | GAWEYSGGVGI | GFRIRSHGMQ (SEQ: 31) | GISSDGSWVKVAAAVEG (SEQ: 42) | DFSTGYGADSIDA |
| HF2-17 | SGGSIEPLGYG (SEQ: 11) | WDDKRPS | GAWEYSGGVGI | GFMIRSHGMQ (SEQ: 20) | GISSDGSWRRHSAAVEG (SEQ: 39) | DFSTGYGADSIDA |
| HF2-18 | SGGSIEPLGYG (SEQ: 11) | WDDKRPS | GAWEYSGGVGI | YWAFRSHGMQ (SEQ: 32) | GISSDGSWFSSAAAVEG (SEQ: 46) | DFSTGYGADSIDA |
| HF2-19 | SGGSDSAYGYG (SEQ: 5) | WDDKRPS | GAWEYSGGVGI | GFSTRSHGMQ (SEQ: 33) | GISSDGSWKATAAAVEG (SEQ: 45) | DFSTGYGADSIDA |
| HF2-20 | SGGSDSAYGYG (SEQ: 5) | WDDKRPS | GAWEYSGGVGI | YMEYRSHGMQ (SEQ: 34) | GISSDGSWSRVDAAVEG (SEQ: 47) | DFSTGYGADSIDA |
| HF2-21 | SGGSMEPLGYG (SEQ: 6) | WDDKRPS | GAWEYSGGVGI | FQYFRSHGMQ (SEQ: 25) | GISSDGSWYRVQAAVEG (SEQ: 48) | DFSTGYGADSIDA |
| HF2-22 | SGGSTAGVGYG (SEQ: 12) | WDDKRPS | GAWEYSGGVGI | GFRIRSHGMQ (SEQ: 31) | GISSDGSWFRVAAAVEG (SEQ: 38) | DFSTGYGADSIDA |
| HF2-23 | SGGSDLLLGYG (SEQ: 9) | WDDKRPS | GAWEYSGGVGI | GFRIRSHGMQ (SEQ: 31) | GISSDGSWFSSAAAVEG (SEQ: 46) | DFSTGYGADSIDA |
| HF2-24 | SGGSQESLGYG (SEQ: 10) | WDDKRPS | GAWEYSGGVGI | RFNMRSHGMQ (SEQ: 17) | GISSDGSWVKVAAAVEG (SEQ: 42) | DFSTGYGADSIDA |
| HF2-25 | SGGSNFPMGYG (SEQ: 13) | WDDKRPS | GAWEYSGGVGI | YMEYRSHGMQ (SEQ: 34) | GISSDGSWFRMNAAVEG (SEQ: 49) | DFSTGYGADSIDA |
| HF2-26 | TAPADSAYGYG (SEQ: 14) | WDDKRPS | GAWEYSGGVGI | RFNMRSHGMQ (SEQ: 17) | GISSDGSWIRVQAAVEG (SEQ: 50) | DFSTGYGADSIDA |

The antibody that binds to VEGF according to the present invention may comprise 1) a light chain variable region comprising CDR1 represented by the amino acid sequence selected from a group consisting of SEQ ID NOs 4-14; CDR 2 represented by the amino acid sequence of SEQ ID NO 1; and CDR3 represented by the amino acid sequence of SEQ ID NO 2; and 2) a heavy chain variable region comprising CDR1 represented by the amino acid sequence selected from a group consisting of SEQ ID NOs 15-34; CDR 2 represented by the amino acid sequence selected from a group consisting of SEQ ID NOs 35-50; and CDR3 represented by the amino acid sequence of SEQ ID NO 3.

The anti-VEGF antibody according to one embodiment of the present invention may comprise 1) a light chain variable region comprising CDR1 represented by the amino acid sequence of SEQ ID NO 4; CDR 2 represented by the amino acid sequence of SEQ ID NO 1; and CDR3 represented by the amino acid sequence of SEQ ID NO 2; and 2) a heavy chain variable region comprising CDR1 represented by the amino acid sequence of SEQ ID NOs 15; CDR 2 represented by the amino acid sequence of SEQ ID NO 35; and CDR3 represented by the amino acid sequence of SEQ ID NO 3.

The anti-VEGF antibody according to one embodiment of the present invention may comprise 1) a light chain variable region comprising CDR1 represented by the amino acid sequence of SEQ ID NO 5; CDR 2 represented by the amino acid sequence of SEQ ID NO 1; and CDR3 represented by the amino acid sequence of SEQ ID NO 2; and 2) a heavy chain variable region comprising CDR1 represented by the amino acid sequence of SEQ ID NO 16; CDR 2 represented by the amino acid sequence of SEQ ID NO 36; and CDR3 represented by the amino acid sequence of SEQ ID NO 3.

The anti-VEGF antibody according to one embodiment of the present invention may comprise 1) a light chain variable region comprising CDR1 represented by the amino acid sequence of SEQ ID NO 5; CDR 2 represented by the amino acid sequence of SEQ ID NO 1; and CDR3 represented by the amino acid sequence of SEQ ID NO 2; and 2) a heavy chain variable region comprising CDR1 represented by the amino acid sequence of SEQ ID NO 17; CDR 2 represented by the amino acid sequence of SEQ ID NO 37; and CDR3 represented by the amino acid sequence of SEQ ID NO 3.

The anti-VEGF antibody according to one embodiment of the present invention may comprise 1) a light chain variable region comprising CDR1 represented by the amino acid sequence of SEQ ID NO 5; CDR 2 represented by the amino acid sequence of SEQ ID NO 1; and CDR3 represented by the amino acid sequence of SEQ ID NO 2; and 2) a heavy chain variable region comprising CDR1 represented by the amino acid sequence of SEQ ID NO 18; CDR 2 represented by the amino acid sequence of SEQ ID NO 38; and CDR3 represented by the amino acid sequence of SEQ ID NO 3.

The anti-VEGF antibody according to one embodiment of the present invention may comprise 1) a light chain variable region comprising CDR1 represented by the amino acid sequence of SEQ ID NO 5; CDR 2 represented by the amino acid sequence of SEQ ID NO 1; and CDR3 represented by the amino acid sequence of SEQ ID NO 2; and 2) a heavy chain variable region comprising CDR1 represented by the amino acid sequence of SEQ ID NO 19; CDR 2 represented by the amino acid sequence of SEQ ID NO 39; and CDR3 represented by the amino acid sequence of SEQ ID NO 3.

The anti-VEGF antibody according to one embodiment of the present invention may comprise 1) a light chain variable region comprising CDR1 represented by the amino acid sequence of SEQ ID NO 5; CDR 2 represented by the amino acid sequence of SEQ ID NO 1; and CDR3 represented by the amino acid sequence of SEQ ID NO 2; and 2) a heavy chain variable region comprising CDR1 represented by the amino acid sequence of SEQ ID NO 20; CDR 2 represented by the amino acid sequence of SEQ ID NO 40; and CDR3 represented by the amino acid sequence of SEQ ID NO 3.

The anti-VEGF antibody according to one embodiment of the present invention may comprise 1) a light chain variable region comprising CDR1 represented by the amino acid sequence of SEQ ID NO 6; CDR 2 represented by the amino acid sequence of SEQ ID NO 1; and CDR3 represented by the amino acid sequence of SEQ ID NO 2; and 2) a heavy chain variable region comprising CDR1 represented by the amino acid sequence of SEQ ID NO 21; CDR 2 represented by the amino acid sequence of SEQ ID NO 38; and CDR3 represented by the amino acid sequence of SEQ ID NO 3.

The anti-VEGF antibody according to one embodiment of the present invention may comprise 1) a light chain variable region comprising CDR1 represented by the amino acid sequence of SEQ ID NO 6; CDR 2 represented by the amino acid sequence of SEQ ID NO 1; and CDR3 represented by the amino acid sequence of SEQ ID NO 2; and 2) a heavy chain variable region comprising CDR1 represented by the amino acid sequence of SEQ ID NO 22; CDR 2 represented by the amino acid sequence of SEQ ID NO 38; and CDR3 represented by the amino acid sequence of SEQ ID NO 3.

The anti-VEGF antibody according to one embodiment of the present invention may comprise 1) a light chain variable region comprising CDR1 represented by the amino acid sequence of SEQ ID NO 7; CDR 2 represented by the amino acid sequence of SEQ ID NO 1; and CDR3 represented by the amino acid sequence of SEQ ID NO 2; and 2) a heavy chain variable region comprising CDR1 represented by the amino acid sequence of SEQ ID NO 23; CDR 2 represented by the amino acid sequence of SEQ ID NO 41; and CDR3 represented by the amino acid sequence of SEQ ID NO 3.

The anti-VEGF antibody according to one embodiment of the present invention may comprise 1) a light chain variable region comprising CDR1 represented by the amino acid sequence of SEQ ID NO 6; CDR 2 represented by the amino acid sequence of SEQ ID NO 1; and CDR3 represented by the amino acid sequence of SEQ ID NO 2; and 2) a heavy chain variable region comprising CDR1 represented by the amino acid sequence of SEQ ID NO 24; CDR 2 represented by the amino acid sequence of SEQ ID NO 38; and CDR3 represented by the amino acid sequence of SEQ ID NO 3.

The anti-VEGF antibody according to one embodiment of the present invention may comprise 1) a light chain variable region comprising CDR1 represented by the amino acid sequence of SEQ ID NO 6; CDR 2 represented by the amino acid sequence of SEQ ID NO 1; and CDR3 represented by the amino acid sequence of SEQ ID NO 2; and 2) a heavy chain variable region comprising CDR1 represented by the amino acid sequence of SEQ ID NO 25; CDR 2 represented by the amino acid sequence of SEQ ID NO 38; and CDR3 represented by the amino acid sequence of SEQ ID NO 3.

The anti-VEGF antibody according to one embodiment of the present invention may comprise 1) a light chain variable region comprising CDR1 represented by the amino acid sequence of SEQ ID NO 8; CDR 2 represented by the amino acid sequence of SEQ ID NO 1; and CDR3 represented by the amino acid sequence of SEQ ID NO 2; and 2) a heavy chain variable region comprising CDR1 represented by the amino acid sequence of SEQ ID NO 26; CDR 2 represented by the amino acid sequence of SEQ ID NO 42; and CDR3 represented by the amino acid sequence of SEQ ID NO 3.

The anti-VEGF antibody according to one embodiment of the present invention may comprise 1) a light chain variable region comprising CDR1 represented by the amino acid sequence of SEQ ID NO 6; CDR 2 represented by the amino acid sequence of SEQ ID NO 1; and CDR3 represented by the amino acid sequence of SEQ ID NO 2; and 2) a heavy chain variable region comprising CDR1 represented by the amino acid sequence of SEQ ID NO 27; CDR 2 represented by the amino acid sequence of SEQ ID NO 38; and CDR3 represented by the amino acid sequence of SEQ ID NO 3.

The anti-VEGF antibody according to one embodiment of the present invention may comprise 1) a light chain variable region comprising CDR1 represented by the amino acid sequence of SEQ ID NO 9; CDR 2 represented by the amino acid sequence of SEQ ID NO 1; and CDR3 represented by the amino acid sequence of SEQ ID NO 2; and 2) a heavy chain variable region comprising CDR1 represented by the amino acid sequence of SEQ ID NO 28; CDR 2 represented by the amino acid sequence of SEQ ID NO 43; and CDR3 represented by the amino acid sequence of SEQ ID NO 3.

The anti-VEGF antibody according to one embodiment of the present invention may comprise 1) a light chain variable region comprising CDR1 represented by the amino acid sequence of SEQ ID NO 5; CDR 2 represented by the amino acid sequence of SEQ ID NO 1; and CDR3 represented by the amino acid sequence of SEQ ID NO 2; and 2) a heavy chain variable region comprising CDR1 represented by the amino acid sequence of SEQ ID NO 29; CDR 2 represented by the amino acid sequence of SEQ ID NO 44; and CDR3 represented by the amino acid sequence of SEQ ID NO 3.

The anti-VEGF antibody according to one embodiment of the present invention may comprise 1) a light chain variable region comprising CDR1 represented by the amino acid sequence of SEQ ID NO 10; CDR 2 represented by the amino acid sequence of SEQ ID NO 1; and CDR3 represented by the amino acid sequence of SEQ ID NO 2; and 2) a heavy chain variable region comprising CDR1 represented by the amino acid sequence of SEQ ID NO 30; CDR 2 represented by the amino acid sequence of SEQ ID NO 45; and CDR3 represented by the amino acid sequence of SEQ ID NO 3.

The anti-VEGF antibody according to one embodiment of the present invention may comprise 1) a light chain variable region comprising CDR1 represented by the amino acid sequence of SEQ ID NO 11; CDR 2 represented by the amino acid sequence of SEQ ID NO 1; and CDR3 represented by the amino acid sequence of SEQ ID NO 2; and 2) a heavy chain variable region comprising CDR1 represented by the amino acid sequence of SEQ ID NO 31; CDR 2 represented by the amino acid sequence of SEQ ID NO 42; and CDR3 represented by the amino acid sequence of SEQ ID NO 3.

The anti-VEGF antibody according to one embodiment of the present invention may comprise 1) a light chain variable region comprising CDR1 represented by the amino acid sequence of SEQ ID NO 11; CDR 2 represented by the amino acid sequence of SEQ ID NO 1; and CDR3 represented by the amino acid sequence of SEQ ID NO 2; and 2) a heavy chain variable region comprising CDR1 represented by the amino acid sequence of SEQ ID NO 20; CDR 2 represented by the amino acid sequence of SEQ ID NO 39; and CDR3 represented by the amino acid sequence of SEQ ID NO 3.

The anti-VEGF antibody according to one embodiment of the present invention may comprise 1) a light chain variable region comprising CDR1 represented by the amino acid sequence of SEQ ID NO 11; CDR 2 represented by the amino acid sequence of SEQ ID NO 1; and CDR3 represented by the amino acid sequence of SEQ ID NO 2; and 2) a heavy chain variable region comprising CDR1 represented by the amino acid sequence of SEQ ID NO 32; CDR 2 represented by the amino acid sequence of SEQ ID NO 46; and CDR3 represented by the amino acid sequence of SEQ ID NO 3.

The anti-VEGF antibody according to one embodiment of the present invention may comprise 1) a light chain variable region comprising CDR1 represented by the amino acid sequence of SEQ ID NO 5; CDR 2 represented by the amino acid sequence of SEQ ID NO 1; and CDR3 represented by the amino acid sequence of SEQ ID NO 2; and 2) a heavy chain variable region comprising CDR1 represented by the amino acid sequence of SEQ ID NO 33; CDR 2 represented by the amino acid sequence of SEQ ID NO 45; and CDR3 represented by the amino acid sequence of SEQ ID NO 3.

The anti-VEGF antibody according to one embodiment of the present invention may comprise 1) a light chain variable region comprising CDR1 represented by the amino acid sequence of SEQ ID NO 5; CDR 2 represented by the amino acid sequence of SEQ ID NO 1; and CDR3 represented by the amino acid sequence of SEQ ID NO 2; and 2) a heavy chain variable region comprising CDR1 represented by the amino acid sequence of SEQ ID NO 34; CDR 2 represented by the amino acid sequence of SEQ ID NO 47; and CDR3 represented by the amino acid sequence of SEQ ID NO 3.

The anti-VEGF antibody according to one embodiment of the present invention may comprise 1) a light chain variable region comprising CDR1 represented by the amino acid sequence of SEQ ID NO 6; CDR 2 represented by the amino acid sequence of SEQ ID NO 1; and CDR3 represented by the amino acid sequence of SEQ ID NO 2; and 2) a heavy chain variable region comprising CDR1 represented by the amino acid sequence of SEQ ID NO 25; CDR 2 represented by the amino acid sequence of SEQ ID NO 48; and CDR3 represented by the amino acid sequence of SEQ ID NO 3.

The anti-VEGF antibody according to one embodiment of the present invention may comprise 1) a light chain variable region comprising CDR1 represented by the amino acid sequence of SEQ ID NO 12; CDR 2 represented by the amino acid sequence of SEQ ID NO 1; and CDR3 represented by the amino acid sequence of SEQ ID NO 2; and 2) a heavy chain variable region comprising CDR1 represented by the amino acid sequence of SEQ ID NO 31; CDR 2 represented by the amino acid sequence of SEQ ID NO 38; and CDR3 represented by the amino acid sequence of SEQ ID NO 3.

The anti-VEGF antibody according to one embodiment of the present invention may comprise 1) a light chain variable region comprising CDR1 represented by the amino acid sequence of SEQ ID NO 9; CDR 2 represented by the amino acid sequence of SEQ ID NO 1; and CDR3 represented by the amino acid sequence of SEQ ID NO 2; and 2) a heavy chain variable region comprising CDR1 represented by the amino acid sequence of SEQ ID NO 31; CDR 2 represented by the amino acid sequence of SEQ ID NO 46; and CDR3 represented by the amino acid sequence of SEQ ID NO 3.

The anti-VEGF antibody according to one embodiment of the present invention may comprise 1) a light chain variable region comprising CDR1 represented by the amino acid sequence of SEQ ID NO 10; CDR 2 represented by the amino acid sequence of SEQ ID NO 1; and CDR3 represented by the amino acid sequence of SEQ ID NO 2; and 2) a heavy chain variable region comprising CDR1 represented by the amino acid sequence of SEQ ID NO 17; CDR 2 represented by the amino acid sequence of SEQ ID NO 42; and CDR3 represented by the amino acid sequence of SEQ ID NO 3.

The anti-VEGF antibody according to one embodiment of the present invention may comprise 1) a light chain variable region comprising CDR1 represented by the amino acid sequence of SEQ ID NO 13; CDR 2 represented by the amino acid sequence of SEQ ID NO 1; and CDR3 represented by the amino acid sequence of SEQ ID NO 2; and 2) a heavy chain variable region comprising CDR1 represented by the amino acid sequence of SEQ ID NO 34; CDR 2 represented by the amino acid sequence of SEQ ID NO 49; and CDR3 represented by the amino acid sequence of SEQ ID NO 3.

The anti-VEGF antibody according to one embodiment of the present invention may comprise 1) a light chain variable region comprising CDR1 represented by the amino acid sequence of SEQ ID NO 14; CDR 2 represented by the amino acid sequence of SEQ ID NO 1; and CDR3 represented by the amino acid sequence of SEQ ID NO 2; and 2) a heavy chain variable region comprising CDR1 represented by the amino acid sequence of SEQ ID NO 17; CDR 2 represented by the amino acid sequence of SEQ ID NO 50; and CDR3 represented by the amino acid sequence of SEQ ID NO 3.

The antibody that binds to VEGF according to the present invention may comprise 1) a light chain variable region represented by the amino acid sequence selected from a group consisting of SEQ ID NOs 54-65; and 2) a heavy chain variable region represented by the amino acid sequence selected from a group consisting of SEQ ID NOs 78-104 (see Table 2).

The anti-VEGF antibody according to one embodiment of the present invention may comprise 1) a light chain variable region represented by the amino acid sequence of SEQ ID NO 54; and 2) a heavy chain variable region represented by the amino acid sequence of SEQ ID NO 78.

The anti-VEGF antibody according to one embodiment of the present invention may comprise 1) a light chain variable region represented by the amino acid sequence of SEQ ID NO 55; and 2) a heavy chain variable region represented by the amino acid sequence of SEQ ID NO 79.

The anti-VEGF antibody according to one embodiment of the present invention may comprise 1) a light chain variable region represented by the amino acid sequence of SEQ ID NO 55; and 2) a heavy chain variable region represented by the amino acid sequence of SEQ ID NO 80.

The anti-VEGF antibody according to one embodiment of the present invention may comprise 1) a light chain variable region represented by the amino acid sequence of SEQ ID NO 56; and 2) a heavy chain variable region represented by the amino acid sequence of SEQ ID NO 81.

The anti-VEGF antibody according to one embodiment of the present invention may comprise 1) a light chain variable region represented by the amino acid sequence of SEQ ID NO 55; and 2) a heavy chain variable region represented by the amino acid sequence of SEQ ID NO 82.

The anti-VEGF antibody according to one embodiment of the present invention may comprise 1) a light chain variable region represented by the amino acid sequence of SEQ ID NO 55; and 2) a heavy chain variable region represented by the amino acid sequence of SEQ ID NO 83.

The anti-VEGF antibody according to one embodiment of the present invention may comprise 1) a light chain variable region represented by the amino acid sequence of SEQ ID NO 57; and 2) a heavy chain variable region represented by the amino acid sequence of SEQ ID NO 84.

The anti-VEGF antibody according to one embodiment of the present invention may comprise 1) a light chain variable region represented by the amino acid sequence of SEQ ID NO 57; and 2) a heavy chain variable region represented by the amino acid sequence of SEQ ID NO 85.

The anti-VEGF antibody according to one embodiment of the present invention may comprise 1) a light chain variable region represented by the amino acid sequence of SEQ ID NO 58; and 2) a heavy chain variable region represented by the amino acid sequence of SEQ ID NO 86.

The anti-VEGF antibody according to one embodiment of the present invention may comprise 1) a light chain variable region represented by the amino acid sequence of SEQ ID NO 57; and 2) a heavy chain variable region represented by the amino acid sequence of SEQ ID NO 87.

The anti-VEGF antibody according to one embodiment of the present invention may comprise 1) a light chain variable region represented by the amino acid sequence of SEQ ID NO 57; and 2) a heavy chain variable region represented by the amino acid sequence of SEQ ID NO 88.

The anti-VEGF antibody according to one embodiment of the present invention may comprise 1) a light chain variable region represented by the amino acid sequence of SEQ ID NO 59; and 2) a heavy chain variable region represented by the amino acid sequence of SEQ ID NO 89.

The anti-VEGF antibody according to one embodiment of the present invention may comprise 1) a light chain variable region represented by the amino acid sequence of SEQ ID NO 57; and 2) a heavy chain variable region represented by the amino acid sequence of SEQ ID NO 90.

The anti-VEGF antibody according to one embodiment of the present invention may comprise 1) a light chain variable region represented by the amino acid sequence of SEQ ID NO 60; and 2) a heavy chain variable region represented by the amino acid sequence of SEQ ID NO 91.

The anti-VEGF antibody according to one embodiment of the present invention may comprise 1) a light chain variable region represented by the amino acid sequence of SEQ ID NO 55; and 2) a heavy chain variable region represented by the amino acid sequence of SEQ ID NO 92.

The anti-VEGF antibody according to one embodiment of the present invention may comprise 1) a light chain variable region represented by the amino acid sequence of SEQ ID NO 61; and 2) a heavy chain variable region represented by the amino acid sequence of SEQ ID NO 93.

The anti-VEGF antibody according to one embodiment of the present invention may comprise 1) a light chain variable region represented by the amino acid sequence of SEQ ID NO 62; and 2) a heavy chain variable region represented by the amino acid sequence of SEQ ID NO 94.

The anti-VEGF antibody according to one embodiment of the present invention may comprise 1) a light chain variable region represented by the amino acid sequence of SEQ ID NO 62; and 2) a heavy chain variable region represented by the amino acid sequence of SEQ ID NO 95.

The anti-VEGF antibody according to one embodiment of the present invention may comprise 1) a light chain variable region represented by the amino acid sequence of SEQ ID NO 62; and 2) a heavy chain variable region represented by the amino acid sequence of SEQ ID NO 96.

The anti-VEGF antibody according to one embodiment of the present invention may comprise 1) a light chain variable region represented by the amino acid sequence of SEQ ID NO 55; and 2) a heavy chain variable region represented by the amino acid sequence of SEQ ID NO 97.

The anti-VEGF antibody according to one embodiment of the present invention may comprise 1) a light chain variable region represented by the amino acid sequence of SEQ ID NO 55; and 2) a heavy chain variable region represented by the amino acid sequence of SEQ ID NO 98.

The anti-VEGF antibody according to one embodiment of the present invention may comprise 1) a light chain variable region represented by the amino acid sequence of SEQ ID NO 57; and 2) a heavy chain variable region represented by the amino acid sequence of SEQ ID NO 99.

The anti-VEGF antibody according to one embodiment of the present invention may comprise 1) a light chain variable region represented by the amino acid sequence of SEQ ID NO 63; and 2) a heavy chain variable region represented by the amino acid sequence of SEQ ID NO 100.

The anti-VEGF antibody according to one embodiment of the present invention may comprise 1) a light chain variable region represented by the amino acid sequence of SEQ ID NO 60; and 2) a heavy chain variable region represented by the amino acid sequence of SEQ ID NO 101.

The anti-VEGF antibody according to one embodiment of the present invention may comprise 1) a light chain variable region represented by the amino acid sequence of SEQ ID NO 61; and 2) a heavy chain variable region represented by the amino acid sequence of SEQ ID NO 102.

The anti-VEGF antibody according to one embodiment of the present invention may comprise 1) a light chain variable region represented by the amino acid sequence of SEQ ID NO 64; and 2) a heavy chain variable region represented by the amino acid sequence of SEQ ID NO 103.

The anti-VEGF antibody according to one embodiment of the present invention may comprise 1) a light chain variable region represented by the amino acid sequence of SEQ ID NO 65; and 2) a heavy chain variable region represented by the amino acid sequence of SEQ ID NO 104.

The antibody of the present invention may comprise a light chain constant region and a heavy chain constant region, the light chain constant region and the heavy chain constant region may be a light chain constant region and a heavy chain constant region of a publicly known human antibody (U Rutishauser et al., *PNAS*, 61(4): 1414-1421 (1968); and Takahashi N., et al., Cell, 29: 671-679 (1982)).

The antibody according to the present invention may be a human or humanized antibody.

The antibody according to the present invention may include an immunoglobulin IgG1, IgG2, IgG3, IgG4, IgA1, IgA2, IgD, IgE or IgM, and may be an antibody that binds to VEGF, or a combination or a variant thereof.

The antibody according to the present invention may be in the form of Fab, Fab', F(ab')₂, Fv, dAb, scFv or a scaffold conjugate in which CDR of the antibody is a major portion for binding to VEGF.

Also, in the present invention, there is provided a base sequence selected from a group consisting of SEQ ID NOs 66-77 encoding the light chain variable region represented by the amino acid sequence selected from a group consisting of SEQ ID NOs 54-65.

In the present invention, there is provided a base sequence selected from a group consisting of SEQ ID NOs 105-131 encoding the heavy chain variable region represented by the amino acid sequence selected from a group consisting of SEQ ID NOs 78-104.

The list of amino acids and corresponding base sequences of variable regions of the light and heavy chains of the inventive antibodies are shown in Table 2 below.

Also, in the present invention, there is provided a DNA encoding a light chain variable region of an antibody that binds to VEGF, the light chain variable region comprising CDR 2 represented by the amino acid sequence of SEQ ID NO 1; and CDR3 represented by the amino acid sequence of SEQ ID NO 2.

The DNA encoding CDR 2 represented by the amino acid sequence of SEQ ID NO 1 may be represented by the base sequence of SEQ ID NO 51; and the DNA encoding CDR 3 represented by the amino acid sequence of SEQ ID NO 2 may be represented by the base sequence of SEQ ID NO 52.

Thus, the DNA encoding the light chain variable region of the antibody of the present invention may comprise the base sequence of SEQ ID NO 51 encoding LCDR2; and the base sequence of SEQ ID NO 52 encoding LCDR3.

In the present invention, there is provided a DNA encoding a heavy chain variable region of an antibody that binds to VEGF, the heavy chain variable region comprising CDR3 represented by the amino acid sequence of SEQ ID NO 3.

The DNA encoding CDR 3 the amino acid sequence of SEQ ID NO 3 may be represented by the base sequence of SEQ ID NO 53.

The DNA encoding the heavy chain variable region of the anti-VEGF antibody may comprise the base sequence of SEQ ID NO 53 encoding HCDR3.

In the present invention, there is provided an expression vector comprising the DNA encoding the light chain variable region of the antibody, the vector expressing the light chain variable region of the antibody that binds to VEGF.

Preferably, there is provided an expression vector comprising the base sequence of SEQ ID NO 51 encoding CDR 2 represented by the amino acid sequence of SEQ ID NO 1; and the base sequence of SEQ ID NO 52 encoding CDR 3 represented by the amino acid sequence of SEQ ID NO 2.

TABLE 2

| Clones | Amino acid sequence of light chain variable regions | Base sequence of light chain variable regions | Amino acid sequence of heavy chain variable regions | Base sequence of heavy chain variable regions |
| --- | --- | --- | --- | --- |
| F | SEQ: 54 | SEQ: 66 | SEQ: 78 | SEQ: 105 |
| HF2-1 | SEQ: 55 | SEQ: 67 | SEQ: 79 | SEQ: 106 |
| HF2-2 | SEQ: 55 | SEQ: 67 | SEQ: 80 | SEQ: 107 |
| HF2-3 | SEQ: 56 | SEQ: 68 | SEQ: 81 | SEQ: 108 |
| HF2-4 | SEQ: 55 | SEQ: 67 | SEQ: 82 | SEQ: 109 |
| HF2-5 | SEQ: 55 | SEQ: 67 | SEQ: 83 | SEQ: 110 |
| HF2-6 | SEQ: 57 | SEQ: 69 | SEQ: 84 | SEQ: 111 |
| HF2-7 | SEQ: 57 | SEQ: 69 | SEQ: 85 | SEQ: 112 |
| HF2-8 | SEQ: 58 | SEQ: 70 | SEQ: 86 | SEQ: 113 |
| HF2-9 | SEQ: 57 | SEQ: 69 | SEQ: 87 | SEQ: 114 |
| HF2-10 | SEQ: 57 | SEQ: 69 | SEQ: 88 | SEQ: 115 |
| HF2-11 | SEQ: 59 | SEQ: 71 | SEQ: 89 | SEQ: 116 |
| HF2-12 | SEQ: 57 | SEQ: 69 | SEQ: 90 | SEQ: 117 |
| HF2-13 | SEQ: 60 | SEQ: 72 | SEQ: 91 | SEQ: 118 |
| HF2-14 | SEQ: 55 | SEQ: 67 | SEQ: 92 | SEQ: 119 |
| HF2-15 | SEQ: 61 | SEQ: 73 | SEQ: 93 | SEQ: 120 |
| HF2-16 | SEQ: 62 | SEQ: 74 | SEQ: 94 | SEQ: 121 |
| HF2-17 | SEQ: 62 | SEQ: 74 | SEQ: 95 | SEQ: 122 |
| HF2-18 | SEQ: 62 | SEQ: 74 | SEQ: 96 | SEQ: 123 |
| HF2-19 | SEQ: 55 | SEQ: 67 | SEQ: 97 | SEQ: 124 |
| HF2-20 | SEQ: 55 | SEQ: 67 | SEQ: 98 | SEQ: 125 |
| HF2-21 | SEQ: 57 | SEQ: 69 | SEQ: 99 | SEQ: 126 |
| HF2-22 | SEQ: 63 | SEQ: 75 | SEQ: 100 | SEQ: 127 |
| HF2-23 | SEQ: 60 | SEQ: 72 | SEQ: 101 | SEQ: 128 |
| HF2-24 | SEQ: 61 | SEQ: 73 | SEQ: 102 | SEQ: 129 |
| HF2-25 | SEQ: 64 | SEQ: 76 | SEQ: 103 | SEQ: 130 |
| HF2-26 | SEQ: 65 | SEQ: 77 | SEQ: 104 | SEQ: 131 |

Also, in the present invention, there is provided an expression vector comprising the DNA encoding the heavy chain variable region of the anti-VEGF antibody, the vector expressing the heavy chain variable region of the antibody that binds to VEGF.

Preferably, there is provided an expression vector comprising the base sequence encoding CDR 3 represented by the amino acid sequence of SEQ ID NO 3, the vector expressing the heavy chain variable region of the antibody that binds to VEGF.

The expression vector of the present invention may be transfected into an animal cell line, such as CHO cell, HEK cell or NSO cell, but not limited thereto.

Also, in the present invention, there is provided an expression vector comprising the DNA encoding the light chain variable region of the antibody, the vector expressing the light chain variable region of the antibody that binds to VEGF.

Angiogenesis refers to the formation of new capillaries arising from pre-existing capillaries. An "angiogenesis-related disease" as used herein encompasses all diseases or disorders related with angiogenesis caused by over-expression of VEGF. The "angiogenesis-related disease" may include various cancers and ophthalmic disorders etc., but is not limited thereto. In the present invention, the cancer or the angiogenesis-related disease caused by over-expression of VEGF may be selected from a group consisting of a cancer selected from a group consisting of colorectal cancer, pancreatic cancer, kidney cancer, lung cancer, breast cancer, ovarian cancer and brain cancer; an ophthalmic disorder selected from a group consisting of macular degeneration, diabetic retinopathy and ischemic retinopathy; and so on.

Anti-VEGF antibody in clinical practice may be used in combination with a drug, such as a fluoropyrimidine-based drug, paclitaxel, a platinum-based drug, interferon alpha-2a, carboplatin, and so on (FDA US BL125085 Avastin label).

The pharmaceutical composition of the present invention may also be used, in addition to the above antibody, in combination with a drug selected from a group consisting of a fluoropyrimidine-based drug, paclitaxel, a platinum-based drug, interferon alpha-2a, carboplatin, doxorubicin, cisplatin, gemcitabine, 5-fluorouracil, leucovorin, irinotecan, oxalaplatin, capecitabine, and docetaxel, but not limited thereto.

Any chemotherapeutic agent which shows anti-cancer activity may be used in combination with the pharmaceutical composition of the present invention. The chemotherapeutic agent may be selected from a group consisting of an alkylating agent, an antimetabolite, a folic acid homologue, a pyrimidine homologue, a purine homologue and related inhibitor, a vinca alkaloid, an epipodophyllotoxin, antibiotics, L-asparaginase, a topoisomerase inhibitor, interferon, a platinum coordination complex, anthracenedione-substituted urea, a methyl hydrazine derivative, an adrenocortical suppressor, an adrenocorticosteroid, progestin, estrogen, antiestrogen, androgen, antiandrogen and gonadotropin-releasing hormone homologue.

In the present invention, there is provided a diagnostic kit for cancer or an angiogenesis-related disease caused by over-expression of VEGF, the kit comprising the antibody that binds to VEGF. Examples of the angiogenesis-related diseases are described above.

Figure 2:
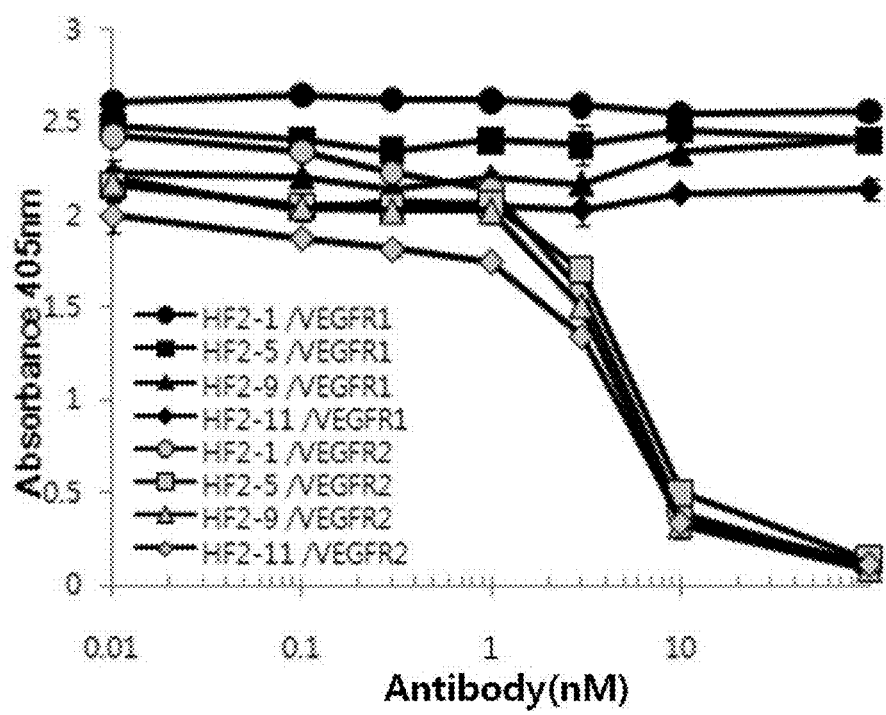
FIG. 2 is a graph showing the inhibition of the binding of VEGF with VEGFR2 by the inventive antibodies, without inhibiting the binding of VEGF with VEGFR2.
Figure 3:
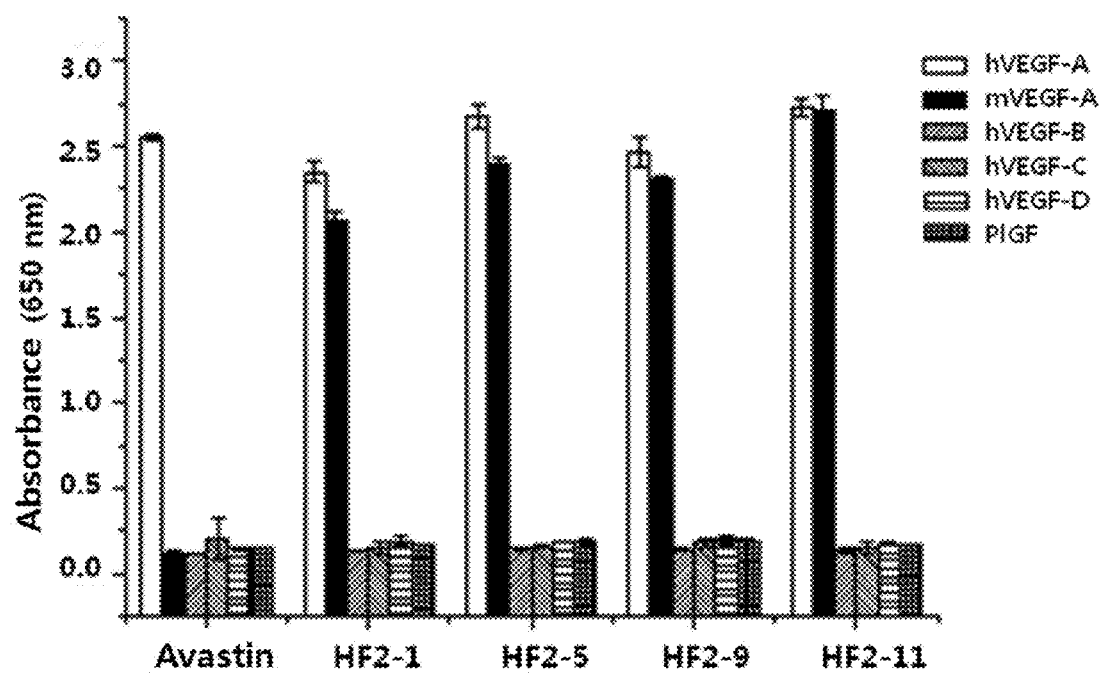
FIG. 3 is a graph showing the specific binding of the inventive antibodies with human and mouse VEGF-A.

The antibodies according to the present invention do not affect the binding between VEGF and VEGF receptor Flt-1 (VEGFR-1), but selectively inhibit the binding between VEGF and VEGF receptor KDR (VEGFR-2) (FIG. 2). Also, the antibodies do not bind to human VEGF-B, human VEGF-C, human VEGF-D or human placental growth factor (PlGF) at all, but show high binding specificity for human VEGF-A and mouse VEGF-A (FIG. 3).

Figure 8A:
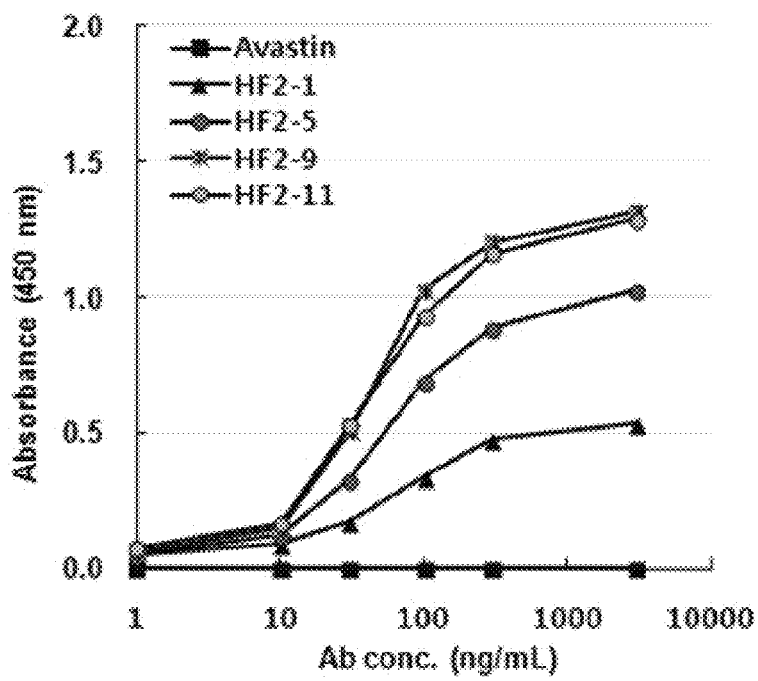
Figure 8B:
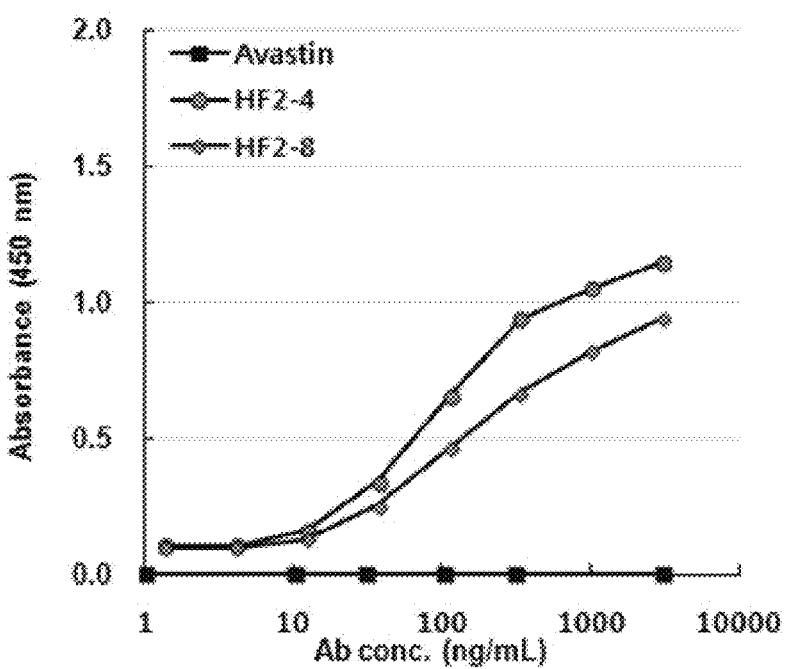

Binding affinity of the antibodies of the present invention for human vascular endothelial growth factor was assessed by Enzyme-linked immunosorbent assay (ELISA). As a result, the antibodies showed concentration-dependent binding to human VEGF (FIGS. 7(a)-7(g)). The antibodies showed excellent binding to mouse VEGF as well, in contrast to Avastin, a previously existing anti-VEGF antibody, which does not show binding to mouse VEGF, indicating that the inventive antibodies are suitable for preclinical studies using mice (FIGS. 8(a) and 8(b)).

Figure 10A:
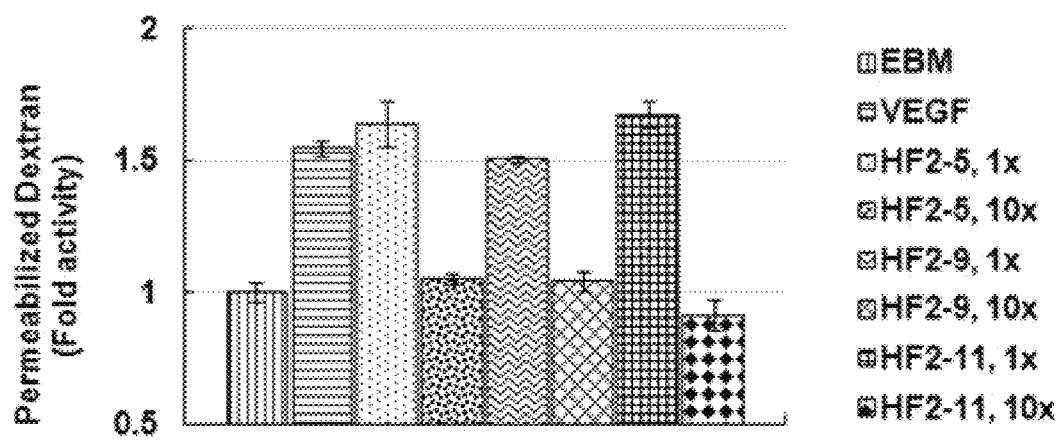
FIG. 10(a) and FIG. 10(b) show the test results of the suppression activity of the inventive antibodies (a) and Avastin (b) on the permeability of HUVEC.
Figure 10B:
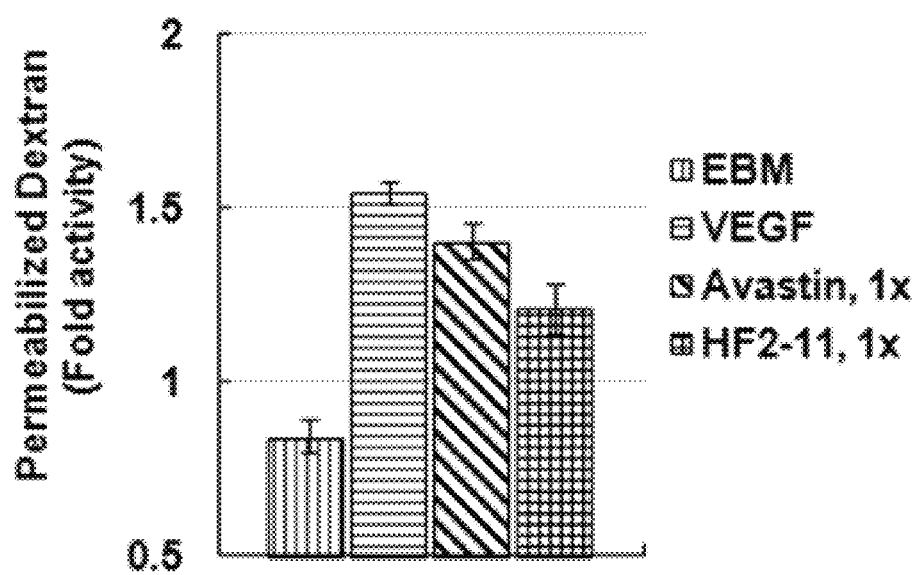
Figure 11:
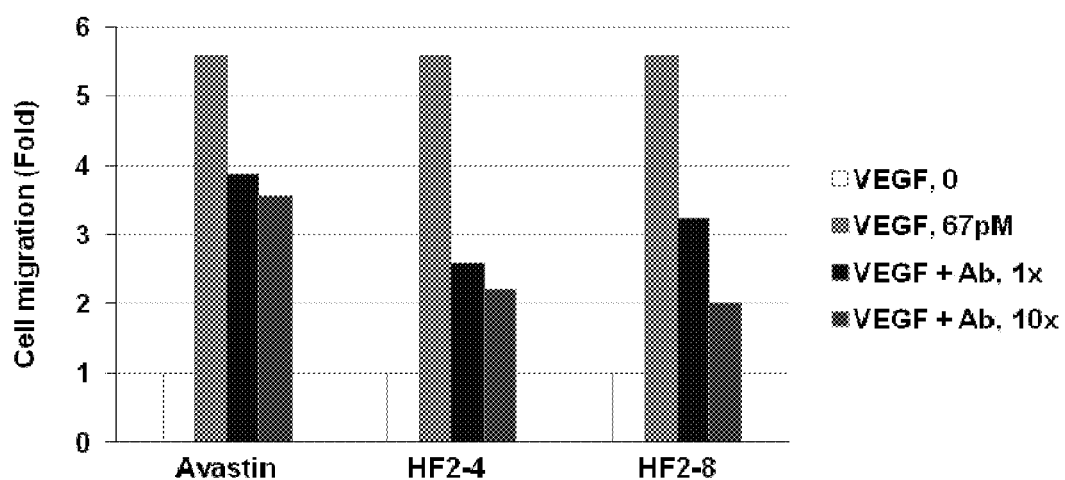
FIG. 11 shows the test results of the suppression activity of the inventive antibodies on HUVEC migration.
Figure 12A:
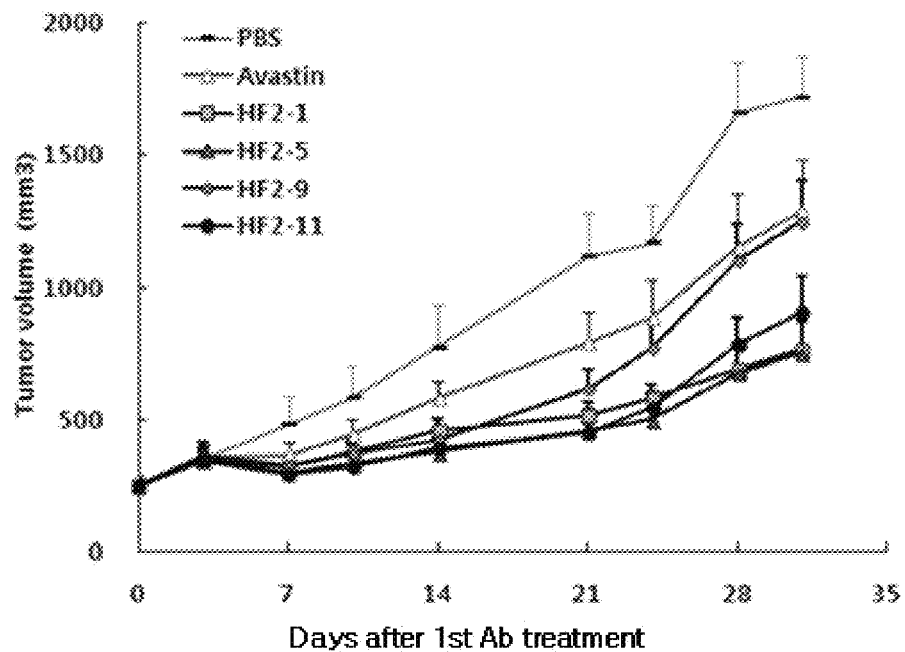
FIG. 12(a) and FIG. 12(b) show an inhibition activity of the inventive antibodies on tumor growth in HT29 implanted animal model.
Figure 12B:
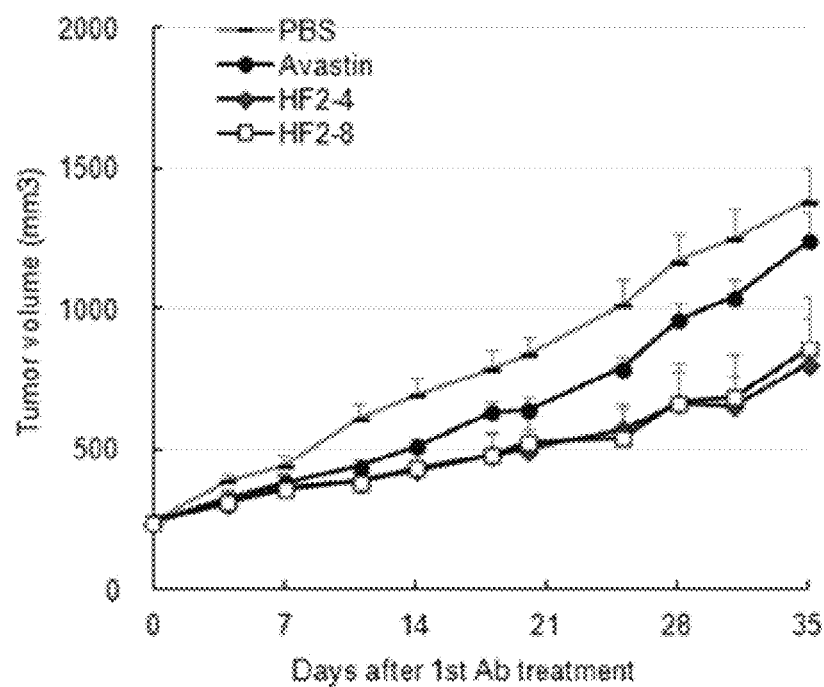
Figure 13:
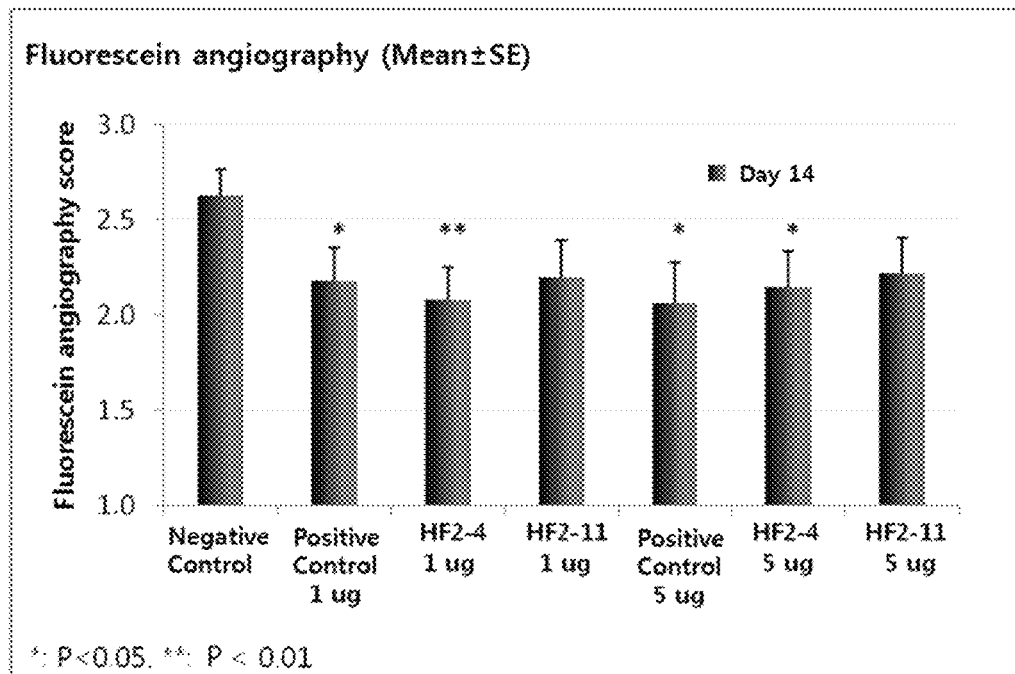
FIG. 13 shows suppression activity of the inventive antibodies on the choroidal angiogenesis.

In addition, the antibodies of the present invention suppressed the proliferation of human umbilical vein endothelial cells (HUVEC), HUVEC permeability and HUVEC migration stimulated by VEGF, to a degree equal to or higher than Avastin™ (FIGS. 9(a)-9(d), 10(a)-10(b), and 11), and suppressed tumor growth in mice implanted with a human colon cancer cell line to a degree far superior to Avastin™ (FIGS. 12(a) and 12(b)). Also the inventive antibodies significantly suppressed angiogenesis in a choroidal angiogenesis model as compared to control group (FIG. 13). As such, the human (or humanized) antibodies of the present invention may be useful for the treatment of cancer or an angiogenesis-related disease, and thus the present invention provides a composition comprising the above antibody for the prevention and treatment of cancer or an angiogenesis-related disease.

Definition

In the present invention, "VEGF" refers not only to the 165-amino acid human vascular endothelial growth factor and related 121-189- and 206-amino acid vascular endothelial growth factors, but also to a natural human vascular endothelial growth factor in allelomorphic form or modified form (see [Leung et al., Science., 246:1306 (1989); and Houck et al., Mol. Endocrin., 5:1806 (1991)]).

In the present invention, "anti-VEGF antibody" refers to an antibody which operates by way of hindering VEGF from binding to VEGF receptor to disable VEGF-activated cells, or inhibiting the activation of the vascular endothelial cell after VEGF has bound to VEGF receptor.

In the present invention, "antibody" refers to a glycoprotein that shows binding specificity to a certain antigen. A "humanized" form non-human (e.g., rodents) antibody is a chimeric antibody that includes minimal sequence derived from non-human immunoglobulin. Mostly, a humanized antibody is constructed by substituting the hypervariable region residues of mouse, rat, rabbit, chicken, or non-human primates that have desired specificity, affinity and capability for the hypervariable region residues of human immunoglobulin. In some cases, frame work region (FR) residue of human immunoglobulin is replaced with corresponding non-human residue.

In the present invention, "single chain Fv" or "scFv" antibody fragment includes $V_H$ and $V_L$ domains of an antibody that exist in a single polypeptide chain. Generally, Fv polypeptide further includes a polypeptide linker between $V_H$ and $V_L$ domains which helps scFv to form an appropriate structure for the binding with an antigen.

In the present invention, "Fab antibody fragment" is a fragment obtained by digesting an antigen with the protease papain, in which $V_H$ and $V_L$ domain, and $CH_1$ and CL domain of the antibody are connected by S—S bond, and which has an antigen binding function.

In the present invention, "F(ab')₂ antibody fragment" refers to the portion of an antibody excluding Fc (CH₂ and CH₃) fragment. It can be constructed by the cleavage of an antibody below its hinge region.

In the present invention, "Fab'" is in the form of F(ab')₂ antibody fragment with the hinge region cut off; and has two —SH groups.

In the present invention, "Fv" refers to a variable region of an antibody, and "dAb" refers to single domain antibody fragment.

In the present invention, "VEGF receptor" refers to a cellular receptor for VEGF, generally, a cell surface receptor or its variant having the capability of binding with hVEGF. One example of VEGF receptor is transmembrane receptor in tyrosine kinases, particularly, fms-type tyrosine kinase (flt) (see [DeVries et al., *Science.*, 255:989 (1992); Shibuya et al., *Oncogene.*, 5; 519 (1990)]). Flt receptor includes extracellular domain, transmembrane domain, and intracellular domain that has tyrosine kinase activity. While the extracellular domain is related to VEGF binding, the intracellular domain is related to signal transduction. Another example of VEGF receptor is flk-1 receptor (hereinafter referred to as "KDR") (see [Matthews et al., *Proc. Nat. Acad. Sci.*, 88:9026 (1991); Terman et al., *Oncogene.*, 6:1677 (1991)).

Hereinafter, the present invention will be described in more detail with the following Examples. The following Examples are provided to illustrate the present invention, but the scope of the present invention is not limited thereto.

Example 1. VEGF Immunization and cDNA Library Construction

In order to select antibodies that specifically bind to VEGF, an antibody library was constructed from immunized animals. The library was constructed by obtaining mRNA from immune cells of animals immunized with antigen, amplifying antibody genes by PCR using a primer combination for the antibody genes, and cloning the genes into a vector for phage display.

Specifically, human VEGF and mouse VEGF (R&D Systems, USA) were mixed with complete Freund's adjuvant and incomplete Freund's adjuvant (Sigma, USA), and the mixture thereof was subcutaneously injected into three white Leghorn chickens 5 times at 3-week intervals. The sera of immunized animals were obtained, diluted at 1:100, 1:500, 1:2500 and 1:12500 using PBSB (phosphate buffer containing 3% bovine serum albumin) and stored, then their bindings with human VEGF and mouse VEGF were assessed by enzyme immunoassay. To ELISA plates, 0.2 μg/mL each of human VEGF (VEGF-165, R&D Systems, USA) and mouse VEGF (VEGF-164, R&D Systems, USA) were respectively coated overnight at 4° C., and then the sera diluted above were added, and allowed to react for 2 hr. After washing 3 times with PBST (PBS containing 0.1% tween-20), anti-chicken immunoglobulin-horse radish peroxidase (HRP) (1:3000) was added and allowed to react for 1 hr. After washing 3 times with PBST, ultra-TMB (Thermo, USA) was added and allowed to develop for 7 minutes, and the absorbance at 650 nm was measured using a microplate reader. Pre-immunization sera did not bind to VEGF, and animals producing sera which strongly bound to both human and mouse VEGF were selected.

5 days after the last injection, bone marrow, spleen and bursa of Fabricius tissues were collected from the selected chickens. The tissues were mixed with 10 mL of TRI reagent (Molecular Research Center, USA), homogenized, and after addition of 20 mL of TRI reagent centrifuged to obtain supernatant. After addition of 3 mL of 1-bromo-3-chloropropane (BCP), supernatant was obtained following centrifugation. Total RNA was precipitated by treatment with 15 mL of isopropanol. A reverse transcription reaction (65° C. for 5 min; 4° C. for 5 min; 50° C. for 50 min; 85° C. for 5 min; and 4° C.) was carried out using Super Script transcription system (Invitrogen, USA) and random hexamer as a primer. 5 μL of a reaction solution, containing cDNA resulting from the reverse transcription reaction, was loaded to 1% agarose gel and electrophoresis was carried out, and cDNA bands with various lengths were verified.

Example 2. Construction of Antibody Library (2-1) Amplification of Immune Antibody Gene To amplify the variable regions of heavy and light chains of chicken antibody ($V_H$ and $V_L$ domains), PCR reactions were carried out as follows.

The PCR reactions were performed using cDNAs prepared in Example 1 as templates, and the primer combination of Table 3 designed for $V_H$ and $V_L$ and single chain Fv (scFv) connecting the $V_H$ and $V_L$. 0.5 μL each of cDNA libraries of $V_H$ and $V_L$, 30 pmole of forward primer, 30 pmole of reverse primer, 10×PCR buffer, 200 μM dNTPs and 0.5 μL of Taq DNA polymerase were mixed to a final volume of 50 μL. The mixture was reacted at 94° C. for 5 min, then repeatedly reacted at 94° C. for 15 sec, 56° C. for 30 sec and 72° C. for 90 sec for 30 cycles.

TABLE 3

Primer used in PCR reaction

| Primer | | Sequence | SEQ ID NO |
|---|---|---|---|
| $V_H$ | Forward | GGT CAG TCC TCT AGA TCT TCC GGC GGT GGT GGC AGC TCC GGT GGT GGC GGT TCC GCC GTG ACG TTG GAC GAG | 132 |
| | Reverse | CTG GCC GGC CTG GCC ACT AGT GGA GGA GAC GAT GAC TTC GGT CC | 133 |
| $V_L$ | Forward | GTG GCC CAG GCG GCC CTG ACT CAG CCG TCC TCG GTG TC | 134 |
| | Reverse | GGA AGA TCT AGA GGA CTG ACC TAG GAC GGT CAG G | 135 |
| scFv | Forward | GAG GAG GAG GAG GAG GAG GTG GCC CAG GCG GCC CTG ACT CAG | 136 |
| | Reverse | GAG GAG GAG GAG GAG GAG GAG CTG GCC GGC CTG GCC ACT AGT GGA GG | 137 |

PCR-amplified antibody DNAs were electrophoresed on 1% agarose gel, to separate each of the amplified DNAs according to size, and purified using Gel extraction kit (Qiagen, USA).

To obtain scFv DNA, 50 ng each of the purified $V_H$ and $V_L$ DNAs was used as a template, which was mixed with 30 pmole of a forward primer and 30 pmole of a reverse primer (Table 3), 10×PCR buffer, 200 μM dNTPs and 0.5 μL of Taq DNA polymerase to a final volume of 50 μL. The mixture was subjected to a PCR reaction at 94° C. for 5 min followed by 20 cycles of 94° C. for 30 sec, 56° C. for 30 sec and 72° C. for 2 min. PCR-amplified antibody DNAs were electrophoresed on 1% agarose gel to separate each of the amplified DNAs according to size, which was then purified using Gel extraction kit (Qiagen, USA).

(2-2) Cleavage of Antibody DNA by Restriction Enzyme

The scFv prepared above and a phagemid vector, pComb3X (the Scripps Research Institute, CA, USA), were cleaved by restriction enzyme SfiI (Roche, USA).

10 μg of PCR fragments encoding scFv, 360 units of SfiI (Roche, USA) and 20 μg of 10× buffer were mixed to a final volume of 200 μL and reacted overnight at 50° C.

In addition, 20 μg of pComb3X vector, 120 units of SfiI and 20 μL of 10× buffer were mixed to a final volume of 200 μL and reacted overnight at 50° C. The fragments obtained by the restriction enzyme cleavage were electrophoresed, and then purified using Gel extraction kit (Qiagen, USA).

(2-3) Ligation of Antibody DNA and Preparation of Library

In order to insert the scFv fragment into the pComb3X vector, 700 ng of PCR fragments encoding scFv which was cleaved in the (2-2) using SfiI, and 1.4 μg of pComb3X were mixed. After addition of T4 DNA ligase (Invitrogen, USA), the mixture was reacted overnight at 16° C. The ligation mixture was purified by ethanol precipitation. Then, E. coli ER2738 (New England Biolab, USA) was transformed with the mixture by electroporation, and cultured in the presence of 46 μg/mL carbenicilline and 70 μg/mL kanamycin, to prepare a library with the complexity of 1.5×10$^9$.

Example 3. Selection of Phage Clone Containing Anti-VEGF scFv

From the library containing randomized heavy and light chains in scFv form obtained in the Example 2, antibodies that bind to both human and mouse VEGF were selected using solid-immobilized VEGF.

(3-1) Selection of the Antibody that Binds to VEGF

First, 10 ug each of human VEGF (R&D systems, USA) and mouse VEGF (R&D systems, USA) were conjugated to magnetic beads.

The antibody library DNA obtained in the Example 2, which was constructed such that the antibody in the scFv form is displayed in a fused form with phage coat protein PIII, was transfected into E. coli ER2738 (New England Biolab) by electroporation, which was then cultured at 37° C. After addition of VCSM13 helper phage (Stratagene, USA), 46 ug/ml of carbenicillin and 70 ug/ml of kanamycin were further added, followed by culturing overnight in SB culture medium (30 g/L tryptone, 20 g/L yeast extract, and 10 g/L MOPS, pH 7.0).

The culture medium obtained above, containing the E. coli and phages, was centrifuged to remove the E. coli pellet. After recovering the supernatant, 40 mg/ml of polyethylene glycol 8000 and 30 mg/ml of NaCl was added, followed by centrifugation, to collect PEG-precipitaed phages, which were resuspended in PBS.

Human or mouse VEGF conjugated to the magnetic beads were reacted with the phages at room temperature for 2 hr to allow phages having affinity for VEGF to bind, then the resultant sample was washed with PBS containing 0.5% Tween 20, eluted with 0.1M Glycine (pH 2.2), and neutralized with 2M tris solution. For the next round of panning, eluted phages were infected to E. coli ER2738 and cultured overnight. Panning was carried out by repeating this process 4 times.

The number of washing was increased with increasing cycles of panning, resulting in accumulation of phages with high binding affinity. To find binders to both human and mouse VEGF, human VEGF only or alternating human and mouse VEGF were used as antigens.

Individual clones selected from each of the 4th panning output were cultured overnight in 96 deep well plates in the presence of 100 ug/ml of carbenicillin, 70 ug/ml of kanamycin, and VCSM13 helper phage (1:1000), inducing the proliferation of phages which expressed antibodies.

The culture broth thus obtained was centrifuged to acquire culture supernatant containing phages. The acquired supernatant was added to ELISA plate coated with VEGF and incubated at 37° C. for 2 hr. VEGF-binding antibodies were identified by ELISA using HRP-conjugated anti-M13 antibody as a secondary antibody.

(3-2) Sequencing of the Selected Antibody

The ER2738 which contains clones showing positive signals to both human and mouse VEGF, selected in Example 3-1, was cultured overnight in SB culture medium and centrifuged to obtain E. coli. DNA mini-prep kit (Gene-All, Korea) was used to obtain plasmid DNA and its base sequence was analyzed. The sequencing primers shown in Table 4 (SEQ ID NOs 138 and 139) were used to determine the base sequence. The selected clone was named "clone F." The detailed base sequence information of clone F antibody is shown in the Table 1.

TABLE 4

| | |
|---|---|
| Forward (SEQ ID NO 138) | ACA CTT TAT GCT TCC GGC TC |
| Reverse (SEQ ID NO 139) | CAA AAT CAC CGG AAC CAG AG |

Example 4. Humanization and Affinity Improvement

The framework of antibody clone F obtained from animal immunized antibody library was converted to human antibody framework, while some residues important for antigen binding were not changed (Nishibori et al., *Molecular Immunology*, 43 (2006)).

For the affinity improvement, the CDR sequences of the heavy chain and light chain were randomized to produce a new phage library. By the same method shown in the Example 2, the obtained phage library was reacted with 10 μg of human VEGF immobilized to magnetic bead at room temperature for 2 hr and washed with PBS containing 0.5% Tween 20 for 5 times. After washing, the phages which were bound to antigens were eluted with 0.1M Glycine (pH 2.2) solution and neutralized with 2M tris solution. At the 2nd panning, the sample was washed with PBS containing Tween 20 for 10 times, and at the 3rd panning, it was washed with PBS containing Tween 20 for 20 times, to increase the selection pressure.

The variant clones of clone F which went through the above process were named "HF2-1 to HF2-26", and their binding affinity was verified through ELISA and BIAcore. As a result, it was confirmed that the antibodies obtained from the above process bound to human and mouse VEGF with an affinity at least 10 times higher than mother clone F, with some of the clones showing at least 100 times higher affinity.

Example 5. Production of Antibodies

For the affinity measurement and activity analysis of the obtained antibody above, scFv or immunoglobulin (IgG) protein was produced.

For scFv protein production, E. coli HB2151 was transformed with pComb3X plasmid containing DNA of the selected clone, followed by purification of the expressed scFv.

Specifically, 1 mM of isopropyl β-D-1-thio galactopyranoside (IPTG) was added when the O.D. value reached 1, followed by overnight culture at 37° C. Then E. coli and culture medium were separated by centrifugation. In order to purify scFv, scFv protein was bound to nickel NTA column (GE, USAA.), which binds to C-terminal His tag, eluted with 250-300 mM of imidazole solution, and dialyzed in PBS buffer overnight.

For IgG production, fragments of variable and constant regions of the heavy and light chains were obtained from pComb3x containing scFv by conducting PCR using the condition in Example 2 and primer combinations shown in Table 5.

Heavy chains and light chain variable and constant regions ($C_H$ and $C_k$) were obtained by conducting PCR using the HC and LC primer combinations in Table 5, and transferred to mammalian cell expression plasmid using the pcDNATM3.3-TOPO® TA cloning kit and pOptiTMVEC-TOPO® TA cloning kit (Invitrogen, USA). 1 µL of each vector (pcDNATM3.3-TOPO® vector and pOptiTM VEC-TOPO® vector) and the fragments were added to a buffer containing 200 mM of NaCl and 10 mM of $MgCl_2$ to a total volume of 6 µL, and reacted for 5 min at room temperature. DH 5a E. coli competent cells were transformed by applying a heat shock, and the colonies thus obtained were cultured at large scale to obtain plasmids.

The plasmids prepared above were transfected to HEK293F cell (Invitrogen, USA), and the antibodies obtained after 7 days of culture were purified using a protein A column (GE, USA). Culture medium was loaded to the column to allow the antibodies (IgG) in the culture medium to bind to protein A. The antibodies were then eluted with 20 mM of sodium citrate buffer (pH 3.0). Agreement of molecular weights of light and heavy chains with the theoretically calculated values, and a high degree of purity were confirmed by SDS-PAGE.

Example 6. Measurement of Binding Affinity

ELISA plates were coated with 0.2 µg/ml of human VEGF and mouse VEGF (R&D systems, USA) respectively, and the purified proteins obtained in Example 5 in the form of scFv expressed by HB2151 or IgG expressed by 293F cells were incubated at serially diluted concentrations. As a result, the clone F obtained in the Example 3-2, and its variants obtained by affinity improvement showed good binding to human and mouse VEGF in a concentration-dependent manner.

Meanwhile, to measure the affinity, human VEGF and mouse VEGF were coupled to carboxymethylated dextran biosensor chips (CM5, GE) according to the manufacturer's instructions. For the measurement of association and dissociating rates, IgG protein was serially diluted 2-fold to 5 nM, 2.5 nM, 1.25 nM, 0.625 nM, 0.313 nM, and 0.156 nM and injected.

The association and dissociation rates were expressed by the association and dissociation sensorgram, and calculated using a simple 1:1 Langmuir binding model (BIAcore X100 evaluation software, ver. 2.0). Equilibrium dissociation constant (KD), calculated as the dissociation rate constant (Kd) divided by associate rate constant (Ka), was confirmed to be at sub-nanomolar levels indicating high affinity. Measured values for antibodies HF2-1 to HF2-11, HF2-13, and HF2-14 against human VEGF (hVEGF) are shown in Table 6, and the sensorgram of HF2-11 is shown in FIG. 1 as a representative example.

TABLE 6

| Clones | Binding molecule | Ka(1/Ms) | Kd(1/s) | KD(M) |
|---|---|---|---|---|
| HF2-1 | hVEGF | $2.5 \times 10^6$ | $<1 \times 10^{-6}$ | $<1 \times 10^{-12}$ |
| HF2-2 | hVEGF | $1.1 \times 10^6$ | $<1 \times 10^{-6}$ | $<1 \times 10^{-12}$ |
| HF2-3 | hVEGF | $1.3 \times 10^6$ | $<1 \times 10^{-6}$ | $<1 \times 10^{-12}$ |
| HF2-4 | hVEGF | $1.6 \times 10^6$ | $3.1 \times 10^{-6}$ | $1.9 \times 10^{-12}$ |
| HF2-5 | hVEGF | $1.3 \times 10^6$ | $2.6 \times 10^{-5}$ | $1.9 \times 10^{-11}$ |
| HF2-6 | hVEGF | $1.6 \times 10^6$ | $<1 \times 10^{-6}$ | $<1 \times 10^{-12}$ |
| HF2-7 | hVEGF | $1.6 \times 10^6$ | $2.7 \times 10^{-5}$ | $1.6 \times 10^{-11}$ |
| HF2-8 | hVEGF | $1.5 \times 10^6$ | $5.7 \times 10^{-5}$ | $3.6 \times 10^{-11}$ |
| HF2-9 | hVEGF | $1.7 \times 10^6$ | $3.2 \times 10^{-5}$ | $1.8 \times 10^{-11}$ |
| HF2-10 | hVEGF | $1.6 \times 10^6$ | $<1 \times 10^{-6}$ | $<1 \times 10^{-12}$ |
| HF2-11 | hVEGF | $1.4 \times 10^6$ | $6.8 \times 10^{-6}$ | $4.7 \times 10^{-12}$ |
| HF2-13 | hVEGF | $1.4 \times 10^6$ | $1 \times 10^{-5}$ | $9.0 \times 10^{-12}$ |
| HF2-14 | hVEGF | $1.3 \times 10^6$ | $<1 \times 10^{-6}$ | $<1 \times 10^{-12}$ |

TABLE 5

| Primer | | Sequence | SEQ ID NO |
|---|---|---|---|
| $V_H$ | Forward | GCT AGC CGC CAC CAT GGG C | 140 |
| | Reverse | AGG GGC CCT TGG TGG AGG CCT GGC CGG CCT GGC CAC T | 141 |
| $C_H$ | Forward | GCC TCC ACC AAG GGC CCC TC | 142 |
| | Reverse | CGG GAT CCC TTG CCG GCC GT | 143 |
| HC | Forward | GCT AGC CGC CAC CAT GGG C | 144 |
| | Reverse | CGG GAT CCC TTG CCG GCC GT | 145 |
| $V_L$ | Forward | AAG CTT GCC GCC ACC ATG | 146 |
| | Reverse | AGG GGG CGG CCA CGG TCC GGG AAG ATC TAG AGG ACT G | 147 |
| $C_k$ | Forward | CGG ACC GTG GCC GCC CCC TC | 148 |
| 역방향 | | GCT CTA GAC TAG CAC TCG C | 149 |
| LC | Forward | AAG CTT GCC GCC ACC ATG | 150 |
| | Reverse | GCT CTA GAC TAG CAC TCG C | 151 |

Example 7. Verification of Inhibition on Ligand-Receptor Binding

To verify the inhibition effects of the selected antibodies (HF2-1, HF2-5, HF2-9 and HF2-11) of the present invention on the binding of VEGF with VEGF receptor KDR (hereinafter, VEGFR2) or VEGF receptor Flt-1 (hereinafter, VEGFR1), experiments were conducted as follows.

0.5 μg/ml of human VEGF was coated to 96-well ELISA plate and blocked with PBS solution containing 3% BSA and 0.05% Tween 20. To each well, 6 nM of Flt-1 ECD IgG Fc fusion protein (27-687, R&D systems, USA) or 9 nM of KDR ECD IgG-Fc fusion protein (R&D systems, USA) was added together with each of the antibodies HF2-1, HF2-5, HF2-9, and HF2-11 diluted 2-fold (0.01 nM, 0.1 nM, 0.3 nM, 1 nM, 3 nM, 10 nM, and 100 nM), and incubated for 1 hr at 37° C. Flt-1 ECD IgG-Fc fusion proteins and KDR ECD IgG-Fc fusion proteins which bound despite inhibition by the antibodies were detected using anti-human IgG-Fc antibody-HRP conjugate (Jackson Immunoresearch, USA) followed by ABTS chromogenic development and measurement of absorbance at 405 nm.

As a result, as shown in FIG. 2, the antibodies of the present invention inhibited the binding of VEGF with KDR (VEGFR2) in a concentration-dependent manner, but did not inhibit the binding of VEGF with Flt-1 (VEGFR1). Thus, the selected antibodies of the present invention were confirmed to selectively inhibit the binding of VEGF with VEGF receptors.

Example 8. Verification of Binding Specificity

To measure the binding specificity of selected antibodies HF2-1, HF2-5, HF2-9, and HF2-11 of the present invention to human VEGF-A (hVEGF-A), mouse VEGF-A (mVEGF-A), human VEGF-B (hVEGF-B), human VEGF-C (hVEGF-C), human VEGF-D (hVEGF-D) and human placental growth factor (PlGF), experiments were conducted as follows.

0.2 μg/ml each of the respective proteins (hVEGF-A, mVEGF-A, hVEGF-B, hVEGF-C, hVEGF-D and PlGF) (R&D systems) were coated to the wells of ELISA plate, respectively. After blocking them with PBS containing 3% BSA and 0.05% Tween 20 for 30 min at 37° C., antibody clone proteins of increasing concentrations were incubated at 37° C. for 2 hr. Then, the wells were washed with PBS containing 3% BSA and 0.05% Tween 20 for 3 times, and anti-human IgG-Fab-HRP conjugate (Jackson Immunoresearch, USA) was added thereto and incubated for 1 hr at room temperature. Then they were washed with PBS containing 3% BSA and 0.05% Tween 20 for 3 times, and developed using TMB, and absorbance was measured at 650 nm. Avastin™ (Roche, Switzerland) was used as a control.

As shown in FIG. 3, the antibody clones of the present invention showed good binding to hVEGF-A and mVEGF-A, but did not bind to VEGF-B, VEGF-C, VEGF-D or PlGF at all, indicating high specificity for VEGF.

Example 9. Analysis of Physicochemical Characteristics

The physicochemical characteristics of antibodies of the present invention were analyzed.

Using NuPAGE 4-12% Bis-Tris gel (Invitrogen Co.), SDS-polyacrylamide gel electrophoresis (SDS-PAGE) analysis under reducing conditions in the presence of DTT to remove disulfide bonds, and under non-reducing condition in the absence of DTT processing, confirmed the existence of light and heavy chains of the whole antibody. The molecular weight measurement results of HF2-11 are shown in FIG. 4 as a representative example.

Figure 4:
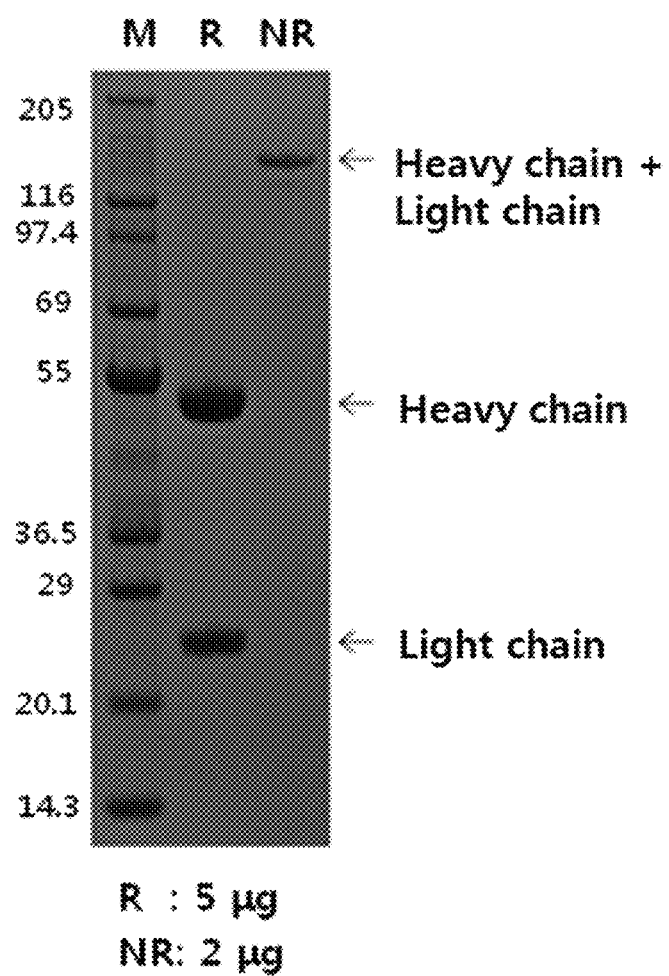
FIG. 4 shows the SDS-PAGE results of HF2-11 clone.

As shown in FIG. 4, the specimens analyzed under non-reducing condition (NR, 5 μg) showed 1 principal band between the 116 kDa size marker and 205 kDa size marker, confirming the existence of a band corresponding to the size of a whole antibody. Specimens analyzed under reducing condition (R, 2 μg) showed principal bands around 55 kDa and 20.1 kDa size marker, respectively, confirming the existence of bands corresponding to the heavy and light chains of antibody. Thus, the bands corresponding to the whole antibody, heavy chain, and light chain were identified by SDS-PAGE, and no other major impurity bands were found.

Figure 5A:
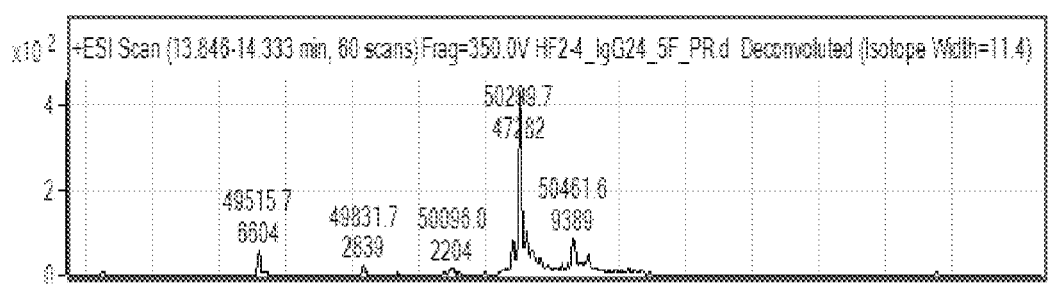
FIG. 5(a) and FIG. 5(b) show the mass analysis results of the heavy chain (a) and light chain (b) of the antibody HF2-4.
Figure 5B:
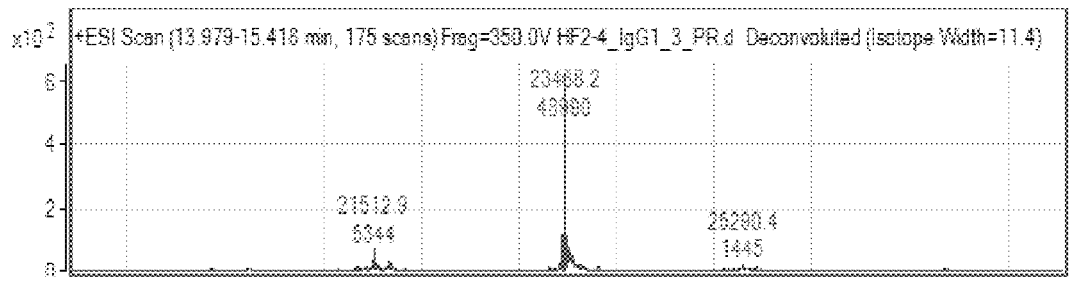

Also, the molecular weight of HF2-4 and its agreement with the value estimated from the theoretical amino acid sequence was confirmed using the liquid chromatography/mass spectrometry (LC/MS). The mass analysis results of heavy and light chains of HF2-4 are shown in FIG. 5 (a) and (b) as a representative example.

After partially reducing the specimens, the mass of heavy and light chains were analyzed. The heavy chain showed a major peak of 50.6 kDa size and the light chain of 23.3 kDa size, which were in agreement with the estimated molecular weight values. Also, small peaks which seem to be the result of post-translational modification such as glycosylation were observed.

Figure 6:
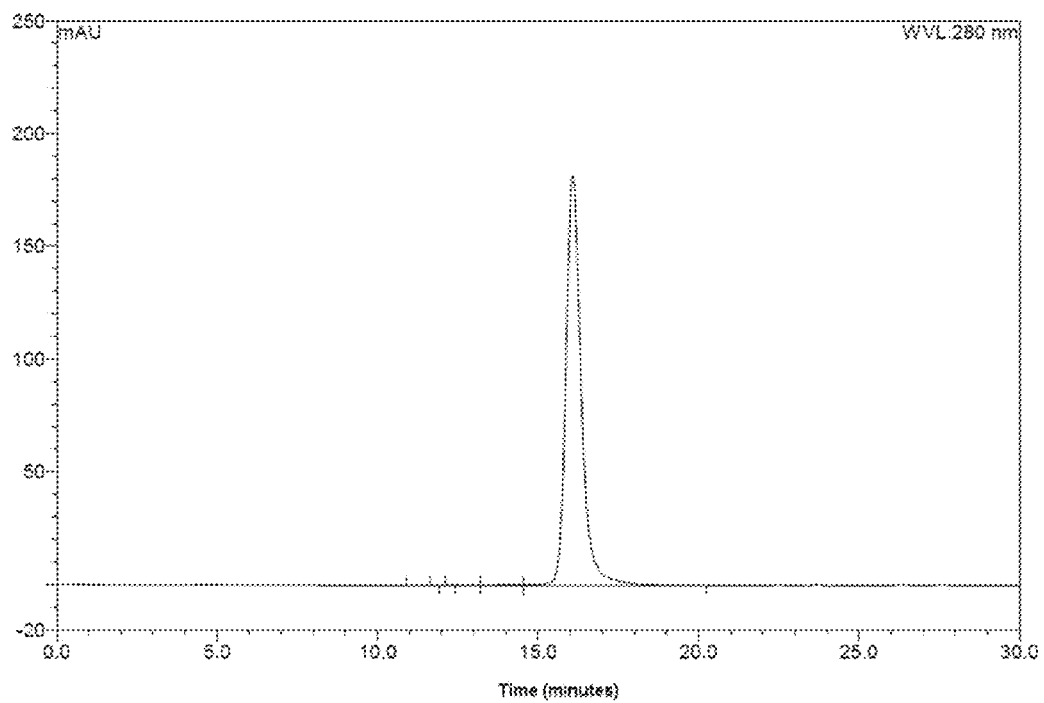
FIG. 6 shows the results of size exclusion chromatography (SEC) of the HF2-8 clone.
Figure 7:
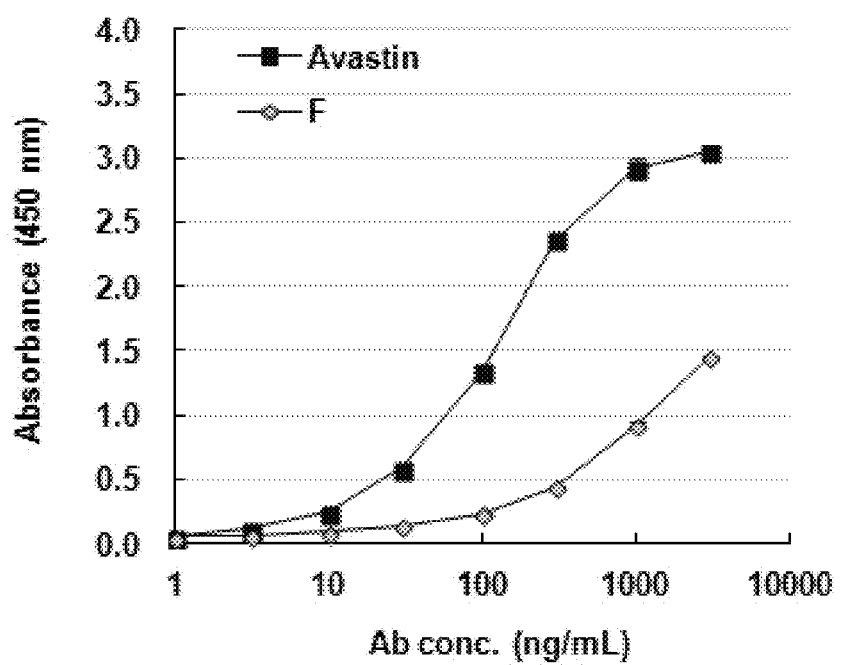
FIG. 7(a), FIG. 7(b), FIG. 7(c), FIG. 7(d), FIG. 7(e), FIG. 7(f), FIG. 7(g), FIG. 8(a), and FIG. 8(b) show the results of measurement by ELISA of the binding property of the inventive antibodies and Avastin to human and mouse VEGF antibodies.
Figure 7B:
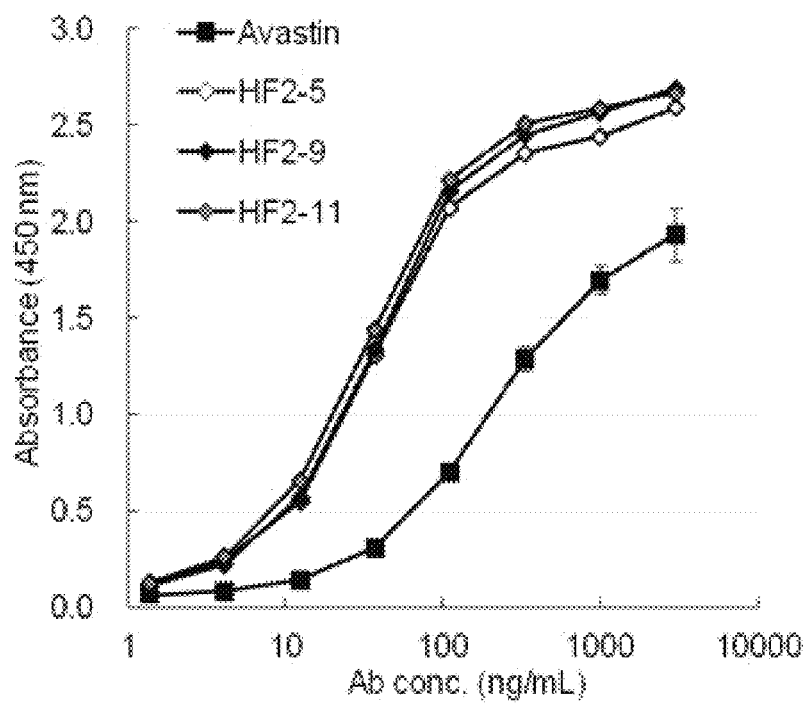
Figure 7C:
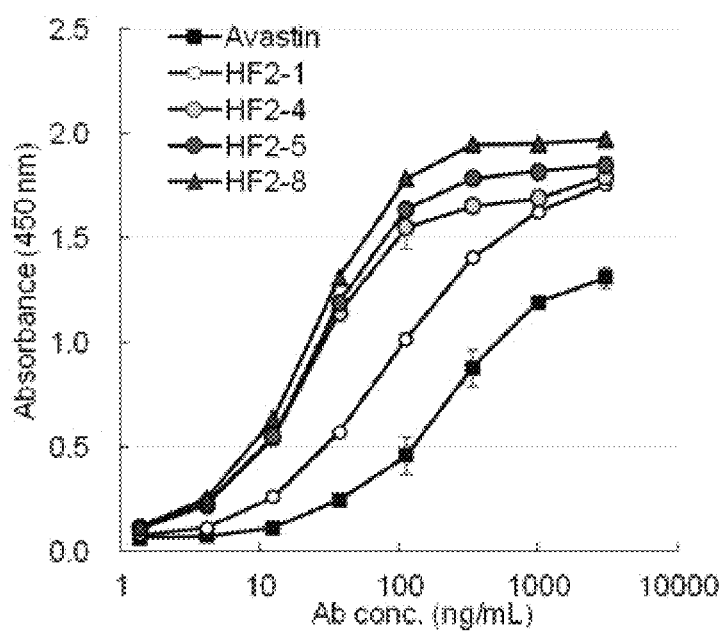
Figure 7D:
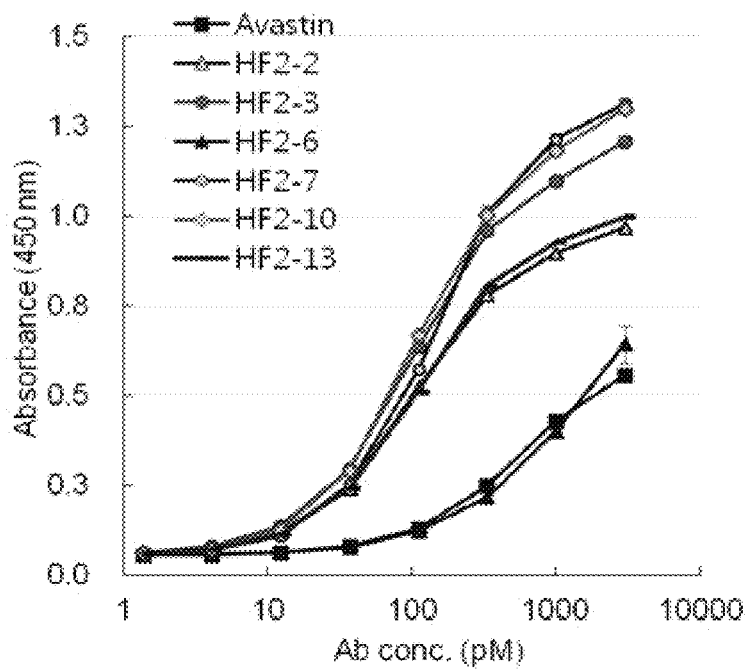
Figure 7E:
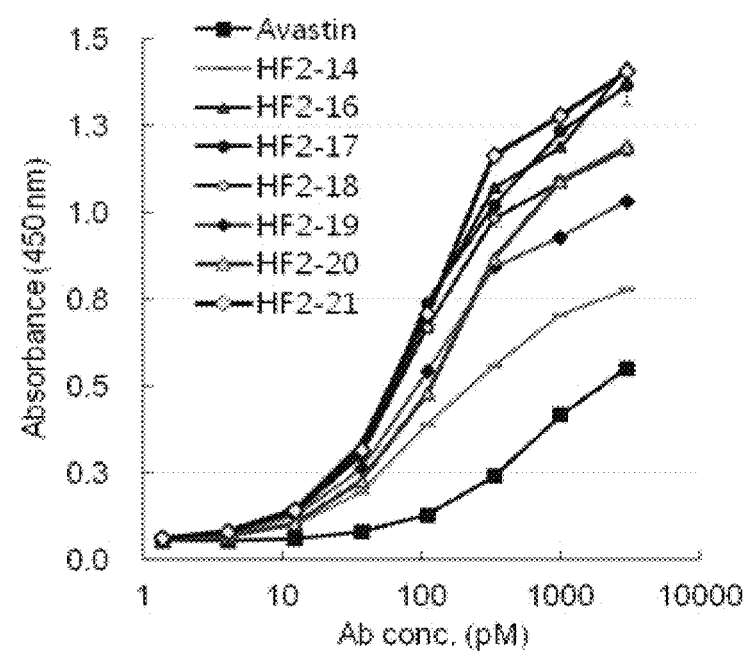
Figure 7F:
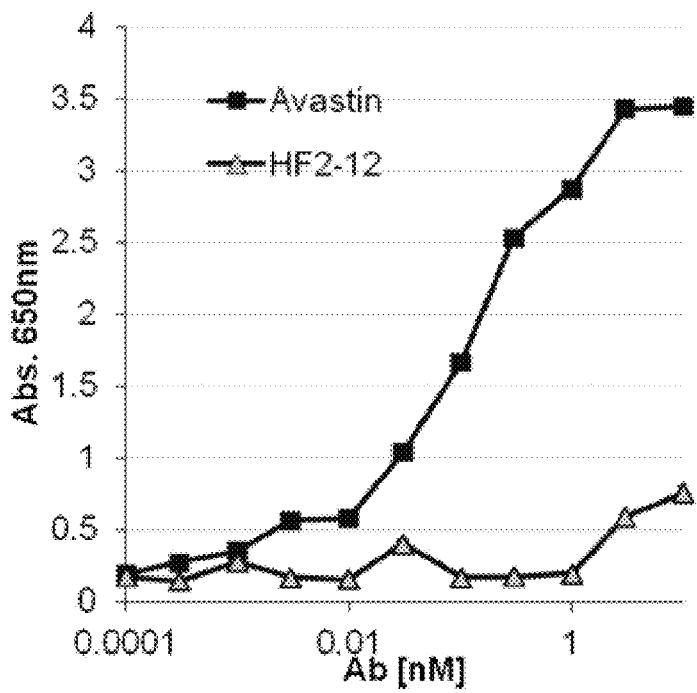
Figure 7G:
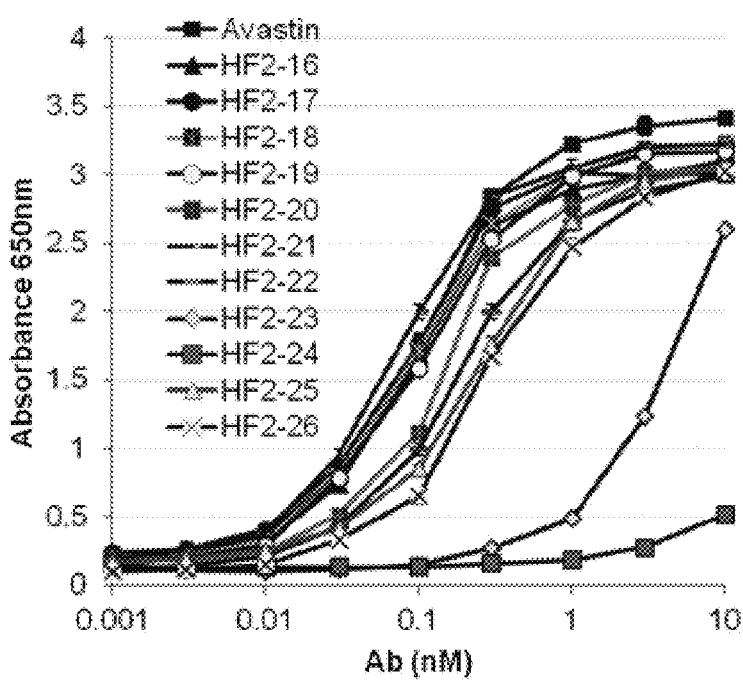

In addition, the aggregation state (i.e. soluble aggregates, a type of impurities) of antibody HF2-8 of the present invention was analyzed by size exclusion chromatography (SEC) using TSKgel G3000SWxl column (Tosoh Co.), and the results are shown in FIG. 6. Using separation by isocratic elution with 100 mM phosphate buffer (pH6.6) as the mobile phase and monitoring at 280 nm, monomer peak area was observed to be 98% or more of the total peak area, whereas the peak area of aggregates occupied less than 2%, indicating high purity.

Example 10. Analysis of Antibody Binding to Human or Mouse VEGF

The binding property of the antibodies of the present invention (HF2-1 to HF2-26) to human vascular endothelial growth factor (VEGF) was verified using ELISA method.

1.5 ng of human VEGF diluted in 150 μL of buffer solution was placed in 96-well immune plate (Nunc, USA), and adsorbed at 4° C. overnight, followed by washing 3 times with a buffer solution containing 0.1% Tween 20. Then, they were reacted with a buffer solution including 1% bovine serum albumin (Sigma, USA) for 1 hr at room temperature, and washed 3 times. Then each well was treated with 150 μL of serially diluted antibody (1 ng/mL, 10 ng/mL, 30 ng/mL, 100 ng/mL, 1000 ng/mL and 3000 ng/mL) They were allowed to react for 1 hr at room temperature so that antigens may bind to antibodies, followed by washing 3 times with a buffer solution.

Each well was treated at 150 μL per well with anti-human immunoglobulin Fc-HRP antibody (AbSerotec, USA) diluted 1:20000 and allowed to react for 1 hr at room temperature. After the reaction was completed, washing was performed 3 times with a buffer solution, followed by addition of 150 μL of TMB (Sigma, USA) and color development for 10 min. The reaction was terminated with 1N sulfuric acid solution, and absorbance was measured at 450 nm using a spectrophotometer (Molecular Device, USA). The results are shown in FIGS. 7(a)-7(g). Avastin™ was used as the control group, whose absorbance was measured in the same manner.

As shown in FIGS. 7(a)-7(g), it was confirmed that the binding property of HF clones (b), which are humanized clones of clone F (a), was increased through the affinity improvement process. It was found that most of these HF clones (HF2-1 to HF2-26) showed higher binding property to VEGF than Avastin™.

The binding property of the antibodies to mouse VEGF was verified by ELISA in the same manner as described above. The results shown in FIGS. 8(a) and 8(b) indicate that, unlike Avastin™, the inventive antibodies HF2-1, HF2-5, HF2-8, and HF2-9 bind to mouse VEGF as well as human VEGF, indicating that the antibodies of the present invention are suitable for pre-clinical studies using mice.

Example 11. Confirmation of Suppression Activity of the Inventive Antibodies on VEGF-Induced HUVEC Proliferation The suppression activity of the inventive antibodies on VEGF-induced HUVEC proliferation was confirmed.

A pellet was obtained by centrifuging human umbilical vein endothelial cells (HUVEC, Clonetics, USA), which was then suspended in EBM-2 basal medium (Clonetics, USA) excluding growth factors and bovine serum. Cell suspensions were plated on a 96-well cell culture plate with identical numbers of cells per well, which were incubated for 24 hr in a constant temperature humidified incubator. After the incubation was completed, the medium was discarded, and the wells were treated with the mixed solutions each antibody diluted at serial concentrations (30 ng/mL, 60 ng/mL, 100 ng/mL, 150 ng/mL, 200 ng/mL, 300 ng/mL, 1000 ng/mL, and 3000 ng/mL) and human VEGF diluted at a certain concentration between 30~90 ng/mL The cells treated with the antigen and antibody were cultured for 4 days in a constant temperature humidified incubator, and then treated with resazurin solution (Invitrogen, USA) at 10 µL per well. After 3~4 hr, fluorescence was measured at 530 nm/590 nm. Avastin™ was used as a control, and suppression effects of the antibodies on cell proliferation were quantitated with respect to the fluorescence value of wells treated with VEGF only. The results of HUVEC proliferation rates when treated with antibodies HF-1, HF-4, HF-5 and HF-8 are shown in FIG. 9(b), and the results of cell survival rates when treated with antibodies HF-1 to HF-5, HF-9 and HF-11 are shown in FIGS. 9(c) and (d).

Figure 9A:
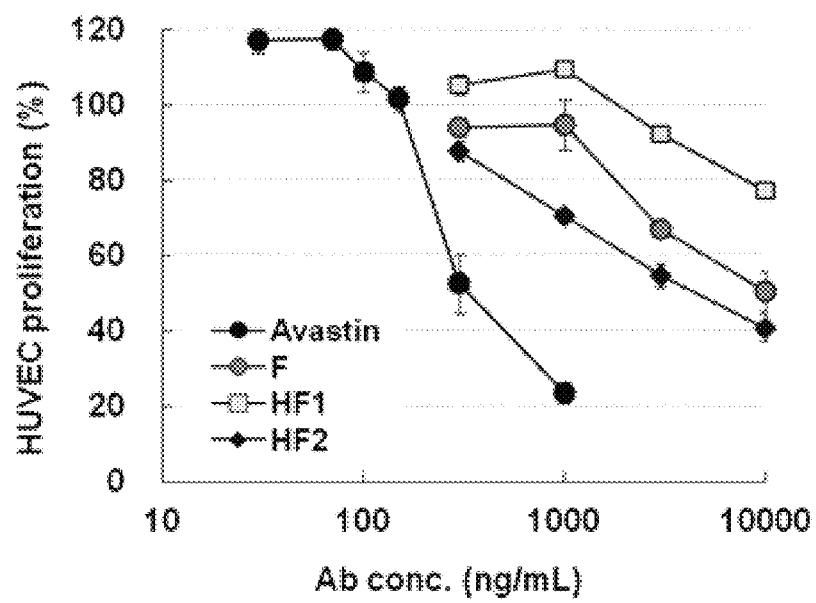
FIG. 9(a), FIG. 9(b), FIG. 9(c), and FIG. 9(d) show the test results of the suppression activity of the inventive antibodies and Avastin on the proliferation of human umbilical vein endothelial cells (HUVEC).
Figure 9B:
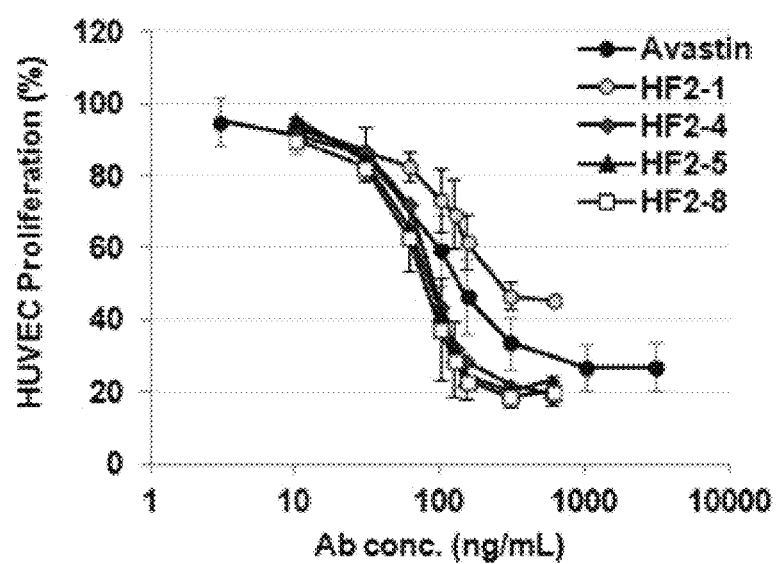
Figure 9C:
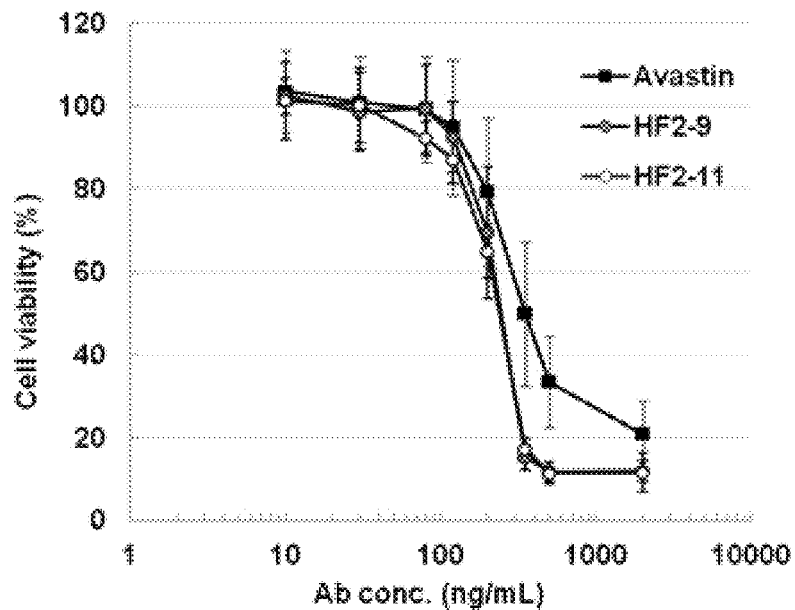
Figure 9D:
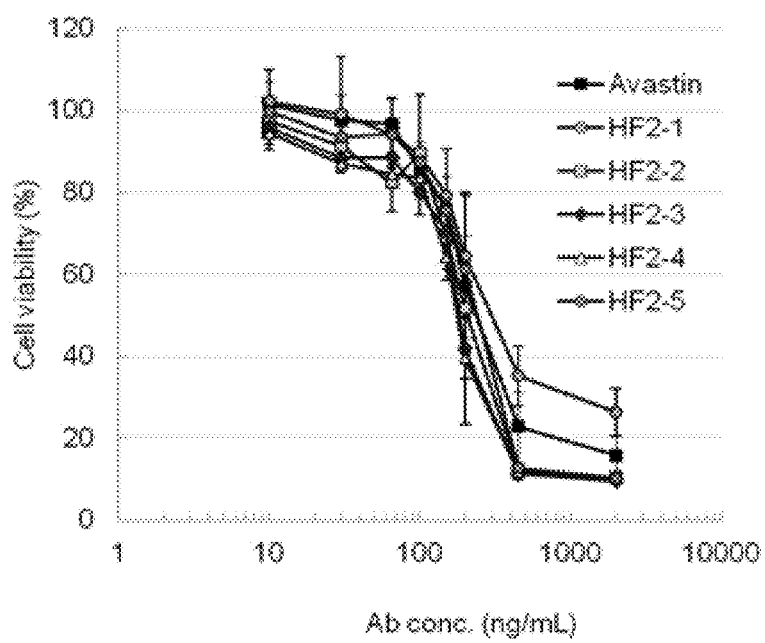

As shown in FIGS. 9(a)-9(d), the inventive antibody HF2-5 suppressed the VEGF-induced proliferation of HUVECs to a similar degree to Avastin™ (FIGS. 9(b) and 9(d)). Also, it was shown that the activity of the antibody was increased through the humanization of F clone (9(a)) and the affinity improvements (9(b), 9(c), 9(d)).

Example 12. Confirmation of Suppression Activity of the Inventive Antibodies on the VEGF-Induced Permeability of HUVEC The suppression activity of the inventive antibodies on the VEGF-induced permeability of HUVECs (Clonetics, USA) was assessed.

One day prior to the test, Transwell having 0.4 µm micro-porous membrane was treated with collagen solution (Sigma, USA) to facilitate the attachment of cells. Cells were collected using trypsin, and suspended at a concentration of $5 \times 10^4$ cells/mL The collagen solution in the Transwells was discarded, and the Transwells were washed once with a buffer solution. 100 ul of cell suspension was dispensed into each well. EGM-2 medium (Clonetics, USA) at a volume of 600 µL was added to the bottom chambers. After a monolayer of endothelial cells was formed, mixed solutions containing diluted antibody (HF2-5, HF2-9, HF2-11 or Avastin™ (control) each at 1× or 10×) and human VEGF diluted to 30 to 90 ng/mL were added to Transwells and the bottom chambers at volumes of 100 µL and 600 µL, respectively, and allowed to react overnight in an incubator. After completion of the reaction, the solutions in the Transwells were removed, and the Transwells were treated with 100 µL of dextran-FITC solution. After 1 hr, fluorescence was measured at 490 nm/520 nm to detect dextrans which passed across the Transwells. EBM medium not containing VEGF was used as a control.

As shown in FIGS. 10(a) and 10(b), the permeability enhancement of endothelial cells by VEGF was suppressed by the antibodies of the present invention in a concentration-dependent manner (10(a)), which was similar to the positive control Avastin™ (10(b)).

Example 13. Confirmation of Suppression Activity of the Inventive Antibody on VEGF-Induced HUVEC Migration The suppression activities of the inventive antibodies HF2-4 and HF2-8 on the VEGF-induced migration property of HUVECs (Clonetics, USA) were assessed.

To assess the migration property of the endothelial cells quantitatively, Boyden chamber test was performed using Transwell having a 3 µm micro-porous membrane. To increase the reactivity of VEGF, the cells being cultured in a flask were starved for more than four hr in EBM-2 basal medium containing 0.1% BSA prior to the test. Cell suspension was placed in the upper chamber at 50,000 cells per well in a volume of 100 µL, whereas mixed solutions containing 3 ng/mL of VEGF diluted in basal medium and 9 ng/mL or 90 ng/mL of the antibody (HF2-4 or HF2-8) were placed to the lower chamber at a volume of 600 uL.

Cells that had migrated to the opposite side of the Transwell following the concentration gradient of VEGF after 24 hr of incubation were detached using trypsin. The detached cells were collected by centrifugation and then lysed with a lysis buffer (Invitrogen, USA). The DNA in the lysed cells was stained with a DNA dye (Invitrogen, USA), and fluorescence was measured at 480 nm/520 nm. The results are shown in FIG. 11.

The results in FIG. 11 indicate that the migration property of the endothelial cells is enhanced by human VEGF, and the enhanced migration property can be suppressed by the antibodies HF2-4 and HF2-8 in a concentration-dependent manner.

Example 14. Confirmation of Suppression Activity of the Inventive Antibody on Tumor Growth To assess the suppression activity of the antibody on tumor growth, the antibody of the present invention was injected into a nude mice in which tumor had been formed by implanting human cancer cells.

Specifically, $2\sim5 \times 10^6$ of HT-29 cells (human colon cancer cell line HTB-38, ATCC) cultured in McCoy's 5A medium containing 10% FBS and 1% penicillin streptomycin, were injected into BALB/c nude mouse (Orient Bio) subcutaneously. When tumors in the mice were sufficiently grown to an average volume of about 200~300 mm³, antibodies HF2-1, HF2-5, HF2-9, and HF2-11 were respectively injected into the divided groups. The antibodies were injected twice a week intraperitoneally at doses of 3 mg/kg or 10 mg/kg. The volume of the tumors (mm$^3$) was measured at different time points (Day 7, Day 14, Day 21, Day 28 and Day 35). A buffer solution (PBS) was used as a negative control group, and Avastin™ was administered in the positive control group. The results are shown in FIGS. 12(a) and 12(b).

As shown in FIGS. 12(a) and 12(b), tumor growth was significantly suppressed in the mice injected with the antibodies as compared to the control group. Especially, antibody-injected groups showed far superior tumor growth suppression effect as compared to Avastin™-injected group.

Example 15. Confirmation of Suppression Activity of the Inventive Antibody on the Retinal Neovascularization In order to confirm the suppression activity of the inventive antibody on the retinal neovascularization, experiments were carried out as following.

First, in order to induce neovascularization in the retina, laser of 150 mW and 530 nm was applied to the right eyes of mice for 0.1 sec using a photocoagulator (viridis laser, Quantel, France) on Day 0 of the experiment. The lesion post projection was adjusted to 0.1 uM. On Day 0 and Day 7, antibodies HF2-4 and HF2-11 were injected into the right eyeball at doses of 1 ug and 5 ug, respectively. Fundus fluorescein angiography was performed on Day 7 and Day 14 to evaluate the degree of fundus angiogenesis. PBS was used as negative control group (vehicle), and Aflibercept (Bayer health care) was used as positive control group (Ref. drug). Fundus angiographic scores were analyzed by dunnett's multiple comparison test, and the results are shown in FIG. 13.

As shown in FIG. 13, the groups injected with antibodies of the present invention showed superior suppression effects on the choroidal angiogenesis as compared to the negative control group, and was at least equal to a marketed comparator drug.

While the present invention has been described with respect to the above specific embodiments, it should be recognized that various modifications and changes may be made to the present invention by those skilled in the art which also fall within the scope of the present invention as defined by the appended claims.

What is claimed is:

1. An antibody that binds to vascular endothelial growth factor (VEGF), the antibody comprising:
   1) a light chain variable region comprising complementarity determining region (CDR)1, CDR2 and CDR3, wherein the CDR1 is represented by an amino acid sequence selected from the group consisting of SEQ ID NOs: 4-14; the CDR2 is represented by the amino acid sequence of SEQ ID NO: 1; and the CDR3 is represented by the amino acid sequence of SEQ ID NO: 2; and
   2) a heavy chain variable region comprising CDR1, CDR2 and CDR3, wherein the CDR1 is represented by an amino acid sequence selected from the group consisting of SEQ ID NOs: 15-34; the CDR 2 is represented an the amino acid sequence selected from the group consisting of SEQ ID NOs: 35-50; and the CDR3 is represented by the amino acid sequence of SEQ ID NO: 3, wherein the antibody is selected from the group consisting of:

(i) the antibody comprising 1) a light chain variable region comprising CDR1 represented by the amino acid sequence of SEQ ID NO: 4, CDR 2 represented by the amino acid sequence of SEQ ID NO: 1 and CDR3 represented by the amino acid sequence of SEQ ID NO: 2; and 2) a heavy chain variable region comprising CDR1 represented by the amino acid sequence of SEQ ID NO: 15, CDR 2 represented by the amino acid sequence of SEQ ID NO: 35 and CDR3 represented by the amino acid sequence of SEQ ID NO: 3;

(ii) the antibody comprising 1) a light chain variable region comprising CDR1 represented by the amino acid sequence of SEQ ID NO: 5, CDR 2 represented by the amino acid sequence of SEQ ID NO: 1 and CDR3 represented by the amino acid sequence of SEQ ID NO: 2; and 2) a heavy chain variable region comprising CDR1 represented by the amino acid sequence of SEQ ID NO: 16, CDR 2 represented by the amino acid sequence of SEQ ID NO: 36 and CDR3 represented by the amino acid sequence of SEQ ID NO: 3;

(iii) the antibody comprising 1) a light chain variable region comprising CDR1 represented by the amino acid sequence of SEQ ID NO: 5, CDR 2 represented by the amino acid sequence of SEQ ID NO: 1 and CDR3 represented by the amino acid sequence of SEQ ID NO: 2; and 2) a heavy chain variable region comprising CDR1 represented by the amino acid sequence of SEQ ID NO: 17, CDR 2 represented by the amino acid sequence of SEQ ID NO: 37 and CDR3 represented by the amino acid sequence of SEQ ID NO: 3;

(iv) the antibody comprising 1) a light chain variable region comprising CDR1 represented by the amino acid sequence of SEQ ID NO: 5, CDR 2 represented by the amino acid sequence of SEQ ID NO: 1 and CDR3 represented by the amino acid sequence of SEQ ID NO: 2; and 2) a heavy chain variable region comprising CDR1 represented by the amino acid sequence of SEQ ID NO: 18, CDR 2 represented by the amino acid sequence of SEQ ID NO: 38 and CDR3 represented by the amino acid sequence of SEQ ID NO: 3;

(v) the antibody comprising 1) a light chain variable region comprising CDR1 represented by the amino acid sequence of SEQ ID NO: 5, CDR 2 represented by the amino acid sequence of SEQ ID NO: 1 and CDR3 represented by the amino acid sequence of SEQ ID NO: 2; and 2) a heavy chain variable region comprising CDR1 represented by the amino acid sequence of SEQ ID NO: 19, CDR 2 represented by the amino acid sequence of SEQ ID NO: 39 and CDR3 represented by the amino acid sequence of SEQ ID NO: 3;

(vi) the antibody comprising 1) a light chain variable region comprising CDR1 represented by the amino acid sequence of SEQ ID NO: 5, CDR 2 represented by the amino acid sequence of SEQ ID NO: 1 and CDR3 represented by the amino acid sequence of SEQ ID NO: 2; and 2) a heavy chain variable region comprising CDR1 represented by the amino acid sequence of SEQ ID NO: 20, CDR 2 represented by the amino acid sequence of SEQ ID NO: 40 and CDR3 represented by the amino acid sequence of SEQ ID NO: 3;

(vii) the antibody comprising 1) a light chain variable region comprising CDR1 represented by the amino acid sequence of SEQ ID NO: 6, CDR 2 represented by the amino acid sequence of SEQ ID NO: 1 and CDR3 represented by the amino acid sequence of SEQ ID NO: 2; and 2) a heavy chain variable region comprising CDR1 represented by the amino acid sequence of SEQ ID NO: 21, CDR 2 represented by the amino acid sequence of SEQ ID NO: 38 and CDR3 represented by the amino acid sequence of SEQ ID NO: 3;

(viii) the antibody comprising 1) a light chain variable region comprising CDR1 represented by the amino acid sequence of SEQ ID NO: 6, CDR 2 represented by the amino acid sequence of SEQ ID NO: 1 and CDR3 represented by the amino acid sequence of SEQ ID NO: 2; and 2) a heavy chain variable region comprising CDR1 represented by the amino acid sequence of SEQ ID NO: 22, CDR 2 represented by the amino acid sequence of SEQ ID NO: 38 and CDR3 represented by the amino acid sequence of SEQ ID NO: 3;

(ix) the antibody comprising 1) a light chain variable region comprising CDR1 represented by the amino acid sequence of SEQ ID NO: 7, CDR 2 represented by the amino acid sequence of SEQ ID NO: 1 and CDR3 represented by the amino acid sequence of SEQ ID NO: 2; and 2) a heavy chain variable region comprising CDR1 represented by the amino acid sequence of SEQ ID NO: 23, CDR 2 represented by the amino acid sequence of SEQ ID NO: 41 and CDR3 represented by the amino acid sequence of SEQ ID NO: 3;

(x) the antibody comprising 1) a light chain variable region comprising CDR1 represented by the amino acid sequence of SEQ ID NO: 6, CDR 2 represented by the amino acid sequence of SEQ ID NO: 1 and CDR3 represented by the amino acid sequence of SEQ ID NO: 2; and 2) a heavy chain variable region comprising CDR1 represented by the amino acid sequence of SEQ ID NO: 24, CDR 2 represented by the amino acid sequence of SEQ ID NO: 38 and CDR3 represented by the amino acid sequence of SEQ ID NO: 3;

(xi) the antibody comprising 1) a light chain variable region comprising CDR1 represented by the amino acid sequence of SEQ ID NO: 6, CDR 2 represented by the amino acid sequence of SEQ ID NO: 1 and CDR3 represented by the amino acid sequence of SEQ ID NO: 2; and 2) a heavy chain variable region comprising CDR1 represented by the amino acid sequence of SEQ ID NO: 25, CDR 2 represented by the amino acid sequence of SEQ ID NO: 38 and CDR3 represented by the amino acid sequence of SEQ ID NO: 3;

(xii) the antibody comprising 1) a light chain variable region comprising CDR1 represented by the amino acid sequence of SEQ ID NO: 8, CDR 2 represented by the amino acid sequence of SEQ ID NO: 1 and CDR3 represented by the amino acid sequence of SEQ ID NO: 2; and 2) a heavy chain variable region comprising CDR1 represented by the amino acid sequence of SEQ ID NO: 26, CDR 2 represented by the amino acid sequence of SEQ ID NO: 42 and CDR3 represented by the amino acid sequence of SEQ ID NO: 3;

(xiii) the antibody comprising 1) a light chain variable region comprising CDR1 represented by the amino acid sequence of SEQ ID NO: 6, CDR 2 represented by the amino acid sequence of SEQ ID NO: 1 and CDR3 represented by the amino acid sequence of SEQ ID NO: 2; and 2) a heavy chain variable region comprising CDR1 represented by the amino acid sequence of SEQ ID NO: 27, CDR 2 represented by the amino acid sequence of SEQ ID NO: 38 and CDR3 represented by the amino acid sequence of SEQ ID NO: 3;

(xiv) the antibody comprising 1) a light chain variable region comprising CDR1 represented by the amino acid sequence of SEQ ID NO: 9, CDR 2 represented by the amino acid sequence of SEQ ID NO: 1 and CDR3 represented by the amino acid sequence of SEQ ID NO: 2; and 2) a heavy chain variable region comprising CDR1 represented by the amino acid sequence of SEQ ID NO: 28, CDR 2 represented by the amino acid sequence of SEQ ID NO: 43 and CDR3 represented by the amino acid sequence of SEQ ID NO: 3;

(xv) the antibody comprising 1) a light chain variable region comprising CDR1 represented by the amino acid sequence of SEQ ID NO: 5, CDR 2 represented by the amino acid sequence of SEQ ID NO: 1 and CDR3 represented by the amino acid sequence of SEQ ID NO: 2; and 2) a heavy chain variable region comprising CDR1 represented by the amino acid sequence of SEQ ID NO: 29, CDR 2 represented by the amino acid sequence of SEQ ID NO: 44 and CDR3 represented by the amino acid sequence of SEQ ID NO: 3;

(xvi) the antibody comprising 1) a light chain variable region comprising CDR1 represented by the amino acid sequence of SEQ ID NO: 10, CDR 2 represented by the amino acid sequence of SEQ ID NO: 1 and CDR3 represented by the amino acid sequence of SEQ ID NO: 2; and 2) a heavy chain variable region comprising CDR1 represented by the amino acid sequence of SEQ ID NO: 30, CDR 2 represented by the amino acid sequence of SEQ ID NO: 45 and CDR3 represented by the amino acid sequence of SEQ ID NO: 3;

(xvii) the antibody comprising 1) a light chain variable region comprising CDR1 represented by the amino acid sequence of SEQ ID NO: 11, CDR 2 represented by the amino acid sequence of SEQ ID NO: 1 and CDR3 represented by the amino acid sequence of SEQ ID NO: 2; and 2) a heavy chain variable region comprising CDR1 represented by the amino acid sequence of SEQ ID NO: 31, CDR 2 represented by the amino acid sequence of SEQ ID NO: 42 and CDR3 represented by the amino acid sequence of SEQ ID NO: 3;

(xviii) the antibody comprising 1) a light chain variable region comprising CDR1 represented by the amino acid sequence of SEQ ID NO: 11, CDR 2 represented by the amino acid sequence of SEQ ID NO: 1 and CDR3 represented by the amino acid sequence of SEQ ID NO: 2; and 2) a heavy chain variable region comprising CDR1 represented by the amino acid sequence of SEQ ID NO: 20, CDR 2 represented by the amino acid sequence of SEQ ID NO: 39 and CDR3 represented by the amino acid sequence of SEQ ID NO: 3;

(xix) the antibody comprising 1) a light chain variable region comprising CDR1 represented by the amino acid sequence of SEQ ID NO: 11, CDR 2 represented by the amino acid sequence of SEQ ID NO: 1 and CDR3 represented by the amino acid sequence of SEQ ID NO: 2; and 2) a heavy chain variable region comprising CDR1 represented by the amino acid sequence of SEQ ID NO: 32, CDR 2 represented by the amino acid sequence of SEQ ID NO: 46 and CDR3 represented by the amino acid sequence of SEQ ID NO: 3;

(xx) the antibody comprising 1) a light chain variable region comprising CDR1 represented by the amino acid sequence of SEQ ID NO: 5, CDR 2 represented by the amino acid sequence of SEQ ID NO: 1 and CDR3 represented by the amino acid sequence of SEQ ID NO: 2; and 2) a heavy chain variable region comprising CDR1 represented by the amino acid sequence of SEQ ID NO: 33, CDR 2 represented by the amino acid sequence of SEQ ID NO: 45 and CDR3 represented by the amino acid sequence of SEQ ID NO: 3;

(xxi) the antibody comprising 1) a light chain variable region comprising CDR1 represented by the amino acid sequence of SEQ ID NO: 5, CDR 2 represented by the amino acid sequence of SEQ ID NO: 1 and CDR3 represented by the amino acid sequence of SEQ ID NO: 2; and 2) a heavy chain variable region comprising CDR1 represented by the amino acid sequence of SEQ ID NO: 34, CDR 2 represented by the amino acid sequence of SEQ ID NO: 47 and CDR3 represented by the amino acid sequence of SEQ ID NO: 3;

(xxii) the antibody comprising 1) a light chain variable region comprising CDR1 represented by the amino acid sequence of SEQ ID NO: 6, CDR 2 represented by the amino acid sequence of SEQ ID NO: 1 and CDR3 represented by the amino acid sequence of SEQ ID NO: 2; and 2) a heavy chain variable region comprising CDR1 represented by the amino acid sequence of SEQ ID NO: 25, CDR 2 represented by the amino acid sequence of SEQ ID NO: 48 and CDR3 represented by the amino acid sequence of SEQ ID NO: 3;

(xxiii) the antibody comprising 1) a light chain variable region comprising CDR1 represented by the amino acid sequence of SEQ ID NO: 12, CDR 2 represented by the amino acid sequence of SEQ ID NO: 1 and CDR3 represented by the amino acid sequence of SEQ ID NO: 2; and 2) a heavy chain variable region comprising CDR1 represented by the amino acid sequence of SEQ ID NO: 31, CDR 2 represented by the amino acid sequence of SEQ ID NO: 38 and CDR3 represented by the amino acid sequence of SEQ ID NO: 3;

(xxiv) the antibody comprising 1) a light chain variable region comprising CDR1 represented by the amino acid sequence of SEQ ID NO: 9, CDR 2 represented by the amino acid sequence of SEQ ID NO: 1 and CDR3 represented by the amino acid sequence of SEQ ID NO: 2 and 2) a heavy chain variable region comprising CDR1 represented by the amino acid sequence of SEQ ID NO: 31, CDR 2 represented by the amino acid sequence of SEQ ID NO: 46 and CDR3 represented by the amino acid sequence of SEQ ID NO: 3;

(xxv) the antibody comprising 1) a light chain variable region comprising CDR1 represented by the amino acid sequence of SEQ ID NO: 10, CDR 2 represented by the amino acid sequence of SEQ ID NO: 1 and CDR3 represented by the amino acid sequence of SEQ ID NO: 2; and 2) a heavy chain variable region comprising CDR1 represented by the amino acid sequence of SEQ ID NO: 17, CDR 2 represented by the amino acid sequence of SEQ ID NO: 42 and CDR3 represented by the amino acid sequence of SEQ ID NO: 3;

(xxvi) the antibody comprising 1) a light chain variable region comprising CDR1 represented by the amino acid sequence of SEQ ID NO: 13, CDR 2 represented by the amino acid sequence of SEQ ID NO: 1 and CDR3 represented by the amino acid sequence of SEQ ID NO: 2; and 2) a heavy chain variable region comprising CDR1 represented by the amino acid sequence of SEQ ID NO: 34, CDR 2 represented by the amino acid sequence of SEQ ID NO: 49 and CDR3 represented by the amino acid sequence of SEQ ID NO: 3; and (xxvii) the antibody comprising 1) a light chain variable region comprising CDR1 represented by the amino acid sequence of SEQ ID NO: 14, CDR 2 represented by the amino acid sequence of SEQ ID NO: 1 and CDR3 represented by the amino acid sequence of SEQ ID NO: 2; and 2) a heavy chain variable region comprising CDR1 represented by the amino acid sequence of SEQ ID NO: 17, CDR 2 represented by the amino acid sequence of SEQ ID NO: 50 and CDR3 represented by the amino acid sequence of SEQ ID NO: 3.

2. An antibody that binds to vascular endothelial growth factor (VEGF), wherein the antibody is selected from the group consisting of:
  (i) the antibody comprising 1) a light chain variable region represented by the amino acid sequence of SEQ ID NO: 54 and 2) a heavy chain variable region represented by the amino acid sequence of SEQ ID NO: 78;
  (ii) the antibody comprising 1) a light chain variable region represented by the amino acid sequence of SEQ ID NO: 55 and 2) a heavy chain variable region represented by the amino acid sequence of SEQ ID NO: 79;
  (iii) the antibody comprising 1) a light chain variable region represented by the amino acid sequence of SEQ ID NO: 55 and 2) a heavy chain variable region represented by the amino acid sequence of SEQ ID NO: 80;
  (iv) the antibody comprising 1) a light chain variable region represented by the amino acid sequence of SEQ ID NO: 56 and 2) a heavy chain variable region represented by the amino acid sequence of SEQ ID NO: 81;
  (v) the antibody comprising 1) a light chain variable region represented by the amino acid sequence of SEQ ID NO: 55 and 2) a heavy chain variable region represented by the amino acid sequence of SEQ ID NO: 82;
  (vi) the antibody comprising 1) a light chain variable region represented by the amino acid sequence of SEQ ID NO: 55 and 2) a heavy chain variable region represented by the amino acid sequence of SEQ ID NO: 83;
  (vii) the antibody comprising 1) a light chain variable region represented by the amino acid sequence of SEQ ID NO: 57 and 2) a heavy chain variable region represented by the amino acid sequence of SEQ ID NO: 84;
  (viii) the antibody comprising 1) a light chain variable region represented by the amino acid sequence of SEQ ID NO: 57 and 2) a heavy chain variable region represented by the amino acid sequence of SEQ ID NO: 85;
  (ix) the antibody comprising 1) a light chain variable region represented by the amino acid sequence of SEQ ID NO: 58 and 2) a heavy chain variable region represented by the amino acid sequence of SEQ ID NO: 86;
  (x) the antibody comprising 1) a light chain variable region represented by the amino acid sequence of SEQ ID NO: 57 and 2) a heavy chain variable region represented by the amino acid sequence of SEQ ID NO: 87;
  (xi) the antibody comprising 1) a light chain variable region represented by the amino acid sequence of SEQ ID NO: 57 and 2) a heavy chain variable region represented by the amino acid sequence of SEQ ID NO: 88;
  (xii) the antibody comprising 1) a light chain variable region represented by the amino acid sequence of SEQ ID NO: 59 and 2) a heavy chain variable region represented by the amino acid sequence of SEQ ID NO: 89;
  (xiii) the antibody comprising 1) a light chain variable region represented by the amino acid sequence of SEQ ID NO: 57 and 2) a heavy chain variable region represented by the amino acid sequence of SEQ ID NO: 90;
  (xiv) the antibody comprising 1) a light chain variable region represented by the amino acid sequence of SEQ ID NO: 60 and 2) a heavy chain variable region represented by the amino acid sequence of SEQ ID NO: 91;
  (xv) the antibody comprising 1) a light chain variable region represented by the amino acid sequence of SEQ ID NO: 55 and 2) a heavy chain variable region represented by the amino acid sequence of SEQ ID NO: 92;
  (xvi) the antibody comprising 1) a light chain variable region represented by the amino acid sequence of SEQ ID NO: 61 and 2) a heavy chain variable region represented by the amino acid sequence of SEQ ID NO: 93;
  (xvii) the antibody comprising 1) a light chain variable region represented by the amino acid sequence of SEQ ID NO: 62 and 2) a heavy chain variable region represented by the amino acid sequence of SEQ ID NO: 94;
  (xviii) the antibody comprising 1) a light chain variable region represented by the amino acid sequence of SEQ ID NO: 62 and 2) a heavy chain variable region represented by the amino acid sequence of SEQ ID NO: 95;
  (xix) the antibody comprising 1) a light chain variable region represented by the amino acid sequence of SEQ ID NO: 62 and 2) a heavy chain variable region represented by the amino acid sequence of SEQ ID NO: 96;
  (xx) the antibody comprising 1) a light chain variable region represented by the amino acid sequence of SEQ ID NO: 55 and 2) a heavy chain variable region represented by the amino acid sequence of SEQ ID NO: 97;
  (xxi) the antibody comprising 1) a light chain variable region represented by the amino acid sequence of SEQ ID NO: 55 and 2) a heavy chain variable region represented by the amino acid sequence of SEQ ID NO: 98;
  (xxii) the antibody comprising 1) a light chain variable region represented by the amino acid sequence of SEQ ID NO: 57 and 2) a heavy chain variable region represented by the amino acid sequence of SEQ ID NO: 99;
  (xxiii) the antibody comprising 1) a light chain variable region represented by the amino acid sequence of SEQ ID NO: 63 and 2) a heavy chain variable region represented by the amino acid sequence of SEQ ID NO: 100;
  (xxiv) the antibody comprising 1) a light chain variable region represented by the amino acid sequence of SEQ ID NO: 60 and 2) a heavy chain variable region represented by the amino acid sequence of SEQ ID NO: 101;
  (xxv) the antibody comprising 1) a light chain variable region represented by the amino acid sequence of SEQ ID NO: 61 and 2) a heavy chain variable region represented by the amino acid sequence of SEQ ID NO: 102;

(xxvi) the antibody comprising 1) a light chain variable region represented by the amino acid sequence of SEQ ID NO: 64 and 2) a heavy chain variable region represented by the amino acid sequence of SEQ ID NO: 103; and (xxvii) the antibody comprising 1) a light chain variable region represented by the amino acid sequence of SEQ ID NO: 65 and 2) a heavy chain variable region represented by the amino acid sequence of SEQ ID NO: 104.

3. The VEGF-binding antibody of claim 1, wherein the antibody is a human or humanized antibody.

4. The VEGF-binding antibody of claim 1, wherein the antibody is IgG1, IgG2, IgG3, IgG4, IgA1, IgA2, IgD, IgE or IgM.

5. The VEGF-binding antibody of claim 4, wherein the antibody is Fab, Fab', F(ab')$_2$, Fv, dAb, scFv or a scaffold conjugate which comprises the CDR of said antibody.

6. A pharmaceutical composition comprising the antibody according to claim 1.

7. The pharmaceutical composition of claim 6, wherein the pharmaceutical composition further comprising a chemotherapeutic agent selected from a group consisting of an alkylating agent, an antimetabolite, a folic acid homologue, a pyrimidine homologue, a purine homologue and related inhibitor, a vinca alkaloid, an epipodophyllotoxin, antibiotics, L-asparaginase, a topoisomerase inhibitor, interferon, a platinum coordination complex, anthracenedione-substituted urea, a methyl hydrazine derivative, an adrenocortical suppressor, an adrenocorticosteroid, progestin, estrogen, antiestrogen, androgen, antiandrogen and gonadotropin-releasing hormone homologue.

8. The pharmaceutical composition of claim 6, wherein the pharmaceutical composition further comprising a drug selected from a group consisting of a fluoropyrimidine-based drug, paclitaxel, a platinum-based drug, interferon alpha-2a, carboplatin, doxorubicin, cisplatin, gemcitabine, 5-fluorouracil, leucovorin, irinotecan, oxalaplatin, capecitabine, docetaxel, and a mixture thereof.

9. A diagnostic kit for cancer or an angiogenesis-related disease caused by over-expression of VEGF, the kit comprising the antibody that binds to VEGF according to claim 1.

10. The VEGF-binding antibody of claim 2, wherein the antibody is a human or humanized antibody.

11. The VEGF-binding antibody of claim 2, wherein the antibody is IgG1, IgG2, IgG3, IgG4, IgA1, IgA2, IgD, IgE or IgM.

12. The VEGF-binding antibody of claim 11, wherein the antibody is Fab, Fab', F(ab')$_2$, Fv, dAb, scFv or a scaffold conjugate which comprises the CDR of said antibody.

13. A pharmaceutical composition comprising the antibody according to claim 2.

14. The pharmaceutical composition of claim 13, wherein the pharmaceutical composition further comprising a chemotherapeutic agent selected from a group consisting of an alkylating agent, an antimetabolite, a folic acid homologue, a pyrimidine homologue, a purine homologue and related inhibitor, a vinca alkaloid, an epipodophyllotoxin, antibiotics, L-asparaginase, a topoisomerase inhibitor, interferon, a platinum coordination complex, anthracenedione-substituted urea, a methyl hydrazine derivative, an adrenocortical suppressor, an adrenocorticosteroid, progestin, estrogen, antiestrogen, androgen, antiandrogen and gonadotropin-releasing hormone homologue.

15. The pharmaceutical composition of claim 13, wherein the pharmaceutical composition further comprising a drug selected from a group consisting of a fluoropyrimidine-based drug, paclitaxel, a platinum-based drug, interferon alpha-2a, carboplatin, doxorubicin, cisplatin, gemcitabine, 5-fluorouracil, leucovorin, irinotecan, oxalaplatin, capecitabine, docetaxel, and a mixture thereof.

16. A diagnostic kit for cancer or an angiogenesis-related disease caused by over-expression of VEGF, the kit comprising the antibody that binds to VEGF according to claim 2.

* * * * *

SEQUENCE LISTING

```
<160> NUMBER OF SEQ ID NOS: 151

<210> SEQ ID NO 1
<211> LENGTH: 7
<212> TYPE: PRT
<213> ORGANISM: Artificial Sequence
<220> FEATURE:
<223> OTHER INFORMATION: amino acid sequence of CDR2 in light chain
      variable region (LCDR2)

<400> SEQUENCE: 1

Trp Asp Asp Lys Arg Pro Ser
  1               5

<210> SEQ ID NO 2
<211> LENGTH: 11
<212> TYPE: PRT
<213> ORGANISM: Artificial Sequence
<220> FEATURE:
<223> OTHER INFORMATION: amino acid sequence of CDR3 in light chain
      variable region (LCDR3)

<400> SEQUENCE: 2

Gly Ala Trp Glu Tyr Ser Ser Asp Val Gly Ile
  1               5                  10

<210> SEQ ID NO 3
<211> LENGTH: 13
<212> TYPE: PRT
<213> ORGANISM: Artificial Sequence
<220> FEATURE:
<223> OTHER INFORMATION: amino acid sequence of CDR3 in heavy chain
      variable region (HCDR3)

<400> SEQUENCE: 3

Asp Phe Ser Thr Ser Tyr Gly Ala Asp Ser Ile Asp Ala
  1               5                  10

<210> SEQ ID NO 4
<211> LENGTH: 11
<212> TYPE: PRT
```

```
<213> ORGANISM: Artificial Sequence
<220> FEATURE:
<223> OTHER INFORMATION: amino acid sequence of LCDR1 of Clone F

<400> SEQUENCE: 4

Ser Gly Gly Ser Asn Ser Ala Tyr Gly Tyr Gly
 1               5                   10

<210> SEQ ID NO 5
<211> LENGTH: 11
<212> TYPE: PRT
<213> ORGANISM: Artificial Sequence
<220> FEATURE:
<223> OTHER INFORMATION: amino acid sequence of LCDR1 of Clone HF2-1,
      HF2-2, HF2-3, HF2-4, HF2-5, HF2-14, HF2-19, HF2-20

<400> SEQUENCE: 5

Ser Gly Gly Ser Asp Ser Ala Tyr Gly Tyr Gly
 1               5                   10

<210> SEQ ID NO 6
<211> LENGTH: 11
<212> TYPE: PRT
<213> ORGANISM: Artificial Sequence
<220> FEATURE:
<223> OTHER INFORMATION: amino acid sequence of LCDR1 of Clone HF2-6,
      HF2-7, HF2-9, HF2-10, HF2-12, HF2-21

<400> SEQUENCE: 6

Ser Gly Gly Ser Met Glu Pro Leu Gly Tyr Gly
 1               5                   10

<210> SEQ ID NO 7
<211> LENGTH: 11
<212> TYPE: PRT
<213> ORGANISM: Artificial Sequence
<220> FEATURE:
<223> OTHER INFORMATION: amino acid sequence of LCDR1 of Clone HF2-8

<400> SEQUENCE: 7

Ser Gly Gly Ser Thr Tyr Ser Leu Gly Tyr Gly
 1               5                   10

<210> SEQ ID NO 8
<211> LENGTH: 11
<212> TYPE: PRT
<213> ORGANISM: Artificial Sequence
<220> FEATURE:
<223> OTHER INFORMATION: amino acid sequence of LCDR1 of Clone HF2-11

<400> SEQUENCE: 8

Ser Gly Gly Ser Ser Glu Pro Leu Gly Tyr Gly
 1               5                   10

<210> SEQ ID NO 9
<211> LENGTH: 11
<212> TYPE: PRT
<213> ORGANISM: Artificial Sequence
<220> FEATURE:
<223> OTHER INFORMATION: amino acid sequence of LCDR1 of Clone HF2-13,
      HF2-23

<400> SEQUENCE: 9

Ser Gly Gly Ser Asp Leu Leu Leu Gly Tyr Gly
 1               5                   10

<210> SEQ ID NO 10
```

```
<211> LENGTH: 11
<212> TYPE: PRT
<213> ORGANISM: Artificial Sequence
<220> FEATURE:
<223> OTHER INFORMATION: amino acid sequence of LCDR1 of Clone HF2-15,
      HF2-24

<400> SEQUENCE: 10

Ser Gly Gly Ser Gln Glu Ser Leu Gly Tyr Gly
  1               5                  10

<210> SEQ ID NO 11
<211> LENGTH: 11
<212> TYPE: PRT
<213> ORGANISM: Artificial Sequence
<220> FEATURE:
<223> OTHER INFORMATION: amino acid sequence of LCDR1 of Clone HF2-16,
      HF2-17, HF2-18

<400> SEQUENCE: 11

Ser Gly Gly Ser Ile Glu Pro Leu Gly Tyr Gly
  1               5                  10

<210> SEQ ID NO 12
<211> LENGTH: 11
<212> TYPE: PRT
<213> ORGANISM: Artificial Sequence
<220> FEATURE:
<223> OTHER INFORMATION: amino acid sequence of LCDR1 of Clone HF2-22

<400> SEQUENCE: 12

Ser Gly Gly Ser Thr Ala Gly Val Gly Tyr Gly
  1               5                  10

<210> SEQ ID NO 13
<211> LENGTH: 11
<212> TYPE: PRT
<213> ORGANISM: Artificial Sequence
<220> FEATURE:
<223> OTHER INFORMATION: amino acid sequence of LCDR1 of Clone HF2-25

<400> SEQUENCE: 13

Ser Gly Gly Ser Asn Phe Pro Met Gly Tyr Gly
  1               5                  10

<210> SEQ ID NO 14
<211> LENGTH: 11
<212> TYPE: PRT
<213> ORGANISM: Artificial Sequence
<220> FEATURE:
<223> OTHER INFORMATION: amino acid sequence of LCDR1 of Clone HF2-26

<400> SEQUENCE: 14

Thr Ala Pro Ala Asp Ser Ala Tyr Gly Tyr Gly
  1               5                  10

<210> SEQ ID NO 15
<211> LENGTH: 10
<212> TYPE: PRT
<213> ORGANISM: Artificial Sequence
<220> FEATURE:
<223> OTHER INFORMATION: amino acid sequence of HCDR1 of Clone F

<400> SEQUENCE: 15

Gly Phe Thr Phe Ser Ser His Gly Met Gln
  1               5                  10
```

```
<210> SEQ ID NO 16
<211> LENGTH: 10
<212> TYPE: PRT
<213> ORGANISM: Artificial Sequence
<220> FEATURE:
<223> OTHER INFORMATION: amino acid sequence of HCDR1 of Clone HF2-1

<400> SEQUENCE: 16

Asn Phe Val Phe Arg Ser His Gly Met Gln
 1               5                  10

<210> SEQ ID NO 17
<211> LENGTH: 10
<212> TYPE: PRT
<213> ORGANISM: Artificial Sequence
<220> FEATURE:
<223> OTHER INFORMATION: amino acid sequence of HCDR1 of Clone HF2-2,
      HF2-24, HF2-26

<400> SEQUENCE: 17

Arg Phe Asn Met Arg Ser His Gly Met Gln
 1               5                  10

<210> SEQ ID NO 18
<211> LENGTH: 10
<212> TYPE: PRT
<213> ORGANISM: Artificial Sequence
<220> FEATURE:
<223> OTHER INFORMATION: amino acid sequence of HCDR1 of Clone HF2-3

<400> SEQUENCE: 18

His Phe Asn Met Arg Ser His Gly Met Gln
 1               5                  10

<210> SEQ ID NO 19
<211> LENGTH: 10
<212> TYPE: PRT
<213> ORGANISM: Artificial Sequence
<220> FEATURE:
<223> OTHER INFORMATION: amino acid sequence of HCDR1 of Clone HF2-4

<400> SEQUENCE: 19

Gly Trp Ser Met Arg Ser His Gly Met Gln
 1               5                  10

<210> SEQ ID NO 20
<211> LENGTH: 10
<212> TYPE: PRT
<213> ORGANISM: Artificial Sequence
<220> FEATURE:
<223> OTHER INFORMATION: amino acid sequence of HCDR1 of Clone HF2-5,
      HF2-17

<400> SEQUENCE: 20

Gly Phe Met Ile Arg Ser His Gly Met Gln
 1               5                  10

<210> SEQ ID NO 21
<211> LENGTH: 10
<212> TYPE: PRT
<213> ORGANISM: Artificial Sequence
<220> FEATURE:
<223> OTHER INFORMATION: amino acid sequence of HCDR1 of Clone HF2-6

<400> SEQUENCE: 21

Arg Phe Leu Leu Arg Ser His Gly Met Gln
 1               5                  10
```

<210> SEQ ID NO 22
<211> LENGTH: 10
<212> TYPE: PRT
<213> ORGANISM: Artificial Sequence
<220> FEATURE:
<223> OTHER INFORMATION: amino acid sequence of HCDR1 of Clone HF2-7

<400> SEQUENCE: 22

Gln Phe Trp Ile Arg Ser His Gly Met Gln
 1               5                  10

<210> SEQ ID NO 23
<211> LENGTH: 10
<212> TYPE: PRT
<213> ORGANISM: Artificial Sequence
<220> FEATURE:
<223> OTHER INFORMATION: amino acid sequence of HCDR1 of Clone HF2-8

<400> SEQUENCE: 23

Gly Phe His Ile Arg Ser His Gly Met Gln
 1               5                  10

<210> SEQ ID NO 24
<211> LENGTH: 10
<212> TYPE: PRT
<213> ORGANISM: Artificial Sequence
<220> FEATURE:
<223> OTHER INFORMATION: amino acid sequence of HCDR1 of Clone HF2-9

<400> SEQUENCE: 24

Met Phe Arg Ile Arg Ser His Gly Met Gln
 1               5                  10

<210> SEQ ID NO 25
<211> LENGTH: 10
<212> TYPE: PRT
<213> ORGANISM: Artificial Sequence
<220> FEATURE:
<223> OTHER INFORMATION: amino acid sequence of HCDR1 of Clone HF2-10,
      HF2-21

<400> SEQUENCE: 25

Phe Gln Tyr Phe Arg Ser His Gly Met Gln
 1               5                  10

<210> SEQ ID NO 26
<211> LENGTH: 10
<212> TYPE: PRT
<213> ORGANISM: Artificial Sequence
<220> FEATURE:
<223> OTHER INFORMATION: amino acid sequence of HCDR1 of Clone HF2-11

<400> SEQUENCE: 26

Gly Phe Leu Ile Arg Ser His Gly Met Gln
 1               5                  10

<210> SEQ ID NO 27
<211> LENGTH: 10
<212> TYPE: PRT
<213> ORGANISM: Artificial Sequence
<220> FEATURE:
<223> OTHER INFORMATION: amino acid sequence of HCDR1 of Clone HF2-12

<400> SEQUENCE: 27

Tyr Ser Glu Val Arg Ser His Gly Met Gln
 1               5                  10

```
<210> SEQ ID NO 28
<211> LENGTH: 10
<212> TYPE: PRT
<213> ORGANISM: Artificial Sequence
<220> FEATURE:
<223> OTHER INFORMATION: amino acid sequence of HCDR1 of Clone HF2-13

<400> SEQUENCE: 28

Gly Phe Leu Val Arg Ser His Gly Met Gln
 1               5                  10

<210> SEQ ID NO 29
<211> LENGTH: 10
<212> TYPE: PRT
<213> ORGANISM: Artificial Sequence
<220> FEATURE:
<223> OTHER INFORMATION: amino acid sequence of HCDR1 of Clone HF2-14

<400> SEQUENCE: 29

His Ser Ser Ile Arg Ser His Gly Met Gln
 1               5                  10

<210> SEQ ID NO 30
<211> LENGTH: 10
<212> TYPE: PRT
<213> ORGANISM: Artificial Sequence
<220> FEATURE:
<223> OTHER INFORMATION: amino acid sequence of HCDR1 of Clone HF2-15

<400> SEQUENCE: 30

Gly Phe Val Val Arg Ser His Gly Met Gln
 1               5                  10

<210> SEQ ID NO 31
<211> LENGTH: 10
<212> TYPE: PRT
<213> ORGANISM: Artificial Sequence
<220> FEATURE:
<223> OTHER INFORMATION: amino acid sequence of HCDR1 of Clone HF2-16,
      HF2-22, HF2-23

<400> SEQUENCE: 31

Gly Phe Arg Ile Arg Ser His Gly Met Gln
 1               5                  10

<210> SEQ ID NO 32
<211> LENGTH: 10
<212> TYPE: PRT
<213> ORGANISM: Artificial Sequence
<220> FEATURE:
<223> OTHER INFORMATION: amino acid sequence of HCDR1 of Clone HF2-18

<400> SEQUENCE: 32

Tyr Trp Ala Phe Arg Ser His Gly Met Gln
 1               5                  10

<210> SEQ ID NO 33
<211> LENGTH: 10
<212> TYPE: PRT
<213> ORGANISM: Artificial Sequence
<220> FEATURE:
<223> OTHER INFORMATION: amino acid sequence of HCDR1 of Clone HF2-19

<400> SEQUENCE: 33

Gly Phe Ser Thr Arg Ser His Gly Met Gln
 1               5                  10
```

```
<210> SEQ ID NO 34
<211> LENGTH: 10
<212> TYPE: PRT
<213> ORGANISM: Artificial Sequence
<220> FEATURE:
<223> OTHER INFORMATION: amino acid sequence of HCDR1 of Clone HF2-20,
      HF2-25

<400> SEQUENCE: 34

Tyr Met Glu Tyr Arg Ser His Gly Met Gln
1               5                   10

<210> SEQ ID NO 35
<211> LENGTH: 17
<212> TYPE: PRT
<213> ORGANISM: Artificial Sequence
<220> FEATURE:
<223> OTHER INFORMATION: amino acid sequence of HCDR2 of Clone F

<400> SEQUENCE: 35

Gly Ile Ser Ser Asp Gly Ser Trp Thr Gly Tyr Gly Ala Ala Val Lys
1               5                   10                  15

Gly

<210> SEQ ID NO 36
<211> LENGTH: 17
<212> TYPE: PRT
<213> ORGANISM: Artificial Sequence
<220> FEATURE:
<223> OTHER INFORMATION: amino acid sequence of HCDR2 of Clone HF2-1

<400> SEQUENCE: 36

Gly Ile Ser Ser Asp Gly Ser Trp Thr Gly Tyr Gly Ala Ala Val Glu
1               5                   10                  15

Gly

<210> SEQ ID NO 37
<211> LENGTH: 17
<212> TYPE: PRT
<213> ORGANISM: Artificial Sequence
<220> FEATURE:
<223> OTHER INFORMATION: amino acid sequence of HCDR2 of Clone HF2-2

<400> SEQUENCE: 37

Gly Ile Ser Ser Asp Gly Ser Trp Glu Arg Val Gly Ala Ala Val Glu
1               5                   10                  15

Gly

<210> SEQ ID NO 38
<211> LENGTH: 17
<212> TYPE: PRT
<213> ORGANISM: Artificial Sequence
<220> FEATURE:
<223> OTHER INFORMATION: amino acid sequence of HCDR2 of Clone HF2-3,
      HF2-6, HF2-7, HF2-9, HF2-10, HF2-12, HF2-22

<400> SEQUENCE: 38

Gly Ile Ser Ser Asp Gly Ser Trp Phe Arg Val Ala Ala Ala Val Glu
1               5                   10                  15

Gly

<210> SEQ ID NO 39
<211> LENGTH: 17
<212> TYPE: PRT
```

```
<213> ORGANISM: Artificial Sequence
<220> FEATURE:
<223> OTHER INFORMATION: amino acid sequence of HCDR2 of Clone HF2-4,
      HF2-17

<400> SEQUENCE: 39

Gly Ile Ser Ser Asp Gly Ser Trp Arg Arg His Ser Ala Ala Val Glu
 1               5                  10                  15

Gly

<210> SEQ ID NO 40
<211> LENGTH: 17
<212> TYPE: PRT
<213> ORGANISM: Artificial Sequence
<220> FEATURE:
<223> OTHER INFORMATION: amino acid sequence of HCDR2 of Clone HF2-5

<400> SEQUENCE: 40

Gly Ile Ser Ser Asp Gly Ser Trp Ala Arg His Ser Ala Ala Val Glu
 1               5                  10                  15

Gly

<210> SEQ ID NO 41
<211> LENGTH: 17
<212> TYPE: PRT
<213> ORGANISM: Artificial Sequence
<220> FEATURE:
<223> OTHER INFORMATION: amino acid sequence of HCDR2 of Clone HF2-8

<400> SEQUENCE: 41

Gly Ile Ser Ser Asp Gly Ser Trp Leu Lys Leu Ser Ala Ala Val Glu
 1               5                  10                  15

Gly

<210> SEQ ID NO 42
<211> LENGTH: 17
<212> TYPE: PRT
<213> ORGANISM: Artificial Sequence
<220> FEATURE:
<223> OTHER INFORMATION: amino acid sequence of HCDR2 of Clone HF2-11,
      HF2-16, HF2-24

<400> SEQUENCE: 42

Gly Ile Ser Ser Asp Gly Ser Trp Val Lys Val Ala Ala Ala Val Glu
 1               5                  10                  15

Gly

<210> SEQ ID NO 43
<211> LENGTH: 17
<212> TYPE: PRT
<213> ORGANISM: Artificial Sequence
<220> FEATURE:
<223> OTHER INFORMATION: amino acid sequence of HCDR2 of Clone HF2-13

<400> SEQUENCE: 43

Gly Ile Ser Ser Asp Gly Ser Trp Gln Arg Val Asn Ala Ala Val Glu
 1               5                  10                  15

Gly

<210> SEQ ID NO 44
<211> LENGTH: 17
<212> TYPE: PRT
<213> ORGANISM: Artificial Sequence
<220> FEATURE:
```

```
<223> OTHER INFORMATION: amino acid sequence of HCDR2 of Clone HF2-14

<400> SEQUENCE: 44

Gly Ile Ser Ser Asp Gly Ser Trp Leu Arg Gln Asp Ala Ala Val Glu
 1               5                  10                  15

Gly

<210> SEQ ID NO 45
<211> LENGTH: 17
<212> TYPE: PRT
<213> ORGANISM: Artificial Sequence
<220> FEATURE:
<223> OTHER INFORMATION: amino acid sequence of HCDR2 of Clone HF2-15,
      HF2-19

<400> SEQUENCE: 45

Gly Ile Ser Ser Asp Gly Ser Trp Lys Ala Thr Ala Ala Ala Val Glu
 1               5                  10                  15

Gly

<210> SEQ ID NO 46
<211> LENGTH: 17
<212> TYPE: PRT
<213> ORGANISM: Artificial Sequence
<220> FEATURE:
<223> OTHER INFORMATION: amino acid sequence of HCDR2 of Clone HF2-18,
      HF2-23

<400> SEQUENCE: 46

Gly Ile Ser Ser Asp Gly Ser Trp Phe Ser Ser Ala Ala Ala Val Glu
 1               5                  10                  15

Gly

<210> SEQ ID NO 47
<211> LENGTH: 17
<212> TYPE: PRT
<213> ORGANISM: Artificial Sequence
<220> FEATURE:
<223> OTHER INFORMATION: amino acid sequence of HCDR2 of Clone HF2-20

<400> SEQUENCE: 47

Gly Ile Ser Ser Asp Gly Ser Trp Ser Arg Val Asp Ala Ala Val Glu
 1               5                  10                  15

Gly

<210> SEQ ID NO 48
<211> LENGTH: 17
<212> TYPE: PRT
<213> ORGANISM: Artificial Sequence
<220> FEATURE:
<223> OTHER INFORMATION: amino acid sequence of HCDR2 of Clone HF2-21

<400> SEQUENCE: 48

Gly Ile Ser Ser Asp Gly Ser Trp Tyr Arg Val Gln Ala Ala Val Glu
 1               5                  10                  15

Gly

<210> SEQ ID NO 49
<211> LENGTH: 17
<212> TYPE: PRT
<213> ORGANISM: Artificial Sequence
<220> FEATURE:
<223> OTHER INFORMATION: amino acid sequence of HCDR2 of Clone HF2-25
```

-continued

<400> SEQUENCE: 49

Gly Ile Ser Ser Asp Gly Ser Trp Phe Arg Met Asn Ala Ala Val Glu
 1               5                  10                  15

Gly

<210> SEQ ID NO 50
<211> LENGTH: 17
<212> TYPE: PRT
<213> ORGANISM: Artificial Sequence
<220> FEATURE:
<223> OTHER INFORMATION: amino acid sequence of HCDR2 of Clone HF2-26

<400> SEQUENCE: 50

Gly Ile Ser Ser Asp Gly Ser Trp Ile Arg Val Gln Ala Ala Val Glu
 1               5                  10                  15

Gly

<210> SEQ ID NO 51
<211> LENGTH: 21
<212> TYPE: DNA
<213> ORGANISM: Artificial Sequence
<220> FEATURE:
<223> OTHER INFORMATION: base sequence of light chain variable region
      (LCDR2)

<400> SEQUENCE: 51
tgggacgaca agcggccctc c                                             21

<210> SEQ ID NO 52
<211> LENGTH: 33
<212> TYPE: DNA
<213> ORGANISM: Artificial Sequence
<220> FEATURE:
<223> OTHER INFORMATION: base sequence of light chain variable region
      (LCDR3)

<400> SEQUENCE: 52
ggagcctggg agtactccgg cggcgtgggc atc                                33

<210> SEQ ID NO 53
<211> LENGTH: 39
<212> TYPE: DNA
<213> ORGANISM: Artificial Sequence
<220> FEATURE:
<223> OTHER INFORMATION: base sequence of light chain variable region
      (HCDR3)

<400> SEQUENCE: 53
gacttctcca ccggctacgg agccgactcc atcgacgcc                          39

<210> SEQ ID NO 54
<211> LENGTH: 106
<212> TYPE: PRT
<213> ORGANISM: Artificial Sequence
<220> FEATURE:
<223> OTHER INFORMATION: amino acid sequence of light chain variable
      region of Clone F

<400> SEQUENCE: 54

Leu Thr Gln Pro Ser Ser Val Ser Ala Asn Pro Gly Glu Thr Val Lys
 1               5                  10                  15

Ile Thr Cys Ser Gly Gly Ser Asn Ser Ala Tyr Gly Tyr Gly Trp Tyr
                20                  25                  30

Gln Gln Lys Ser Pro Gly Ser Ala Pro Val Thr Leu Ile Tyr Trp Asp 35                  40                  45
Asp Lys Arg Pro Ser Asp Ile Pro Ser Arg Phe Ser Gly Ser Ala Ser
         50                  55                  60

Gly Ser Thr Ala Thr Leu Thr Ile Thr Gly Val Arg Ala Glu Asp Glu
 65                  70                  75                  80

Ala Val Tyr Phe Cys Gly Ala Trp Glu Tyr Ser Ser Asp Val Gly Ile
                 85                  90                  95

Phe Gly Ala Gly Thr Thr Leu Thr Val Leu
            100                 105

<210> SEQ ID NO 55
<211> LENGTH: 109
<212> TYPE: PRT
<213> ORGANISM: Artificial Sequence
<220> FEATURE:
<223> OTHER INFORMATION: amino acid sequence of light chain variable
      region of Clone HF2-1, HF2-2, HF2-4, HF2-5, HF2-14, HF2-19, HF2-20

<400> SEQUENCE: 55

Asp Ile Gln Met Thr Gln Ser Pro Ser Ser Leu Ser Ala Ser Val Gly
  1               5                  10                  15

Asp Arg Val Thr Ile Thr Cys Ser Gly Gly Ser Asp Ser Ala Tyr Gly
             20                  25                  30

Tyr Gly Trp Tyr Gln Gln Lys Pro Gly Lys Ala Pro Lys Thr Leu Ile
         35                  40                  45

Tyr Trp Asp Asp Lys Arg Pro Ser Gly Val Pro Ser Arg Phe Ser Gly
     50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gly Ala Trp Glu Tyr Ser Gly Gly
                 85                  90                  95

Val Gly Ile Phe Gly Gln Gly Thr Lys Val Glu Ile Lys
            100                 105

<210> SEQ ID NO 56
<211> LENGTH: 109
<212> TYPE: PRT
<213> ORGANISM: Artificial Sequence
<220> FEATURE:
<223> OTHER INFORMATION: amino acid sequence of light chain variable
      region of Clone HF2-3

<400> SEQUENCE: 56

Asp Ile Gln Met Thr Gln Ser Pro Ser Ser Leu Ser Ala Ser Val Gly
  1               5                  10                  15

Asp Arg Val Thr Ile Thr Cys Ser Gly Gly Ser Asp Ser Ala Tyr Gly
             20                  25                  30

Tyr Gly Trp Tyr Gln Gln Lys Pro Gly Lys Ala Pro Lys Thr Leu Ile
         35                  40                  45

Tyr Trp Asp Asp Lys Arg Pro Ser Gly Ala Pro Ser Arg Phe Ser Gly
     50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gly Ala Trp Glu Tyr Ser Gly Gly
                 85                  90                  95

Val Gly Ile Phe Gly Gln Gly Thr Lys Val Glu Ile Lys
            100                 105

```
<210> SEQ ID NO 57
<211> LENGTH: 109
<212> TYPE: PRT
<213> ORGANISM: Artificial Sequence
<220> FEATURE:
<223> OTHER INFORMATION: amino acid sequence of light chain variable
      region of Clone HF2-6, HF2-7, HF2-9, HF2-10, HF2-12, HF2-21

<400> SEQUENCE: 57

Asp Ile Gln Met Thr Gln Ser Pro Ser Ser Leu Ser Ala Ser Val Gly
 1               5                  10                  15

Asp Arg Val Thr Ile Thr Cys Ser Gly Gly Ser Met Glu Pro Leu Gly
            20                  25                  30

Tyr Gly Trp Tyr Gln Gln Lys Pro Gly Lys Ala Pro Lys Thr Leu Ile
        35                  40                  45

Tyr Trp Asp Asp Lys Arg Pro Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gly Ala Trp Glu Tyr Ser Gly Gly
                85                  90                  95

Val Gly Ile Phe Gly Gln Gly Thr Lys Val Glu Ile Lys
            100                 105

<210> SEQ ID NO 58
<211> LENGTH: 109
<212> TYPE: PRT
<213> ORGANISM: Artificial Sequence
<220> FEATURE:
<223> OTHER INFORMATION: amino acid sequence of light chain variable
      region of Clone HF2-8

<400> SEQUENCE: 58

Asp Ile Gln Met Thr Gln Ser Pro Ser Ser Leu Ser Ala Ser Val Gly
 1               5                  10                  15

Asp Arg Val Thr Ile Thr Cys Ser Gly Gly Ser Thr Tyr Ser Leu Gly
            20                  25                  30

Tyr Gly Trp Tyr Gln Gln Lys Pro Gly Lys Ala Pro Lys Thr Leu Ile
        35                  40                  45

Tyr Trp Asp Asp Lys Arg Pro Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gly Ala Trp Glu Tyr Ser Gly Gly
                85                  90                  95

Val Gly Ile Phe Gly Gln Gly Thr Lys Val Glu Ile Lys
            100                 105

<210> SEQ ID NO 59
<211> LENGTH: 109
<212> TYPE: PRT
<213> ORGANISM: Artificial Sequence
<220> FEATURE:
<223> OTHER INFORMATION: amino acid sequence of light chain variable
      region of Clone HF2-11

<400> SEQUENCE: 59

Asp Ile Gln Met Thr Gln Ser Pro Ser Ser Leu Ser Ala Ser Val Gly
 1               5                  10                  15

Asp Arg Val Thr Ile Thr Cys Ser Gly Gly Ser Ser Glu Pro Leu Gly
            20                  25                  30
```

Tyr Gly Trp Tyr Gln Gln Lys Pro Gly Lys Ala Pro Lys Thr Leu Ile
            35                  40                  45

Tyr Trp Asp Asp Lys Arg Pro Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gly Ala Trp Glu Tyr Ser Gly Gly
                85                  90                  95

Val Gly Ile Phe Gly Gln Gly Thr Lys Val Glu Ile Lys
            100                 105

<210> SEQ ID NO 60
<211> LENGTH: 109
<212> TYPE: PRT
<213> ORGANISM: Artificial Sequence
<220> FEATURE:
<223> OTHER INFORMATION: amino acid sequence of light chain variable
      region of Clone HF2-13, HF2-23

<400> SEQUENCE: 60

Asp Ile Gln Met Thr Gln Ser Pro Ser Ser Leu Ser Ala Ser Val Gly
1               5                   10                  15

Asp Arg Val Thr Ile Thr Cys Ser Gly Gly Ser Asp Leu Leu Leu Gly
            20                  25                  30

Tyr Gly Trp Tyr Gln Gln Lys Pro Gly Lys Ala Pro Lys Thr Leu Ile
            35                  40                  45

Tyr Trp Asp Asp Lys Arg Pro Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gly Ala Trp Glu Tyr Ser Gly Gly
                85                  90                  95

Val Gly Ile Phe Gly Gln Gly Thr Lys Val Glu Ile Lys
            100                 105

<210> SEQ ID NO 61
<211> LENGTH: 109
<212> TYPE: PRT
<213> ORGANISM: Artificial Sequence
<220> FEATURE:
<223> OTHER INFORMATION: amino acid sequence of light chain variable
      region of Clone HF2-15, HF2-24

<400> SEQUENCE: 61

Asp Ile Gln Met Thr Gln Ser Pro Ser Ser Leu Ser Ala Ser Val Gly
1               5                   10                  15

Asp Arg Val Thr Ile Thr Cys Ser Gly Gly Ser Gln Glu Ser Leu Gly
            20                  25                  30

Tyr Gly Trp Tyr Gln Gln Lys Pro Gly Lys Ala Pro Lys Thr Leu Ile
            35                  40                  45

Tyr Trp Asp Asp Lys Arg Pro Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gly Ala Trp Glu Tyr Ser Gly Gly
                85                  90                  95

Val Gly Ile Phe Gly Gln Gly Thr Lys Val Glu Ile Lys
            100                 105

<210> SEQ ID NO 62
<211> LENGTH: 109
<212> TYPE: PRT
<213> ORGANISM: Artificial Sequence
<220> FEATURE:
<223> OTHER INFORMATION: amino acid sequence of light chain variable
      region of Clone HF2-16, HF2-17, HF2-18

<400> SEQUENCE: 62

Asp Ile Gln Met Thr Gln Ser Pro Ser Ser Leu Ser Ala Ser Val Gly
 1               5                  10                  15

Asp Arg Val Thr Ile Thr Cys Ser Gly Gly Ser Ile Glu Pro Leu Gly
            20                  25                  30

Tyr Gly Trp Tyr Gln Gln Lys Pro Gly Lys Ala Pro Lys Thr Leu Ile
        35                  40                  45

Tyr Trp Asp Asp Lys Arg Pro Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gly Ala Trp Glu Tyr Ser Gly Gly
                85                  90                  95

Val Gly Ile Phe Gly Gln Gly Thr Lys Val Glu Ile Lys
            100                 105

<210> SEQ ID NO 63
<211> LENGTH: 109
<212> TYPE: PRT
<213> ORGANISM: Artificial Sequence
<220> FEATURE:
<223> OTHER INFORMATION: amino acid sequence of light chain variable
      region of Clone HF2-22

<400> SEQUENCE: 63

Asp Ile Gln Met Thr Gln Ser Pro Ser Ser Leu Ser Ala Ser Val Gly
 1               5                  10                  15

Asp Arg Val Thr Ile Thr Cys Ser Gly Gly Ser Thr Ala Gly Val Gly
            20                  25                  30

Tyr Gly Trp Tyr Gln Gln Lys Pro Gly Lys Ala Pro Lys Thr Leu Ile
        35                  40                  45

Tyr Trp Asp Asp Lys Arg Pro Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gly Ala Trp Glu Tyr Ser Gly Gly
                85                  90                  95

Val Gly Ile Phe Gly Gln Gly Thr Lys Val Glu Ile Lys
            100                 105

<210> SEQ ID NO 64
<211> LENGTH: 109
<212> TYPE: PRT
<213> ORGANISM: Artificial Sequence
<220> FEATURE:
<223> OTHER INFORMATION: amino acid sequence of light chain variable
      region of Clone HF2-25

<400> SEQUENCE: 64

Asp Ile Gln Met Thr Gln Ser Pro Ser Ser Leu Ser Ala Ser Val Gly
 1               5                  10                  15

```
Asp Arg Val Thr Ile Thr Cys Ser Gly Gly Ser Asn Phe Pro Met Gly
             20                  25                  30

Tyr Gly Trp Tyr Gln Gln Lys Pro Gly Lys Ala Pro Lys Thr Leu Ile
         35                  40                  45

Tyr Trp Asp Asp Lys Arg Pro Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gly Ala Trp Glu Tyr Ser Gly Gly
                 85                  90                  95

Val Gly Ile Phe Gly Gln Gly Thr Lys Val Glu Ile Lys
            100                 105

<210> SEQ ID NO 65
<211> LENGTH: 109
<212> TYPE: PRT
<213> ORGANISM: Artificial Sequence
<220> FEATURE:
<223> OTHER INFORMATION: amino acid sequence of light chain variable
      region of Clone HF2-26

<400> SEQUENCE: 65

Asp Ile Gln Met Thr Gln Ser Pro Ser Ser Leu Ser Ala Ser Val Gly
 1               5                  10                  15

Asp Arg Val Thr Ile Thr Cys Thr Ala Pro Ala Asp Ser Ala Tyr Gly
             20                  25                  30

Tyr Gly Trp Tyr Gln Gln Lys Pro Gly Lys Ala Pro Lys Thr Leu Ile
         35                  40                  45

Tyr Trp Asp Asp Lys Arg Pro Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gly Ala Trp Glu Tyr Ser Gly Gly
                 85                  90                  95

Val Gly Ile Phe Gly Gln Gly Thr Lys Val Glu Ile Lys
            100                 105

<210> SEQ ID NO 66
<211> LENGTH: 318
<212> TYPE: DNA
<213> ORGANISM: Artificial Sequence
<220> FEATURE:
<223> OTHER INFORMATION: base sequence of light chain variable region of
      Clone F

<400> SEQUENCE: 66
ctgactcagc cgtcctcggt gtcagcaaac ccaggagaaa ccgtcaagat cacctgctcc      60
gggggcagta acagtgctta tggctatggc tggtatcagc agaagtctcc tggcagtgcc     120
cctgtcactc tgatctattg ggacgacaag cggccctccg acatcccttc acgattctcc     180
ggttccgcat ccggctccac agccacatta accatcactg gggtccgagc cgaggacgag     240
gctgtctatt tctgtggtgc ctgggaatac agcagcgatg ttggtatatt tggggccggg     300
acaaccctga ccgtccta                                                   318

<210> SEQ ID NO 67
<211> LENGTH: 327
<212> TYPE: DNA
<213> ORGANISM: Artificial Sequence
<220> FEATURE:
```

<223> OTHER INFORMATION: base sequence of light chain variable region of
      Clone HF2-1, HF2-2, HF2-4, HF2-5, HF2-14, HF2-19, HF2-20

<400> SEQUENCE: 67
gacatccaga tgacccagtc cccctcctcg ctgagcgcct ccgtgggcga ccgggtgacc    60
atcacctgct ccggcggctc cgactccgcc tacggctacg ctggtatca gcagaagcct   120 ggcaaggcgc ctaagacgct gatctactgg gacgacaagc ggccctccgg cgtgccttcc   180
cggttctccg gatccagatc cggcaccgac ttcaccctga ccatctcctc cctgcaacct   240
gaggacttcg ccacctacta ctgcggagcc tgggagtact ccggcggcgt gggcatcttc   300
ggccagggta ccaaggtgga gatcaag                                        327

<210> SEQ ID NO 68
<211> LENGTH: 327
<212> TYPE: DNA
<213> ORGANISM: Artificial Sequence
<220> FEATURE:
<223> OTHER INFORMATION: base sequence of light chain variable region of
      Clone HF2-3

<400> SEQUENCE: 68
gacatccaga tgacccagtc cccctcctcg ctgagcgcct ccgtgggcga ccgggtgacc    60
atcacctgct ccgcggctc cgactccgcc tacggctacg ctggtatca gcagaagcct    120 ggcaaggcgc ctaagacgct gatctactgg gacgacaagc ggccctccgg cgcgccttcc   180
cggttctccg gatccagatc cggcaccgac ttcaccctga ccatctcctc cctgcaacct   240
gaggacttcg ccacctacta ctgcggagcc tgggagtact ccggcggcgt gggcatcttc   300
ggccagggta ccaaggtgga gatcaag                                        327

<210> SEQ ID NO 69
<211> LENGTH: 327
<212> TYPE: DNA
<213> ORGANISM: Artificial Sequence
<220> FEATURE:
<223> OTHER INFORMATION: base sequence of light chain variable region of
      Clone HF2-6, HF2-7, HF2-9, HF2-10, HF2-12, HF2-21

<400> SEQUENCE: 69
gacatccaga tgacccagtc cccctcctcg ctgagcgcct ccgtgggcga ccgggtgacc    60
atcacctgct ccggcggctc catggagcct ttgggctacg ctggtatca gcagaagcct   120 ggcaaggcgc ctaagacgct gatctactgg gacgacaagc ggccctccgg cgtgccttcc   180
cggttctccg gatccagatc cggcaccgac ttcaccctga ccatctcctc cctgcaacct   240
gaggacttcg ccacctacta ctgcggagcc tgggagtact ccggcggcgt gggcatcttc   300
ggccagggta ccaaggtgga gatcaag                                        327

<210> SEQ ID NO 70
<211> LENGTH: 327
<212> TYPE: DNA
<213> ORGANISM: Artificial Sequence
<220> FEATURE:
<223> OTHER INFORMATION: base sequence of light chain variable region of
      Clone HF2-8

<400> SEQUENCE: 70
gacatccaga tgacccagtc cccctcctcg ctgagcgcct ccgtgggcga ccgggtgacc    60
atcacctgct ccggcggctc cacttatagt cttggctacg ctggtatca gcagaagcct   120 ggcaaggcgc ctaagacgct gatctactgg gacgacaagc ggccctccgg cgtgccttcc   180

```
cggttctccg gatccagatc cggcaccgac ttcaccctga ccatctcctc cctgcaacct    240
gaggacttcg ccacctacta ctgcggagcc tgggagtact ccggcggcgt gggcatcttc    300
ggccagggta ccaaggtgga gatcaag                                        327
```

```
<210> SEQ ID NO 71
<211> LENGTH: 327
<212> TYPE: DNA
<213> ORGANISM: Artificial Sequence
<220> FEATURE:
<223> OTHER INFORMATION: base sequence of light chain variable region of
      Clone HF2-11

<400> SEQUENCE: 71
gacatccaga tgacccagtc cccctcctcg ctgagcgcct ccgtgggcga ccgggtgacc     60
atcacctgct ccggcggctc cagtgagcct ctgggctacg gctggtatca gcagaagcct    120
ggcaaggcgc ctaagacgct gatctactgg gacgacaagc ggccctccgg cgtgccttcc    180
cggttctccg gatccagatc cggcaccgac ttcaccctga ccatctcctc cctgcaacct    240
gaggacttcg ccacctacta ctgcggagcc tgggagtact ccggcggcgt gggcatcttc    300
ggccagggta ccaaggtgga gatcaag                                        327
```

```
<210> SEQ ID NO 72
<211> LENGTH: 327
<212> TYPE: DNA
<213> ORGANISM: Artificial Sequence
<220> FEATURE:
<223> OTHER INFORMATION: base sequence of light chain variable region of
      Clone HF2-13, HF2-23

<400> SEQUENCE: 72
gacatccaga tgacccagtc cccctcctcg ctgagcgcct ccgtgggcga ccgggtgacc     60
atcacctgct ccggcggctc cgatctgttg ttgggctacg gctggtatca gcagaagcct    120
ggcaaggcgc ctaagacgct gatctactgg gacgacaagc ggccctccgg cgtgccttcc    180
cggttctccg gatccagatc cggcaccgac ttcaccctga ccatctcctc cctgcaacct    240
gaggacttcg ccacctacta ctgcggagcc tgggagtact ccggcggcgt gggcatcttc    300
ggccagggta ccaaggtgga gatcaag                                        327
```

```
<210> SEQ ID NO 73
<211> LENGTH: 327
<212> TYPE: DNA
<213> ORGANISM: Artificial Sequence
<220> FEATURE:
<223> OTHER INFORMATION: base sequence of light chain variable region of
      Clone HF2-15, HF2-24

<400> SEQUENCE: 73
gacatccaga tgacccagtc cccctcctcg ctgagcgcct ccgtgggcga ccgggtgacc     60
atcacctgct ccggcggctc ccaggagtct cttggctacg gctggtatca gcagaagcct    120
ggcaaggcgc ctaagacgct gatctactgg gacgacaagc ggccctccgg cgtgccttcc    180
cggttctccg gatccagatc cggcaccgac ttcaccctga ccatctcctc cctgcaacct    240
gaggacttcg ccacctacta ctgcggagcc tgggagtact ccggcggcgt gggcatcttc    300
ggccagggta ccaaggtgga gatcaag                                        327
```

```
<210> SEQ ID NO 74
<211> LENGTH: 327
```

```
<212> TYPE: DNA
<213> ORGANISM: Artificial Sequence
<220> FEATURE:
<223> OTHER INFORMATION: base sequence of light chain variable region of
      Clone HF2-16, HF2-17, HF2-18

<400> SEQUENCE: 74
gacatccaga tgacccagtc ccctcctcg ctgagcgcct ccgtgggcga ccgggtgacc      60
atcacctgct ccggcggctc cattgagcct ttgggctacg gctggtatca gcagaagcct    120
ggcaaggcgc ctaagacgct gatctactgg gacgacaagc ggcctccgg cgtgccttcc     180 cggttctccg gatccagatc cggcaccgac ttcaccctga ccatctcctc cctgcaacct    240
gaggacttcg ccacctacta ctgcggagcc tgggagtact ccggcggcgt gggcatcttc    300
ggccagggta ccaaggtgga gatcaag                                        327

<210> SEQ ID NO 75
<211> LENGTH: 327
<212> TYPE: DNA
<213> ORGANISM: Artificial Sequence
<220> FEATURE:
<223> OTHER INFORMATION: base sequence of light chain variable region of
      Clone HF2-22

<400> SEQUENCE: 75
gacatccaga tgacccagtc ccctcctcg ctgagcgcct ccgtgggcga ccgggtgacc      60
atcacctgct ccggcggctc cacggcgggt gttggctacg gctggtatca gcagaagcct    120
ggcaaggcgc ctaagacgct gatctactgg gacgacaagc ggcctccgg cgtgccttcc     180 cggttctccg gatccagatc cggcaccgac ttcaccctga ccatctcctc cctgcaacct    240
gaggacttcg ccacctacta ctgcggagcc tgggagtact ccggcggcgt gggcatcttc    300
ggccagggta ccaaggtgga gatcaag                                        327

<210> SEQ ID NO 76
<211> LENGTH: 327
<212> TYPE: DNA
<213> ORGANISM: Artificial Sequence
<220> FEATURE:
<223> OTHER INFORMATION: base sequence of light chain variable region of
      Clone HF2-25

<400> SEQUENCE: 76
gacatccaga tgacccagtc ccctcctcg ctgagcgcct ccgtgggcga ccgggtgacc      60
atcacctgct ccggcggctc caattttcct atgggctacg gctggtatca gcagaagcct    120
ggcaaggcgc ctaagacgct gatctactgg gacgacaagc ggcctccgg cgtgccttcc     180 cggttctccg gatccagatc cggcaccgac ttcaccctga ccatctcctc cctgcaacct    240
gaggacttcg ccacctacta ctgcggagcc tgggagtact ccggcggcgt gggcatcttc    300
ggccagggta ccaaggtgga gatcaag                                        327

<210> SEQ ID NO 77
<211> LENGTH: 327
<212> TYPE: DNA
<213> ORGANISM: Artificial Sequence
<220> FEATURE:
<223> OTHER INFORMATION: base sequence of light chain variable region of
      Clone HF2-26

<400> SEQUENCE: 77
gacatccaga tgacccagtc ccctcctcg ctgagcgcct ccgtgggcga ccgggtgacc      60
```

```
atcacctgca ctgcgcctgc tgactccgcc tacggctacg gctggtatca gcagaagcct    120
ggcaaggcgc ctaagacgct gatctactgg gacgacaagc ggccctccgg cgtgccttcc    180
cggttctccg gatccagatc cggcaccgac ttcaccctga ccatctcctc cctgcaacct    240
gaggacttcg ccacctacta ctgcggagcc tgggagtact ccggcggcgt gggcatcttc    300
ggccagggta ccaaggtgga gatcaag                                         327
```

<210> SEQ ID NO 78
<211> LENGTH: 122
<212> TYPE: PRT
<213> ORGANISM: Artificial Sequence
<220> FEATURE:
<223> OTHER INFORMATION: amino acid sequence of heavy chain variable
      region of Clone F

<400> SEQUENCE: 78

```
Ala Val Thr Leu His Glu Ser Gly Gly Gly Leu Gln Thr Pro Gly Gly
 1               5                  10                  15

Ala Leu Ser Leu Val Cys Lys Ala Ser Gly Phe Thr Phe Ser Ser His
            20                  25                  30

Gly Met Gln Trp Val Arg Gln Ala Pro Gly Lys Gly Leu Glu Tyr Val
        35                  40                  45

Ala Gly Ile Ser Ser Asp Gly Ser Trp Thr Gly Tyr Gly Ala Ala Val
    50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Ala Thr Tyr Tyr Cys
                85                  90                  95

Ala Arg Asp Phe Ser Thr Ser Tyr Gly Ala Asp Ser Ile Asp Ala Trp
            100                 105                 110

Gly His Gly Thr Glu Val Ile Val Ser Ser
        115                 120
```

<210> SEQ ID NO 79
<211> LENGTH: 122
<212> TYPE: PRT
<213> ORGANISM: Artificial Sequence
<220> FEATURE:
<223> OTHER INFORMATION: amino acid sequence of heavy chain variable
      region of Clone HF2-1

<400> SEQUENCE: 79

```
Glu Val Gln Leu Val Glu Ser Gly Gly Gly Leu Val Gln Pro Gly Gly
 1               5                  10                  15

Ser Leu Arg Leu Ser Cys Ala Ala Ser Asn Phe Val Phe Arg Ser His
            20                  25                  30

Gly Met Gln Trp Val Arg Gln Ala Pro Gly Lys Gly Leu Glu Tyr Val
        35                  40                  45

Ala Gly Ile Ser Ser Asp Gly Ser Trp Thr Gly Tyr Gly Ala Ala Val
    50                  55                  60

Glu Gly Arg Phe Thr Ile Ser Arg Asp Asp Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Phe Ser Thr Gly Tyr Gly Ala Asp Ser Ile Asp Ala Trp
            100                 105                 110

Gly Gln Gly Thr Leu Val Thr Val Ser Ser
        115                 120
```

```
<210> SEQ ID NO 80
<211> LENGTH: 122
<212> TYPE: PRT
<213> ORGANISM: Artificial Sequence
<220> FEATURE:
<223> OTHER INFORMATION: amino acid sequence of heavy chain variable
      region of Clone HF2-2

<400> SEQUENCE: 80
```

Glu Val Gln Leu Val Glu Ser Gly Gly Gly Leu Val Gln Pro Gly Gly
 1               5                  10                  15

Ser Leu Arg Leu Ser Cys Ala Ala Ser Arg Phe Asn Met Arg Ser His
            20                  25                  30

Gly Met Gln Trp Val Arg Gln Ala Pro Gly Lys Gly Leu Glu Tyr Val
        35                  40                  45

Ala Gly Ile Ser Ser Asp Gly Ser Trp Glu Arg Val Gly Ala Ala Val
    50                  55                  60

Glu Gly Arg Phe Thr Ile Ser Arg Asp Asp Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Phe Ser Thr Gly Tyr Gly Ala Asp Ser Ile Asp Ala Trp
            100                 105                 110

Gly Gln Gly Thr Leu Val Thr Val Ser Ser
        115                 120

```
<210> SEQ ID NO 81
<211> LENGTH: 122
<212> TYPE: PRT
<213> ORGANISM: Artificial Sequence
<220> FEATURE:
<223> OTHER INFORMATION: amino acid sequence of heavy chain variable
      region of Clone HF2-3

<400> SEQUENCE: 81
```

Glu Val Gln Leu Val Glu Ser Gly Gly Gly Leu Val Gln Pro Gly Gly
 1               5                  10                  15

Ser Leu Arg Leu Ser Cys Ala Ala Ser His Phe Asn Met Arg Ser His
            20                  25                  30

Gly Met Gln Trp Val Arg Gln Ala Pro Gly Lys Gly Leu Glu Tyr Val
        35                  40                  45

Ala Gly Ile Ser Ser Asp Gly Ser Trp Phe Arg Val Ala Ala Ala Val
    50                  55                  60

Glu Gly Arg Phe Thr Ile Ser Arg Asp Asp Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Phe Ser Thr Gly Tyr Gly Ala Asp Ser Ile Asp Ala Trp
            100                 105                 110

Gly Gln Gly Thr Leu Val Thr Val Ser Ser
        115                 120

```
<210> SEQ ID NO 82
<211> LENGTH: 122
<212> TYPE: PRT
<213> ORGANISM: Artificial Sequence
<220> FEATURE:
<223> OTHER INFORMATION: amino acid sequence of heavy chain variable
      region of Clone HF2-4
```

-continued

<400> SEQUENCE: 82

Glu Val Gln Leu Val Glu Ser Gly Gly Gly Leu Val Gln Pro Gly Gly
1               5                   10                  15

Ser Leu Arg Leu Ser Cys Ala Ala Ser Gly Trp Ser Met Arg Ser His
            20                  25                  30

Gly Met Gln Trp Val Arg Gln Ala Pro Gly Lys Gly Leu Glu Tyr Val
        35                  40                  45

Ala Gly Ile Ser Ser Asp Gly Ser Trp Arg Arg His Ser Ala Ala Val
    50                  55                  60

Glu Gly Arg Phe Thr Ile Ser Arg Asp Asp Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Phe Ser Thr Gly Tyr Gly Ala Asp Ser Ile Asp Ala Trp
            100                 105                 110

Gly Gln Gly Thr Leu Val Thr Val Ser Ser
        115                 120

<210> SEQ ID NO 83
<211> LENGTH: 122
<212> TYPE: PRT
<213> ORGANISM: Artificial Sequence
<220> FEATURE:
<223> OTHER INFORMATION: amino acid sequence of heavy chain variable
      region of Clone HF2-5

<400> SEQUENCE: 83

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Met Ile Arg Ser His
            20                  25                  30

Gly Met Gln Trp Val Arg Gln Ala Pro Gly Lys Gly Leu Glu Tyr Val
        35                  40                  45

Ala Gly Ile Ser Ser Asp Gly Ser Trp Ala Arg His Ser Ala Ala Val
    50                  55                  60

Glu Gly Arg Phe Thr Ile Ser Arg Asp Asp Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Phe Ser Thr Gly Tyr Gly Ala Asp Ser Ile Asp Ala Trp
            100                 105                 110

Gly Gln Gly Thr Leu Val Thr Val Ser Ser
        115                 120

<210> SEQ ID NO 84
<211> LENGTH: 122
<212> TYPE: PRT
<213> ORGANISM: Artificial Sequence
<220> FEATURE:
<223> OTHER INFORMATION: amino acid sequence of heavy chain variable
      region of Clone HF2-6

<400> SEQUENCE: 84

Glu Val Gln Leu Val Glu Ser Gly Gly Gly Leu Val Gln Pro Gly Gly
1               5                   10                  15

Ser Leu Arg Leu Ser Cys Ala Ala Ser Arg Phe Leu Leu Arg Ser His
            20                  25                  30

```
Gly Met Gln Trp Val Arg Gln Ala Pro Gly Lys Gly Leu Glu Tyr Val
            35                  40                  45

Ala Gly Ile Ser Ser Asp Gly Ser Trp Phe Arg Val Ala Ala Ala Val
        50                  55                  60

Glu Gly Arg Phe Thr Ile Ser Arg Asp Asp Ser Lys Asn Thr Ala Tyr
 65                  70                  75                  80

Leu Gln Met Asn Ser Leu Arg Ala Glu Asp Thr Ala Val Tyr Tyr Cys
                85                  90                  95

Ala Arg Asp Phe Ser Thr Gly Tyr Gly Ala Asp Ser Ile Asp Ala Trp
            100                 105                 110

Gly Gln Gly Thr Leu Val Thr Val Ser Ser
            115                 120
```

<210> SEQ ID NO 85
<211> LENGTH: 122
<212> TYPE: PRT
<213> ORGANISM: Artificial Sequence
<220> FEATURE:
<223> OTHER INFORMATION: amino acid sequence of heavy chain variable
      region of Clone HF2-7

<400> SEQUENCE: 85

```
Glu Val Gln Leu Val Glu Ser Gly Gly Gly Leu Val Gln Pro Gly Gly
 1               5                   10                  15

Ser Leu Arg Leu Ser Cys Ala Ala Ser Gln Phe Trp Ile Arg Ser His
            20                  25                  30

Gly Met Gln Trp Val Arg Gln Ala Pro Gly Lys Gly Leu Glu Tyr Val
            35                  40                  45

Ala Gly Ile Ser Ser Asp Gly Ser Trp Phe Arg Val Ala Ala Ala Val
        50                  55                  60

Glu Gly Arg Phe Thr Ile Ser Arg Asp Asp Ser Lys Asn Thr Ala Tyr
 65                  70                  75                  80

Leu Gln Met Asn Ser Leu Arg Ala Glu Asp Thr Ala Val Tyr Tyr Cys
                85                  90                  95

Ala Arg Asp Phe Ser Thr Gly Tyr Gly Ala Asp Ser Ile Asp Ala Trp
            100                 105                 110

Gly Gln Gly Thr Leu Val Thr Val Ser Ser
            115                 120
```

<210> SEQ ID NO 86
<211> LENGTH: 122
<212> TYPE: PRT
<213> ORGANISM: Artificial Sequence
<220> FEATURE:
<223> OTHER INFORMATION: amino acid sequence of heavy chain variable
      region of Clone HF2-8

<400> SEQUENCE: 86

```
Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe His Ile Arg Ser His
            20                  25                  30

Gly Met Gln Trp Val Arg Gln Ala Pro Gly Lys Gly Leu Glu Tyr Val
            35                  40                  45

Ala Gly Ile Ser Ser Asp Gly Ser Trp Leu Lys Leu Ser Ala Ala Val
        50                  55                  60

Glu Gly Arg Phe Thr Ile Ser Arg Asp Asp Ser Lys Asn Thr Ala Tyr
 65                  70                  75                  80
```

Leu Gln Met Asn Ser Leu Arg Ala Glu Asp Thr Ala Val Tyr Tyr Cys
                85                  90                  95

Ala Arg Asp Phe Ser Thr Gly Tyr Gly Ala Asp Ser Ile Asp Ala Trp
            100                 105                 110

Gly Gln Gly Thr Leu Val Thr Val Ser Ser
        115                 120

<210> SEQ ID NO 87
<211> LENGTH: 122
<212> TYPE: PRT
<213> ORGANISM: Artificial Sequence
<220> FEATURE:
<223> OTHER INFORMATION: amino acid sequence of heavy chain variable
      region of Clone HF2-9

<400> SEQUENCE: 87

Glu Val Gln Leu Val Glu Ser Gly Gly Gly Leu Val Gln Pro Gly Gly
1               5                   10                  15

Ser Leu Arg Leu Ser Cys Ala Ala Ser Met Phe Arg Ile Arg Ser His
            20                  25                  30

Gly Met Gln Trp Val Arg Gln Ala Pro Gly Lys Gly Leu Glu Tyr Val
        35                  40                  45

Ala Gly Ile Ser Ser Asp Gly Ser Trp Phe Arg Val Ala Ala Ala Val
    50                  55                  60

Glu Gly Arg Phe Thr Ile Ser Arg Asp Asp Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Phe Ser Thr Gly Tyr Gly Ala Asp Ser Ile Asp Ala Trp
            100                 105                 110

Gly Gln Gly Thr Leu Val Thr Val Ser Ser
        115                 120

<210> SEQ ID NO 88
<211> LENGTH: 122
<212> TYPE: PRT
<213> ORGANISM: Artificial Sequence
<220> FEATURE:
<223> OTHER INFORMATION: amino acid sequence of heavy chain variable
      region of Clone HF2-10

<400> SEQUENCE: 88

Glu Val Gln Leu Val Glu Ser Gly Gly Gly Leu Val Gln Pro Gly Gly
1               5                   10                  15

Ser Leu Arg Leu Ser Cys Ala Ala Ser Phe Gln Tyr Phe Arg Ser His
            20                  25                  30

Gly Met Gln Trp Val Arg Gln Ala Pro Gly Lys Gly Leu Glu Tyr Val
        35                  40                  45

Ala Gly Ile Ser Ser Asp Gly Ser Trp Phe Arg Val Ala Ala Ala Val
    50                  55                  60

Glu Gly Arg Phe Thr Ile Ser Arg Asp Asp Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Phe Ser Thr Gly Tyr Gly Ala Asp Ser Ile Asp Ala Trp
            100                 105                 110

Gly Gln Gly Thr Leu Val Thr Val Ser Ser
        115                 120

<210> SEQ ID NO 89
<211> LENGTH: 122
<212> TYPE: PRT
<213> ORGANISM: Artificial Sequence
<220> FEATURE:
<223> OTHER INFORMATION: amino acid sequence of heavy chain variable
      region of Clone HF2-11

<400> SEQUENCE: 89

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Leu Ile Arg Ser His
            20                  25                  30

Gly Met Gln Trp Val Arg Gln Ala Pro Gly Lys Gly Leu Glu Tyr Val
        35                  40                  45

Ala Gly Ile Ser Ser Asp Gly Ser Trp Val Lys Val Ala Ala Ala Val
    50                  55                  60

Glu Gly Arg Phe Thr Ile Ser Arg Asp Asp Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Phe Ser Thr Gly Tyr Gly Ala Asp Ser Ile Asp Ala Trp
            100                 105                 110

Gly Gln Gly Thr Leu Val Thr Val Ser Ser
        115                 120

<210> SEQ ID NO 90
<211> LENGTH: 122
<212> TYPE: PRT
<213> ORGANISM: Artificial Sequence
<220> FEATURE:
<223> OTHER INFORMATION: amino acid sequence of heavy chain variable
      region of Clone HF2-12

<400> SEQUENCE: 90

Glu Val Gln Leu Val Glu Ser Gly Gly Gly Leu Val Gln Pro Gly Gly
 1               5                  10                  15

Ser Leu Arg Leu Ser Cys Ala Ala Ser Tyr Ser Glu Val Arg Ser His
            20                  25                  30

Gly Met Gln Trp Val Arg Gln Ala Pro Gly Lys Gly Leu Glu Tyr Val
        35                  40                  45

Ala Gly Ile Ser Ser Asp Gly Ser Trp Phe Arg Val Ala Ala Ala Val
    50                  55                  60

Glu Gly Arg Phe Thr Ile Ser Arg Asp Asp Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Phe Ser Thr Gly Tyr Gly Ala Asp Ser Ile Asp Ala Trp
            100                 105                 110

Gly Gln Gly Thr Leu Val Thr Val Ser Ser
        115                 120

<210> SEQ ID NO 91
<211> LENGTH: 122
<212> TYPE: PRT
<213> ORGANISM: Artificial Sequence
<220> FEATURE:
<223> OTHER INFORMATION: amino acid sequence of heavy chain variable
      region of Clone HF2-13

<400> SEQUENCE: 91

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Leu Val Arg Ser His
            20                  25                  30

Gly Met Gln Trp Val Arg Gln Ala Pro Gly Lys Gly Leu Glu Tyr Val
        35                  40                  45

Ala Gly Ile Ser Ser Asp Gly Ser Trp Gln Arg Val Asn Ala Ala Val
    50                  55                  60

Glu Gly Arg Phe Thr Ile Ser Arg Asp Asp Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Phe Ser Thr Gly Tyr Gly Ala Asp Ser Ile Asp Ala Trp
            100                 105                 110

Gly Gln Gly Thr Leu Val Thr Val Ser Ser
        115                 120

<210> SEQ ID NO 92
<211> LENGTH: 122
<212> TYPE: PRT
<213> ORGANISM: Artificial Sequence
<220> FEATURE:
<223> OTHER INFORMATION: amino acid sequence of heavy chain variable
      region of Clone HF2-14

<400> SEQUENCE: 92

Glu Val Gln Leu Val Glu Ser Gly Gly Gly Leu Val Gln Pro Gly Gly
1               5                   10                  15

Ser Leu Arg Leu Ser Cys Ala Ala Ser His Ser Ser Ile Arg Ser His
            20                  25                  30

Gly Met Gln Trp Val Arg Gln Ala Pro Gly Lys Gly Leu Glu Tyr Val
        35                  40                  45

Ala Gly Ile Ser Ser Asp Gly Ser Trp Leu Arg Gln Asp Ala Ala Val
    50                  55                  60

Glu Gly Arg Phe Thr Ile Ser Arg Asp Asp Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Phe Ser Thr Gly Tyr Gly Ala Asp Ser Ile Asp Ala Trp
            100                 105                 110

Gly Gln Gly Thr Leu Val Thr Val Ser Ser
        115                 120

<210> SEQ ID NO 93
<211> LENGTH: 122
<212> TYPE: PRT
<213> ORGANISM: Artificial Sequence
<220> FEATURE:
<223> OTHER INFORMATION: amino acid sequence of heavy chain variable
      region of Clone HF2-15

<400> SEQUENCE: 93

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Val Val Arg Ser His
            20                  25                  30

Gly Met Gln Trp Val Arg Gln Ala Pro Gly Lys Gly Leu Glu Tyr Val

```
                35                  40                  45
Ala Gly Ile Ser Ser Asp Gly Ser Trp Lys Ala Thr Ala Ala Ala Val
         50                  55                  60
Glu Gly Arg Phe Thr Ile Ser Arg Asp Asp Ser Lys Asn Thr Ala Tyr
 65                  70                  75                  80
Leu Gln Met Asn Ser Leu Arg Ala Glu Asp Thr Ala Val Tyr Tyr Cys
                 85                  90                  95
Ala Arg Asp Phe Ser Thr Gly Tyr Gly Ala Asp Ser Ile Asp Ala Trp
             100                 105                 110
Gly Gln Gly Thr Leu Val Thr Val Ser Ser
         115                 120

<210> SEQ ID NO 94
<211> LENGTH: 122
<212> TYPE: PRT
<213> ORGANISM: Artificial Sequence
<220> FEATURE:
<223> OTHER INFORMATION: amino acid sequence of heavy chain variable
      region of Clone HF2-16

<400> SEQUENCE: 94

Glu Val Gln Leu Val Glu Ser Gly Gly Gly Leu Val Gln Pro Gly Gly
  1               5                  10                  15
Ser Leu Arg Leu Ser Cys Ala Ala Ser Gly Phe Arg Ile Arg Ser His
             20                  25                  30
Gly Met Gln Trp Val Arg Gln Ala Pro Gly Lys Gly Leu Glu Tyr Val
         35                  40                  45
Ala Gly Ile Ser Ser Asp Gly Ser Trp Val Lys Val Ala Ala Ala Val
         50                  55                  60
Glu Gly Arg Phe Thr Ile Ser Arg Asp Asp Ser Lys Asn Thr Ala Tyr
 65                  70                  75                  80
Leu Gln Met Asn Ser Leu Arg Ala Glu Asp Thr Ala Val Tyr Tyr Cys
                 85                  90                  95
Ala Arg Asp Phe Ser Thr Gly Tyr Gly Ala Asp Ser Ile Asp Ala Trp
             100                 105                 110
Gly Gln Gly Thr Leu Val Thr Val Ser Ser
         115                 120

<210> SEQ ID NO 95
<211> LENGTH: 122
<212> TYPE: PRT
<213> ORGANISM: Artificial Sequence
<220> FEATURE:
<223> OTHER INFORMATION: amino acid sequence of heavy chain variable
      region of Clone HF2-17

<400> SEQUENCE: 95

Glu Val Gln Leu Val Glu Ser Gly Gly Gly Leu Val Gln Pro Gly Gly
  1               5                  10                  15
Ser Leu Arg Leu Ser Cys Ala Ala Ser Gly Phe Met Ile Arg Ser His
             20                  25                  30
Gly Met Gln Trp Val Arg Gln Ala Pro Gly Lys Gly Leu Glu Tyr Val
         35                  40                  45
Ala Gly Ile Ser Ser Asp Gly Ser Trp Arg Arg His Ser Ala Ala Val
         50                  55                  60
Glu Gly Arg Phe Thr Ile Ser Arg Asp Asp Ser Lys Asn Thr Ala Tyr
 65                  70                  75                  80
Leu Gln Met Asn Ser Leu Arg Ala Glu Asp Thr Ala Val Tyr Tyr Cys
```

85                  90                  95

Ala Arg Asp Phe Ser Thr Gly Tyr Gly Ala Asp Ser Ile Asp Ala Trp
            100                 105                 110

Gly Gln Gly Thr Leu Val Thr Val Ser Ser
        115                 120

<210> SEQ ID NO 96
<211> LENGTH: 122
<212> TYPE: PRT
<213> ORGANISM: Artificial Sequence
<220> FEATURE:
<223> OTHER INFORMATION: amino acid sequence of heavy chain variable
      region of Clone HF2-18

<400> SEQUENCE: 96

Glu Val Gln Leu Val Glu Ser Gly Gly Gly Leu Val Gln Pro Gly Gly
 1               5                  10                  15

Ser Leu Arg Leu Ser Cys Ala Ala Ser Tyr Trp Ala Phe Arg Ser His
            20                  25                  30

Gly Met Gln Trp Val Arg Gln Ala Pro Gly Lys Gly Leu Glu Tyr Val
        35                  40                  45

Ala Gly Ile Ser Ser Asp Gly Ser Trp Phe Ser Ala Ala Ala Val
    50                  55                  60

Glu Gly Arg Phe Thr Ile Ser Arg Asp Asp Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Phe Ser Thr Gly Tyr Gly Ala Asp Ser Ile Asp Ala Trp
            100                 105                 110

Gly Gln Gly Thr Leu Val Thr Val Ser Ser
        115                 120

<210> SEQ ID NO 97
<211> LENGTH: 122
<212> TYPE: PRT
<213> ORGANISM: Artificial Sequence
<220> FEATURE:
<223> OTHER INFORMATION: amino acid sequence of heavy chain variable
      region of Clone HF2-19

<400> SEQUENCE: 97

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Ser Thr Arg Ser His
            20                  25                  30

Gly Met Gln Trp Val Arg Gln Ala Pro Gly Lys Gly Leu Glu Tyr Val
        35                  40                  45

Ala Gly Ile Ser Ser Asp Gly Ser Trp Lys Ala Thr Ala Ala Ala Val
    50                  55                  60

Glu Gly Arg Phe Thr Ile Ser Arg Asp Asp Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Phe Ser Thr Gly Tyr Gly Ala Asp Ser Ile Asp Ala Trp
            100                 105                 110

Gly Gln Gly Thr Leu Val Thr Val Ser Ser
        115                 120

```
<210> SEQ ID NO 98
<211> LENGTH: 122
<212> TYPE: PRT
<213> ORGANISM: Artificial Sequence
<220> FEATURE:
<223> OTHER INFORMATION: amino acid sequence of heavy chain variable
      region of Clone HF2-20

<400> SEQUENCE: 98
```

Glu Val Gln Leu Val Glu Ser Gly Gly Leu Val Gln Pro Gly Gly
1               5                   10                  15

Ser Leu Arg Leu Ser Cys Ala Ala Ser Tyr Met Glu Tyr Arg Ser His
            20                  25                  30

Gly Met Gln Trp Val Arg Gln Ala Pro Gly Lys Gly Leu Glu Tyr Val
        35                  40                  45

Ala Gly Ile Ser Ser Asp Gly Ser Trp Ser Arg Val Asp Ala Ala Val
    50                  55                  60

Glu Gly Arg Phe Thr Ile Ser Arg Asp Asp Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Phe Ser Thr Gly Tyr Gly Ala Asp Ser Ile Asp Ala Trp
            100                 105                 110

Gly Gln Gly Thr Leu Val Thr Val Ser Ser
        115                 120

```
<210> SEQ ID NO 99
<211> LENGTH: 122
<212> TYPE: PRT
<213> ORGANISM: Artificial Sequence
<220> FEATURE:
<223> OTHER INFORMATION: amino acid sequence of heavy chain variable
      region of Clone HF2-21

<400> SEQUENCE: 99
```

Glu Val Gln Leu Val Glu Ser Gly Gly Leu Val Gln Pro Gly Gly
1               5                   10                  15

Ser Leu Arg Leu Ser Cys Ala Ala Ser Phe Gln Tyr Phe Arg Ser His
            20                  25                  30

Gly Met Gln Trp Val Arg Gln Ala Pro Gly Lys Gly Leu Glu Tyr Val
        35                  40                  45

Ala Gly Ile Ser Ser Asp Gly Ser Trp Tyr Arg Val Gln Ala Ala Val
    50                  55                  60

Glu Gly Arg Phe Thr Ile Ser Arg Asp Asp Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Phe Ser Thr Gly Tyr Gly Ala Asp Ser Ile Asp Ala Trp
            100                 105                 110

Gly Gln Gly Thr Leu Val Thr Val Ser Ser
        115                 120

```
<210> SEQ ID NO 100
<211> LENGTH: 122
<212> TYPE: PRT
<213> ORGANISM: Artificial Sequence
<220> FEATURE:
<223> OTHER INFORMATION: amino acid sequence of heavy chain variable
      region of Clone HF2-22

<400> SEQUENCE: 100
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Arg Ile Arg Ser His
            20                  25                  30

Gly Met Gln Trp Val Arg Gln Ala Pro Gly Lys Gly Leu Glu Tyr Val
        35                  40                  45

Ala Gly Ile Ser Ser Asp Gly Ser Trp Phe Arg Val Ala Ala Ala Val
    50                  55                  60

Glu Gly Arg Phe Thr Ile Ser Arg Asp Asp Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Phe Ser Thr Gly Tyr Gly Ala Asp Ser Ile Asp Ala Trp
            100                 105                 110

Gly Gln Gly Thr Leu Val Thr Val Ser Ser
        115                 120

<210> SEQ ID NO 101
<211> LENGTH: 122
<212> TYPE: PRT
<213> ORGANISM: Artificial Sequence
<220> FEATURE:
<223> OTHER INFORMATION: amino acid sequence of heavy chain variable
      region of Clone HF2-23

<400> SEQUENCE: 101

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Arg Ile Arg Ser His
            20                  25                  30

Gly Met Gln Trp Val Arg Gln Ala Pro Gly Lys Gly Leu Glu Tyr Val
        35                  40                  45

Ala Gly Ile Ser Ser Asp Gly Ser Trp Phe Ser Ala Ala Ala Ala Val
    50                  55                  60

Glu Gly Arg Phe Thr Ile Ser Arg Asp Asp Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Phe Ser Thr Gly Tyr Gly Ala Asp Ser Ile Asp Ala Trp
            100                 105                 110

Gly Gln Gly Thr Leu Val Thr Val Ser Ser
        115                 120

<210> SEQ ID NO 102
<211> LENGTH: 122
<212> TYPE: PRT
<213> ORGANISM: Artificial Sequence
<220> FEATURE:
<223> OTHER INFORMATION: amino acid sequence of heavy chain variable
      region of Clone HF2-24

<400> SEQUENCE: 102

Glu Val Gln Leu Val Glu Ser Gly Gly Gly Leu Val Gln Pro Gly Gly
1               5                   10                  15

Ser Leu Arg Leu Ser Cys Ala Ala Ser Arg Phe Asn Met Arg Ser His
            20                  25                  30

Gly Met Gln Trp Val Arg Gln Ala Pro Gly Lys Gly Leu Glu Tyr Val
        35                  40                  45

```
Ala Gly Ile Ser Ser Asp Gly Ser Trp Val Lys Val Ala Ala Val
    50                  55                  60

Glu Gly Arg Phe Thr Ile Ser Arg Asp Asp Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Phe Ser Thr Gly Tyr Gly Ala Asp Ser Ile Asp Ala Trp
            100                 105                 110

Gly Gln Gly Thr Leu Val Thr Val Ser Ser
        115                 120

<210> SEQ ID NO 103
<211> LENGTH: 122
<212> TYPE: PRT
<213> ORGANISM: Artificial Sequence
<220> FEATURE:
<223> OTHER INFORMATION: amino acid sequence of heavy chain variable
      region of Clone HF2-25

<400> SEQUENCE: 103

Glu Val Gln Leu Val Glu Ser Gly Gly Gly Leu Val Gln Pro Gly Gly
1               5                   10                  15

Ser Leu Arg Leu Ser Cys Ala Ala Ser Tyr Met Glu Tyr Arg Ser His
            20                  25                  30

Gly Met Gln Trp Val Arg Gln Ala Pro Gly Lys Gly Leu Glu Tyr Val
        35                  40                  45

Ala Gly Ile Ser Ser Asp Gly Ser Trp Phe Arg Met Asn Ala Ala Val
    50                  55                  60

Glu Gly Arg Phe Thr Ile Ser Arg Asp Asp Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Phe Ser Thr Gly Tyr Gly Ala Asp Ser Ile Asp Ala Trp
            100                 105                 110

Gly Gln Gly Thr Leu Val Thr Val Ser Ser
        115                 120

<210> SEQ ID NO 104
<211> LENGTH: 122
<212> TYPE: PRT
<213> ORGANISM: Artificial Sequence
<220> FEATURE:
<223> OTHER INFORMATION: amino acid sequence of heavy chain variable
      region of Clone HF2-26

<400> SEQUENCE: 104

Glu Val Gln Leu Val Glu Ser Gly Gly Gly Leu Val Gln Pro Gly Gly
1               5                   10                  15

Ser Leu Arg Leu Ser Cys Ala Ala Ser Arg Phe Asn Met Arg Ser His
            20                  25                  30

Gly Met Gln Trp Val Arg Gln Ala Pro Gly Lys Gly Leu Glu Tyr Val
        35                  40                  45

Ala Gly Ile Ser Ser Asp Gly Ser Trp Ile Arg Val Gln Ala Ala Val
    50                  55                  60

Glu Gly Arg Phe Thr Ile Ser Arg Asp Asp Ser Lys Asn Thr Ala Tyr
65                  70                  75                  80

Leu Gln Met Asn Ser Leu Arg Ala Glu Asp Thr Ala Val Tyr Tyr Cys
                85                  90                  95
```

Ala Arg Asp Phe Ser Thr Gly Tyr Gly Ala Asp Ser Ile Asp Ala Trp
            100                 105                 110

Gly Gln Gly Thr Leu Val Thr Val Ser Ser
            115                 120

<210> SEQ ID NO 105
<211> LENGTH: 366
<212> TYPE: DNA
<213> ORGANISM: Artificial Sequence
<220> FEATURE:
<223> OTHER INFORMATION: base sequence of heavy chain variable region of
      Clone F

<400> SEQUENCE: 105
gccgtgacgt tgcacgagtc cggggggcggc ctccagacgc cgggaggagc gctcagcctc    60
gtctgcaagg cctccgggtt caccttcagc agccatggca tgcagtgggt gcgacaggcg   120
cccggcaagg ggctgagta tgtcgcgggt attagtagtg atggtagttg acaggctac     180 ggggcggcgg tgaagggccg tgccaccatc tcgaggaca acgggcagag cacagtgagg   240
ctgcagctga caacctcag ggcagaggac accgccacct actactgcgc cagagatttt    300
agtactagtt atggcgctga tagtatcgac gcatggggcc acgggaccga agtcatcgtc    360
tcctcc                                                              366

<210> SEQ ID NO 106
<211> LENGTH: 366
<212> TYPE: DNA
<213> ORGANISM: Artificial Sequence
<220> FEATURE:
<223> OTHER INFORMATION: base sequence of heavy chain variable region of
      Clone HF2-1

<400> SEQUENCE: 106
gaggtgcagc tggtggagtc tggcggcgga ctggtgcagc ctggcggaag cttgcggctg    60
tcctgcgccg cctccaattt tgtgtttagg tcccacggca tgcagtgggt gcggcaggcc   120
cctggcaagg gcctcgagta cgtggccggc atctcctccg acggctcctg gaccggctac   180
ggagccgccg tggagggccg gttcaccatc tcccgcgacg actccaagaa caccgcctac   240
ctgcagatga actccctgcg ggccgaggac accgccgtgt actactgcgc cagagacttc   300
tccaccggct acggagccga ctccatcgac gcctggggcc agggcacact agtgaccgtg   360
tcctcc                                                              366

<210> SEQ ID NO 107
<211> LENGTH: 366
<212> TYPE: DNA
<213> ORGANISM: Artificial Sequence
<220> FEATURE:
<223> OTHER INFORMATION: base sequence of heavy chain variable region of
      Clone HF2-2

<400> SEQUENCE: 107
gaggtgcagc tggtggagtc tggcggcgga ctggtgcagc ctggcggaag cttgcggctg    60
tcctgcgccg cctcccgttt taatatgcgg tcccacggca tgcagtgggt gcggcaggcc   120
cctggcaagg gcctcgagta cgtggccggc atctcctccg acggctcctg ggagagggtt   180
ggggccgccg tggagggccg gttcaccatc tcccgcgacg actccaagaa caccgcctac   240
ctgcagatga actccctgcg ggccgaggac accgccgtgt actactgcgc cagagacttc   300
tccaccggct acggagccga ctccatcgac gcctggggcc agggcacact agtgaccgtg   360

```
tcctcc                                                                  366

<210> SEQ ID NO 108
<211> LENGTH: 366
<212> TYPE: DNA
<213> ORGANISM: Artificial Sequence
<220> FEATURE:
<223> OTHER INFORMATION: base sequence of heavy chain variable region of
      Clone HF2-3

<400> SEQUENCE: 108
gaggtgcagc tggtggagtc tggcggcgga ctggtgcagc ctggcggaag cttgcggctg    60
tcctgcgccg cctcccattt taatatgcgg tcccacggca tgcagtgggt gcggcaggcc   120
cctggcaagg gcctcgagta cgtggccggc atctcctccg acggctcctg gtttcggtt    180 gctgccgccg tggagggccg gttcaccatc tcccgcgacg actccaagaa caccgcctac   240
ctgcagatga actccctgcg ggccgaggac accgccgtgt actactgcgc cagagacttc   300
tccaccggct acgagccgga ctccatcgac gcctggggcc agggcacact agtgaccgtg   360
tcctcc                                                                  366

<210> SEQ ID NO 109
<211> LENGTH: 366
<212> TYPE: DNA
<213> ORGANISM: Artificial Sequence
<220> FEATURE:
<223> OTHER INFORMATION: base sequence of heavy chain variable region of
      Clone HF2-4

<400> SEQUENCE: 109
gaggtgcagc tggtggagtc tggcggcgga ctggtgcagc ctggcggaag cttgcggctg    60
tcctgcgccg cctccgggtg gagtatgcgt tcccacggca tgcagtgggt gcggcaggcc   120
cctggcaagg gcctcgagta cgtggccggc atctcctccg acggctcctg gaggaggcat   180
agtgccgccg tggagggccg gttcaccatc tcccgcgacg actccaagaa caccgcctac   240
ctgcagatga actccctgcg ggccgaggac accgccgtgt actactgcgc cagagacttc   300
tccaccggct acgagccgga ctccatcgac gcctggggcc agggcacact agtgaccgtg   360
tcctcc                                                                  366

<210> SEQ ID NO 110
<211> LENGTH: 366
<212> TYPE: DNA
<213> ORGANISM: Artificial Sequence
<220> FEATURE:
<223> OTHER INFORMATION: base sequence of heavy chain variable region of
      Clone HF2-5

<400> SEQUENCE: 110
gaggtgcagc tggtggagtc tggcggcgga ctggtgcagc ctggcggaag cttgcggctg    60
tcctgcgccg cctccggttt tatgattcgt tcccacggca tgcagtgggt gcggcaggcc   120
cctggcaagg gcctcgagta cgtggccggc atctcctccg acggctcctg ggcgcggcat   180
tcggccgccg tggagggccg gttcaccatc tcccgcgacg actccaagaa caccgcctac   240
ctgcagatga actccctgcg ggccgaggac accgccgtgt actactgcgc cagagacttc   300
tccaccggct acgagccgga ctccatcgac gcctggggcc agggcacact agtgaccgtg   360
tcctcc                                                                  366
```

<210> SEQ ID NO 111
<211> LENGTH: 366
<212> TYPE: DNA
<213> ORGANISM: Artificial Sequence
<220> FEATURE:
<223> OTHER INFORMATION: base sequence of heavy chain variable region of Clone HF2-6

<400> SEQUENCE: 111

```
gaggtgcagc tggtggagtc tggcggcgga ctggtgcagc ctggcggaag cttgcggctg      60
tcctgcgccg cctccgggtt tcttctgcgt tcccacggca tgcagtgggt gcggcaggcc     120
cctggcaagg gcctcgagta cgtggccggc atctcctccg acggctcctg gtttcgggtt     180
gctgccgccg tggagggccg gttcaccatc tcccgcgacg actccaagaa caccgcctac     240
ctgcagatga actccctgcg ggccgaggac accgccgtgt actactgcgc cagagacttc     300
tccaccggct acggagccga ctccatcgac gcctggggcc agggcacact agtgaccgtg     360
tcctcc                                                                 366
```

<210> SEQ ID NO 112
<211> LENGTH: 366
<212> TYPE: DNA
<213> ORGANISM: Artificial Sequence
<220> FEATURE:
<223> OTHER INFORMATION: base sequence of heavy chain variable region of Clone HF2-7

<400> SEQUENCE: 112

```
gaggtgcagc tggtggagtc tggcggcgga ctggtgcagc ctggcggaag cttgcggctg      60
tcctgcgccg cctcccagtt ttggattagg tcccacggca tgcagtgggt gcggcaggcc     120
cctggcaagg gcctcgagta cgtggccggc atctcctccg acggctcctg gtttcgggtt     180
gctgccgccg tggagggccg gttcaccatc tcccgcgacg actccaagaa caccgcctac     240
ctgcagatga actccctgcg ggccgaggac accgccgtgt actactgcgc cagagacttc     300
tccaccggct acggagccga ctccatcgac gcctggggcc agggcacact agtgaccgtg     360
tcctcc                                                                 366
```

<210> SEQ ID NO 113
<211> LENGTH: 366
<212> TYPE: DNA
<213> ORGANISM: Artificial Sequence
<220> FEATURE:
<223> OTHER INFORMATION: base sequence of heavy chain variable region of Clone HF2-8

<400> SEQUENCE: 113

```
gaggtgcagc tggtggagtc tggcggcgga ctggtgcagc ctggcggaag cttgcggctg      60
tcctgcgccg cctccgggtt tcatattagg tcccacggca tgcagtgggt gcggcaggcc     120
cctggcaagg gcctcgagta cgtggccggc atctcctccg acggctcctg gcttaagctg     180
agtgccgccg tggagggccg gttcaccatc tcccgcgacg actccaagaa caccgcctac     240
ctgcagatga actccctgcg ggccgaggac accgccgtgt actactgcgc cagagacttc     300
tccaccggct acggagccga ctccatcgac gcctggggcc agggcacact agtgaccgtg     360
tcctcc                                                                 366
```

<210> SEQ ID NO 114
<211> LENGTH: 366
<212> TYPE: DNA
<213> ORGANISM: Artificial Sequence
<220> FEATURE:
<223> OTHER INFORMATION: base sequence of heavy chain variable region of Clone HF2- 9

<400> SEQUENCE: 114

```
gaggtgcagc tggtggagtc tggcggcgga ctggtgcagc ctggcggaag cttgcggctg      60
tcctgcgccg cctccatgtt taggattcgg tcccacggca tgcagtgggt gcggcaggcc     120
cctggcaagg gcctcgagta cgtggccggc atctcctccg acggctcctg gtttcgggtt     180
gctgccgccg tggagggccg gttcaccatc tcccgcgacg actccaagaa caccgcctac     240
ctgcagatga actccctgcg ggccgaggac accgccgtgt actactgcgc cagagacttc     300
tccaccggct acggagccga ctccatcgac gcctggggcc agggcacact agtgaccgtg     360
tcctcc                                                                 366
```

<210> SEQ ID NO 115
<211> LENGTH: 366
<212> TYPE: DNA
<213> ORGANISM: Artificial Sequence
<220> FEATURE:
<223> OTHER INFORMATION: base sequence of heavy chain variable region of Clone HF2-10

<400> SEQUENCE: 115

```
gaggtgcagc tggtggagtc tggcggcgga ctggtgcagc ctggcggaag cttgcggctg      60
tcctgcgccg cctcctttca gtattttcgt tcccacggca tgcagtgggt gcggcaggcc     120
cctggcaagg gcctcgagta cgtggccggc atctcctccg acggctcctg gtttcgggtt     180
gctgccgccg tggagggccg gttcaccatc tcccgcgacg actccaagaa caccgcctac     240
ctgcagatga actccctgcg ggccgaggac accgccgtgt actactgcgc cagagacttc     300
tccaccggct acggagccga ctccatcgac gcctggggcc agggcacact agtgaccgtg     360
tcctcc                                                                 366
```

<210> SEQ ID NO 116
<211> LENGTH: 366
<212> TYPE: DNA
<213> ORGANISM: Artificial Sequence
<220> FEATURE:
<223> OTHER INFORMATION: base sequence of heavy chain variable region of Clone HF2-11

<400> SEQUENCE: 116

```
gaggtgcagc tggtggagtc tggcggcgga ctggtgcagc ctggcggaag cttgcggctg      60
tcctgcgccg cctccggttt tcttattagg tcccacggca tgcagtgggt gcggcaggcc     120
cctggcaagg gcctcgagta cgtggccggc atctcctccg acggctcctg ggtgaaggtg     180
gcggccgccg tggagggccg gttcaccatc tcccgcgacg actccaagaa caccgcctac     240
ctgcagatga actccctgcg ggccgaggac accgccgtgt actactgcgc cagagacttc     300
tccaccggct acggagccga ctccatcgac gcctggggcc agggcacact agtgaccgtg     360
tcctcc                                                                 366
```

<210> SEQ ID NO 117
<211> LENGTH: 366
<212> TYPE: DNA
<213> ORGANISM: Artificial Sequence
<220> FEATURE:
<223> OTHER INFORMATION: base sequence of heavy chain variable region of Clone HF2-12

<400> SEQUENCE: 117

```
gaggtgcagc tggtggagtc tggcggcgga ctggtgcagc ctggcggaag cttgcggctg      60
tcctgcgccg cctcctatag tgaggttcgt tcccacggca tgcagtgggt gcggcaggcc     120
cctggcaagg gctcgagta cgtggccggc atctcctccg acggctcctg gtttcgggtt      180
gctgccgccg tggagggccg gttcaccatc tcccgcgacg actccaagaa caccgcctac     240
ctgcagatga actccctgcg ggccgaggac accgccgtgt actactgcgc cagagacttc     300
tccaccggct acggagccga ctccatcgac gcctggggcc agggcacact agtgaccgtg     360
tcctcc                                                                 366
```

<210> SEQ ID NO 118
<211> LENGTH: 366
<212> TYPE: DNA
<213> ORGANISM: Artificial Sequence
<220> FEATURE:
<223> OTHER INFORMATION: base sequence of heavy chain variable region of Clone HF2-13

<400> SEQUENCE: 118

```
gaggtgcagc tggtggagtc tggcggcgga ctggtgcagc ctggcggaag cttgcggctg      60
tcctgcgccg cctccggttt tcttgtgcgt cccacggca tgcagtgggt gcggcaggcc      120
cctggcaagg gctcgagta cgtggccggc atctcctccg acggctcctg gcagcgtgtg      180
aatgccgccg tggagggccg gttcaccatc tcccgcgacg actccaagaa caccgcctac     240
ctgcagatga actccctgcg ggccgaggac accgccgtgt actactgcgc cagagacttc     300
tccaccggct acggagccga ctccatcgac gcctggggcc agggcacact agtgaccgtg     360
tcctcc                                                                 366
```

<210> SEQ ID NO 119
<211> LENGTH: 366
<212> TYPE: DNA
<213> ORGANISM: Artificial Sequence
<220> FEATURE:
<223> OTHER INFORMATION: base sequence of heavy chain variable region of Clone HF2-14

<400> SEQUENCE: 119

```
gaggtgcagc tggtggagtc tggcggcgga ctggtgcagc ctggcggaag cttgcggctg      60
tcctgcgccg cctcccatag ttcgattagg tcccacggca tgcagtgggt gcggcaggcc     120
cctggcaagg gctcgagta cgtggccggc atctcctccg acggctcctg gcttaggcag      180
gatgccgccg tggagggccg gttcaccatc tcccgcgacg actccaagaa caccgcctac     240
ctgcagatga actccctgcg ggccgaggac accgccgtgt actactgcgc cagagacttc     300
tccaccggct acggagccga ctccatcgac gcctggggcc agggcacact agtgaccgtg     360
tcctcc                                                                 366
```

<210> SEQ ID NO 120
<211> LENGTH: 366
<212> TYPE: DNA
<213> ORGANISM: Artificial Sequence
<220> FEATURE:
<223> OTHER INFORMATION: base sequence of heavy chain variable region of Clone HF2-15

<400> SEQUENCE: 120

```
gaggtgcagc tggtggagtc tggcggcgga ctggtgcagc ctggcggaag cttgcggctg      60
```

```
tcctgcgccg cctccggttt tgtggttagg tcccacggca tgcagtgggt gcggcaggcc      120
cctggcaagg gcctcgagta cgtggccggc atctcctccg acggctcctg gaaggctacg      180
gcggccgccg tggagggccg gttcaccatc tcccgcgacg actccaagaa caccgcctac      240
ctgcagatga actccctgcg ggccgaggac accgccgtgt actactgcgc cagagacttc      300
tccaccggct acggagccga ctccatcgac gcctggggcc agggcacact agtgaccgtg      360
tcctcc                                                                 366
```

<210> SEQ ID NO 121
<211> LENGTH: 366
<212> TYPE: DNA
<213> ORGANISM: Artificial Sequence
<220> FEATURE:
<223> OTHER INFORMATION: base sequence of heavy chain variable region of Clone HF2-16

<400> SEQUENCE: 121

```
gaggtgcagc tggtggagtc tggcggcgga ctggtgcagc ctggcggaag cttgcggctg       60
tcctgcgccg cctccggttt tcgtattagg tcccacggca tgcagtgggt gcggcaggcc      120
cctggcaagg gcctcgagta cgtggccggc atctcctccg acggctcctg ggtgaaggtg      180
gcggccgccg tggagggccg gttcaccatc tcccgcgacg actccaagaa caccgcctac      240
ctgcagatga actccctgcg ggccgaggac accgccgtgt actactgcgc cagagacttc      300
tccaccggct acggagccga ctccatcgac gcctggggcc agggcacact agtgaccgtg      360
tcctcc                                                                 366
```

<210> SEQ ID NO 122
<211> LENGTH: 366
<212> TYPE: DNA
<213> ORGANISM: Artificial Sequence
<220> FEATURE:
<223> OTHER INFORMATION: base sequence of heavy chain variable region of Clone HF2-17

<400> SEQUENCE: 122

```
gaggtgcagc tggtggagtc tggcggcgga ctggtgcagc ctggcggaag cttgcggctg       60
tcctgcgccg cctccggttt tatgattcgt tcccacggca tgcagtgggt gcggcaggcc      120
cctggcaagg gcctcgagta cgtggccggc atctcctccg acggctcctg gaggaggcat      180
agtgccgccg tggagggccg gttcaccatc tcccgcgacg actccaagaa caccgcctac      240
ctgcagatga actccctgcg ggccgaggac accgccgtgt actactgcgc cagagacttc      300
tccaccggct acggagccga ctccatcgac gcctggggcc agggcacact agtgaccgtg      360
tcctcc                                                                 366
```

<210> SEQ ID NO 123
<211> LENGTH: 366
<212> TYPE: DNA
<213> ORGANISM: Artificial Sequence
<220> FEATURE:
<223> OTHER INFORMATION: base sequence of heavy chain variable region of Clone HF2-18

<400> SEQUENCE: 123

```
gaggtgcagc tggtggagtc tggcggcgga ctggtgcagc ctggcggaag cttgcggctg       60
tcctgcgccg cctcctattg ggcgtttagg tcccacggca tgcagtgggt gcggcaggcc      120
cctggcaagg gcctcgagta cgtggccggc atctcctccg acggctcctg gttttctagt      180
```

```
gcggccgccg tggagggccg gttcaccatc tcccgcgacg actccaagaa caccgcctac    240
ctgcagatga actccctgcg ggccgaggac accgccgtgt actactgcgc cagagacttc    300
tccaccggct acggagccga ctccatcgac gcctggggcc agggcacact agtgaccgtg    360
tcctcc                                                               366
```

<210> SEQ ID NO 124
<211> LENGTH: 366
<212> TYPE: DNA
<213> ORGANISM: Artificial Sequence
<220> FEATURE:
<223> OTHER INFORMATION: base sequence of heavy chain variable region of
      Clone HF2-19

<400> SEQUENCE: 124

```
gaggtgcagc tggtggagtc tggcggcgga ctggtgcagc ctggcggaag cttgcggctg     60
tcctgcgccg cctccgggtt tagtacgcgg tcccacggca tgcagtgggt gcggcaggcc    120
cctggcaagg gcctcgagta cgtggccggc atctcctccg acggctcctg gaaggctacg    180
gcggccgccg tggagggccg gttcaccatc tcccgcgacg actccaagaa caccgcctac    240
ctgcagatga actccctgcg ggccgaggac accgccgtgt actactgcgc cagagacttc    300
tccaccggct acggagccga ctccatcgac gcctggggcc agggcacact agtgaccgtg    360
tcctcc                                                               366
```

<210> SEQ ID NO 125
<211> LENGTH: 366
<212> TYPE: DNA
<213> ORGANISM: Artificial Sequence
<220> FEATURE:
<223> OTHER INFORMATION: base sequence of heavy chain variable region of
      Clone HF2-20

<400> SEQUENCE: 125

```
gaggtgcagc tggtggagtc tggcggcgga ctggtgcagc ctggcggaag cttgcggctg     60
tcctgcgccg cctcctatat ggagtatagg tcccacggca tgcagtgggt gcggcaggcc    120
cctggcaagg gcctcgagta cgtggccggc atctcctccg acggctcctg gtcgcgggtg    180
gatgccgccg tggagggccg gttcaccatc tcccgcgacg actccaagaa caccgcctac    240
ctgcagatga actccctgcg ggccgaggac accgccgtgt actactgcgc cagagacttc    300
tccaccggct acggagccga ctccatcgac gcctggggcc agggcacact agtgaccgtg    360
tcctcc                                                               366
```

<210> SEQ ID NO 126
<211> LENGTH: 366
<212> TYPE: DNA
<213> ORGANISM: Artificial Sequence
<220> FEATURE:
<223> OTHER INFORMATION: base sequence of heavy chain variable region of
      Clone HF2-21

<400> SEQUENCE: 126

```
gaggtgcagc tggtggagtc tggcggcgga ctggtgcagc ctggcggaag cttgcggctg     60
tcctgcgccg cctcctttca gtattttcgt tcccacggca tgcagtgggt gcggcaggcc    120
cctggcaagg gcctcgagta cgtggccggc atctcctccg acggctcctg gtatcgggtg    180
caggccgccg tggagggccg gttcaccatc tcccgcgacg actccaagaa caccgcctac    240
ctgcagatga actccctgcg ggccgaggac accgccgtgt actactgcgc cagagacttc    300
```

```
tccaccggct acggagccga ctccatcgac gcctggggcc agggcacact agtgaccgtg      360
tcctcc                                                                  366
```

<210> SEQ ID NO 127
<211> LENGTH: 366
<212> TYPE: DNA
<213> ORGANISM: Artificial Sequence
<220> FEATURE:
<223> OTHER INFORMATION: base sequence of heavy chain variable region of
      Clone HF2-22

<400> SEQUENCE: 127

```
gaggtgcagc tggtggagtc tggcggcgga ctggtgcagc ctggcggaag cttgcggctg       60
tcctgcgccg cctccggttt tcgtattagg tcccacggca tgcagtgggt gcggcaggcc      120
cctggcaagg gcctcgagta cgtggccggc atctcctccg acggctcctg gtttcgggtt      180
gctgccgccg tggagggccg gttcaccatc tcccgcgacg actccaagaa caccgcctac      240
ctgcagatga actccctgcg ggccgaggac accgccgtgt actactgcgc cagagacttc      300
tccaccggct acggagccga ctccatcgac gcctggggcc agggcacact agtgaccgtg      360
tcctcc                                                                  366
```

<210> SEQ ID NO 128
<211> LENGTH: 366
<212> TYPE: DNA
<213> ORGANISM: Artificial Sequence
<220> FEATURE:
<223> OTHER INFORMATION: base sequence of heavy chain variable region of
      Clone HF2-23

<400> SEQUENCE: 128

```
gaggtgcagc tggtggagtc tggcggcgga ctggtgcagc ctggcggaag cttgcggctg       60
tcctgcgccg cctccggttt tcgtattagg tcccacggca tgcagtgggt gcggcaggcc      120
cctggcaagg gcctcgagta cgtggccggc atctcctccg acggctcctg gttttctagt      180
gcggccgccg tggagggccg gttcaccatc tcccgcgacg actccaagaa caccgcctac      240
ctgcagatga actccctgcg ggccgaggac accgccgtgt actactgcgc cagagacttc      300
tccaccggct acggagccga ctccatcgac gcctggggcc agggcacact agtgaccgtg      360
tcctcc                                                                  366
```

<210> SEQ ID NO 129
<211> LENGTH: 366
<212> TYPE: DNA
<213> ORGANISM: Artificial Sequence
<220> FEATURE:
<223> OTHER INFORMATION: base sequence of heavy chain variable region of
      Clone HF2-24

<400> SEQUENCE: 129

```
gaggtgcagc tggtggagtc tggcggcgga ctggtgcagc ctggcggaag cttgcggctg       60
tcctgcgccg cctcccgttt taatatgcgg tcccacggca tgcagtgggt gcggcaggcc      120
cctggcaagg gcctcgagta cgtggccggc atctcctccg acggctcctg ggtgaaggtg      180
gcggccgccg tggagggccg gttcaccatc tcccgcgacg actccaagaa caccgcctac      240
ctgcagatga actccctgcg ggccgaggac accgccgtgt actactgcgc cagagacttc      300
tccaccggct acggagccga ctccatcgac gcctggggcc agggcacact agtgaccgtg      360
tcctcc                                                                  366
```

<210> SEQ ID NO 130
<211> LENGTH: 366
<212> TYPE: DNA
<213> ORGANISM: Artificial Sequence
<220> FEATURE:
<223> OTHER INFORMATION: base sequence of heavy chain variable region of
      Clone HF2-25

<400> SEQUENCE: 130

| gaggtgcagc | tggtggagtc | tggcggcgga | ctggtgcagc | ctggcggaag | cttgcggctg | 60 |
| tcctgcgccg | cctcctatat | ggagtatagg | tcccacggca | tgcagtgggt | gcggcaggcc | 120 |
| cctggcaagg | gcctcgagta | cgtggccggc | atctcctccg | acggctcctg | gtttcgtatg | 180 |
| aatgccgccg | tggagggccg | gttcaccatc | tcccgcgacg | actccaagaa | caccgcctac | 240 |
| ctgcagatga | actccctgcg | ggccgaggac | accgccgtgt | actactgcgc | cagagacttc | 300 |
| tccaccggct | acggagccga | ctccatcgac | gcctggggcc | agggcacact | agtgaccgtg | 360 |
| tcctcc | | | | | | 366 |

<210> SEQ ID NO 131
<211> LENGTH: 366
<212> TYPE: DNA
<213> ORGANISM: Artificial Sequence
<220> FEATURE:
<223> OTHER INFORMATION: base sequence of heavy chain variable region of
      Clone HF2-26

<400> SEQUENCE: 131

| gaggtgcagc | tggtggagtc | tggcggcgga | ctggtgcagc | ctggcggaag | cttgcggctg | 60 |
| tcctgcgccg | cctcccgttt | taatatgcgg | tcccacggca | tgcagtgggt | gcggcaggcc | 120 |
| cctggcaagg | gcctcgagta | cgtggccggc | atctcctccg | acggctcctg | gattcgggtg | 180 |
| caggccgccg | tggagggccg | gttcaccatc | tcccgcgacg | actccaagaa | caccgcctac | 240 |
| ctgcagatga | actccctgcg | ggccgaggac | accgccgtgt | actactgcgc | cagagacttc | 300 |
| tccaccggct | acggagccga | ctccatcgac | gcctggggcc | agggcacact | agtgaccgtg | 360 |
| tcctcc | | | | | | 366 |

<210> SEQ ID NO 132
<211> LENGTH: 72
<212> TYPE: DNA
<213> ORGANISM: Artificial Sequence
<220> FEATURE:
<223> OTHER INFORMATION: PCR forward primer for amplifying VH domain

<400> SEQUENCE: 132

| ggtcagtcct | ctagatcttc | cggcggtggt | ggcagctccg | gtggtggcgg | ttccgccgtg | 60 |
| acgttggacg | ag | | | | | 72 |

<210> SEQ ID NO 133
<211> LENGTH: 44
<212> TYPE: DNA
<213> ORGANISM: Artificial Sequence
<220> FEATURE:
<223> OTHER INFORMATION: PCR reverse primer for amplifying VH domain

<400> SEQUENCE: 133
ctggccggcc tggccactag tggaggagac gatgacttcg gtcc                44

<210> SEQ ID NO 134
<211> LENGTH: 38

```
<212> TYPE: DNA
<213> ORGANISM: Artificial Sequence
<220> FEATURE:
<223> OTHER INFORMATION: PCR forward primer for amplifying VL domain

<400> SEQUENCE: 134
gtggcccagg cggccctgac tcagccgtcc tcggtgtc                              38

<210> SEQ ID NO 135
<211> LENGTH: 34
<212> TYPE: DNA
<213> ORGANISM: Artificial Sequence
<220> FEATURE:
<223> OTHER INFORMATION: PCR reverse primer for amplifying VL domain

<400> SEQUENCE: 135
ggaagatcta gaggactgac ctaggacggt cagg                                  34

<210> SEQ ID NO 136
<211> LENGTH: 42
<212> TYPE: DNA
<213> ORGANISM: Artificial Sequence
<220> FEATURE:
<223> OTHER INFORMATION: PCR forward primer for amplifying ScFV

<400> SEQUENCE: 136
gaggaggagg aggaggaggt ggcccaggcg gccctgactc ag                         42

<210> SEQ ID NO 137
<211> LENGTH: 47
<212> TYPE: DNA
<213> ORGANISM: Artificial Sequence
<220> FEATURE:
<223> OTHER INFORMATION: PCR reverse primer for amplifying ScFV

<400> SEQUENCE: 137
gaggaggagg aggaggagga gctggccggc ctggccacta gtggagg                    47

<210> SEQ ID NO 138
<211> LENGTH: 20
<212> TYPE: DNA
<213> ORGANISM: Artificial Sequence
<220> FEATURE:
<223> OTHER INFORMATION: forward primer for sequencing of plasmid DNA
      (Clone F)

<400> SEQUENCE: 138
acactttatg cttccggctc                                                  20

<210> SEQ ID NO 139
<211> LENGTH: 20
<212> TYPE: DNA
<213> ORGANISM: Artificial Sequence
<220> FEATURE:
<223> OTHER INFORMATION: reverse primer for sequencing of plasmid DNA
      (Clone F)

<400> SEQUENCE: 139
caaaatcacc ggaaccagag                                                  20

<210> SEQ ID NO 140
<211> LENGTH: 19
<212> TYPE: DNA
<213> ORGANISM: Artificial Sequence
<220> FEATURE:
<223> OTHER INFORMATION: PCR forward primer for amplifying VH domain
      obtained from pComb3x
```

<400> SEQUENCE: 140
gctagccgcc accatgggc                                                    19

<210> SEQ ID NO 141
<211> LENGTH: 37
<212> TYPE: DNA
<213> ORGANISM: Artificial Sequence
<220> FEATURE:
<223> OTHER INFORMATION: PCR reverse primer for amplifying VH domain
      obtained from pComb3x

<400> SEQUENCE: 141 aggggcccttt ggtggaggcc tggccggcct ggccact                                37

<210> SEQ ID NO 142
<211> LENGTH: 20
<212> TYPE: DNA
<213> ORGANISM: Artificial Sequence
<220> FEATURE:
<223> OTHER INFORMATION: PCR forward primer for amplifying CH domain
      obtained from pComb3x

<400> SEQUENCE: 142
gcctccacca agggcccctc                                                   20

<210> SEQ ID NO 143
<211> LENGTH: 20
<212> TYPE: DNA
<213> ORGANISM: Artificial Sequence
<220> FEATURE:
<223> OTHER INFORMATION: PCR reverse primer for amplifying CH domain
      obtained from pComb3x

<400> SEQUENCE: 143
cgggatccct tgccggccgt                                                   20

<210> SEQ ID NO 144
<211> LENGTH: 19
<212> TYPE: DNA
<213> ORGANISM: Artificial Sequence
<220> FEATURE:
<223> OTHER INFORMATION: PCR forward primer for amplifying HC obtained
      from pComb3x

<400> SEQUENCE: 144
gctagccgcc accatgggc                                                    19

<210> SEQ ID NO 145
<211> LENGTH: 20
<212> TYPE: DNA
<213> ORGANISM: Artificial Sequence
<220> FEATURE:
<223> OTHER INFORMATION: PCR reverse primer for amplifying HC obtained
      from pComb3x

<400> SEQUENCE: 145
cgggatccct tgccggccgt                                                   20

<210> SEQ ID NO 146
<211> LENGTH: 18
<212> TYPE: DNA
<213> ORGANISM: Artificial Sequence
<220> FEATURE:
<223> OTHER INFORMATION: PCR forward primer for amplifying VL obtained
      from pComb3x

```
<400> SEQUENCE: 146
aagcttgccg ccaccatg                                                18

<210> SEQ ID NO 147
<211> LENGTH: 37
<212> TYPE: DNA
<213> ORGANISM: Artificial Sequence
<220> FEATURE:
<223> OTHER INFORMATION: PCR reverse primer for amplifying VL obtained
      from pComb3x

<400> SEQUENCE: 147 aggggggcggc cacggtccgg gaagatctag aggactg                          37

<210> SEQ ID NO 148
<211> LENGTH: 20
<212> TYPE: DNA
<213> ORGANISM: Artificial Sequence
<220> FEATURE:
<223> OTHER INFORMATION: PCR forward primer for amplifying Ck domain
      obtained from pComb3x

<400> SEQUENCE: 148
cggaccgtgg ccgcccctc                                               20

<210> SEQ ID NO 149
<211> LENGTH: 19
<212> TYPE: DNA
<213> ORGANISM: Artificial Sequence
<220> FEATURE:
<223> OTHER INFORMATION: PCR reverse primer for amplifying Ck domain
      obtained from pComb3x

<400> SEQUENCE: 149
gctctagact agcactcgc                                               19

<210> SEQ ID NO 150
<211> LENGTH: 18
<212> TYPE: DNA
<213> ORGANISM: Artificial Sequence
<220> FEATURE:
<223> OTHER INFORMATION: PCR forward primer for amplifying LC obtained
      from pComb3x

<400> SEQUENCE: 150
aagcttgccg ccaccatg                                                18

<210> SEQ ID NO 151
<211> LENGTH: 19
<212> TYPE: DNA
<213> ORGANISM: Artificial Sequence
<220> FEATURE:
<223> OTHER INFORMATION: PCR reverse primer for amplifying LC obtained
      from pComb3x

<400> SEQUENCE: 151
gctctagact agcactcgc                                               19
```